US005780676A

United States Patent [19]

Boehm et al.

[11] Patent Number: 5,780,676

[45] Date of Patent: Jul. 14, 1998

[54] COMPOUNDS HAVING SELECTIVE ACTIVITY FOR RETINOID X RECEPTORS, AND MEANS FOR MODULATION OF PROCESSES MEDIATED BY RETINOID X RECEPTORS

[75] Inventors: Marcus F. Boehm, San Diego; Richard A. Heyman, Encinitas; Lin Zhi, San Diego; Chan Kou Hwang, San Diego; Steve White, San Diego; Alex Nadzan, San Diego, all of Calif.

[73] Assignee: Ligand Pharmaceuticals Incorporated, San Diego, Calif.

[21] Appl. No.: 485,386

[22] Filed: Jun. 7, 1995

Related U.S. Application Data

[63] Continuation of Ser. No. 141,246, Oct. 22, 1993, which is a continuation-in-part of Ser. No. 52,050, Apr. 21, 1993, abandoned, which is a continuation-in-part of Ser. No. 27,747, Mar. 5, 1993, abandoned, which is a continuation-in-part of Ser. No. 3,223, Jan. 11, 1993, abandoned, which is a continuation-in-part of Ser. No. 944,783, Sep. 11, 1992, abandoned, which is a continuation-in-part of Ser. No. 872,707, Apr. 22, 1992, abandoned.

[51] Int. Cl.[6] ........ C07C 63/36

[52] U.S. Cl. ........ 562/490; 562/501; 554/220; 554/221

[58] Field of Search ........ 562/490, 501; 554/220, 221

[56] References Cited

U.S. PATENT DOCUMENTS

| | | |
|---|---|---|
| 2,897,237 | 7/1959 | Carpenter et al. . |
| 3,398,121 | 8/1968 | Oxenrider et al. . |
| 3,507,906 | 4/1970 | Oxenrider et al. . |
| 3,639,464 | 2/1972 | Oxenrider et al. . |
| 4,141,995 | 2/1979 | Saunders et al. . |
| 4,539,154 | 9/1985 | Krebs . |
| 4,548,723 | 10/1985 | Shippey . |
| 4,833,240 | 5/1989 | Maignan et al. . |
| 4,877,805 | 10/1989 | Kligman . |
| 4,898,864 | 2/1990 | Maignan et al. . |
| 4,981,784 | 1/1991 | Evans et al. . |
| 5,023,341 | 6/1991 | Chandraratna . |
| 5,023,363 | 6/1991 | Maignan et al. . |
| 5,053,523 | 10/1991 | Chandraratna . |
| 5,071,773 | 12/1991 | Evans et al. . |
| 5,093,516 | 3/1992 | Maignan et al. . |
| 5,399,586 | 3/1995 | Davies et al. . |
| 5,466,861 | 11/1995 | Dawson et al. . |

FOREIGN PATENT DOCUMENTS

| | | |
|---|---|---|
| 0552624 | 11/1901 | European Pat. Off. . |
| 0260162 | 3/1988 | European Pat. Off. . |
| 0284261 | 9/1988 | European Pat. Off. . |
| 0284288 | 9/1988 | European Pat. Off. . |
| 2601670 | 1/1988 | France . |
| 1082269 | 9/1967 | United Kingdom . |
| 1526410 | 9/1978 | United Kingdom . |
| 1549171 | 7/1979 | United Kingdom . |
| 2197316 | 5/1988 | United Kingdom . |
| 2228734 | 6/1990 | United Kingdom . |
| 8500806 | 2/1985 | WIPO . |
| 9306086 | 4/1993 | WIPO . |
| 9311755 | 6/1993 | WIPO . |
| 9412880 | 6/1994 | WIPO . |
| 9417796 | 8/1994 | WIPO . |

OTHER PUBLICATIONS

Angel et al., *Mol. Cell. Biol.*, 7:2256 (1987).
Ashwell et al., *Proc. Nat'l Acad. Sci.*, 90:6170–74 (1993).
Berger, T.S. et al., *J. Steroid Biochem. Molec. Biol.*, 41:733–38 (1992).
Bradley, L.M., *Selected Methods in Cellular Immunology*, Ch. 10.1, pp. 235–238, Mishell & Shiigi (eds.), Freeman & Co., New York (1980).
Brietman et al., *Proc. Nat'l Acad. Sci.*, 77:2936 (1980).
Brand, N. et al., *Nature*, 332:850–53 (Apr. 28, 1988).
*Chemical Abstracts*, vol. 84, No. 15, Abstract No. 105844 (Apr. 12, 1976).
*Chemical Abstracts*, vol. 88, No. 20, Abstract No. 144612 (May 15, 1978).
Englert, Gerhard, *Helvetica Chimica Acta*, vol. 58, Fasc. 8, pp. 2367–2390 (1975).
Evans, R.M., *Science*, 240:889–95 (May 13, 1988).
Giguere, V. et al., *Nature*, 330:624–29 (Dec. 17, 1987).
Gordon et al., *New England J. Med.*, 321:1311 (1989).
Heyman, R.A. et al., *Cell*, 68:397–406 (Jan. 24, 1992).
Hollenberg, S.M. et al., *Cell*, 55:899–906 (Dec. 2, 1988).
Ishikawa, T. et al., *Mol. Endo.*, 4:837–44 (1990).
Isseman & Green, *Nature*, 347:645–49 (1990).
Jong, L. et al., *J. Med. Chem.*, 36:2605–13 (1993).
Kliewer et al., *Nature*, 358:771 (1992).
Kligman, L.H. et al., *J. of Invest. Derm.*, 73:354–58 (1979).
Ladias et al., *Science*, 251:561–65 (1991).
Lafyatis et al., *Mol. Endocrinol.*, 4:973 (1990).
Lehmann, J.M. et al., *Science*, 258:1944–46 (1992).
Levin, A.A. et al., *Nature*, 355:359–61 (Jan. 23, 1992).
Loeliger, P. et al., Eur. J. Med. Chem.—Chimica Therapeutica, vol. 15, No. 1, pp. 9–15 (1980).
Mangelsdorf, D.J. et al., *Nature*, 345:224–29 (May 17, 1990).
Mangelsdorf, D.J. et al., *Cell*, 66:555–61 (Aug. 9, 1991).
Mangelsdorf, D.J. et al., *Genes & Devel.*, 6:329–44 (1992).
Mezick, J.A. et al., *J. of Invest. Derm.*, 83:110–13 (1984).
Miyajima et al., *Nucleic Acids Research*, 16:11057–74 (1988).
Mlodzik et al., *Cell*, 60:211–24 (1990).

(List continued on next page.)

*Primary Examiner*—Paul J. Killos
*Attorney, Agent, or Firm*—Lyon & Lyon LLP

[57] ABSTRACT

Compounds, compositions, and methods for modulating processes mediated by Retinoid X Receptors using retinoid-like compounds which have activity selective for members of the subclass of Retinoid X Receptors (RXRs), in preference to members of the subclass of Retinoic Acid Receptors (RARs). Examples of such compounds are bicyclic benzyl, pyridinyl, thiophene, furanyl, pyrrole, and polyenoic acid derivatives including carbocyclic polyenoic acids. The disclosed methods employ compounds for modulating processes selectively mediated by Retinoid X Receptors.

23 Claims, 12 Drawing Sheets

OTHER PUBLICATIONS

Murtaugh et al., *J. Biol. Chem.*, 258:11074 (1983).
Oro et al., *Nature*, 347:298–301 (1990).
Petkovich, M. et al., *Nature*, 330:444–50 (Dec. 3, 1987).
Rottman et al., *Mol. Cell. Biol.*, 11:3814–20 (1991).
Rubin et al., *Nature*, 353:265 (1991).
Schenk, H. et al., Acta Cryst., vol. B34, pp. 505–507 (1978).
Shirvastav et al., *Cancer Res.*, 40:4438 (1980).
Sladek et al., *Genes & Development*, 4:2353–65 (1990).
Umesono, K. et al., *Nature*, 336:262–65 (Nov. 17, 1988).
Umesono, K. & Evans, R.M., *Cell*, 57:1139–46 (Jun. 30, 1989).

Wang et al., *Nature*, 340:163–66 (1989).

Wecksler & Norman, *Anal. Biochem.*, 92:314–23 (1979).

Widom et al., *Mol. Cell. Biol.*, 12:3380–89 (1992).

Yang, N. et al., *Proc. Natl. Acad. Sci. USA*, 88:3559–63 (May 1991).

Yoshihide, et al., Chemical Abstracts, 4473Of, vol. 83, p. 72 (1975).

Yuspa, S.H. et al., *Cancer Research*, 43:5707–12 (Dec., 1983).

COMPOUNDS HAVING SELECTIVE ACTIVITY FOR RETINOID X RECEPTORS, AND MEANS FOR MODULATION OF PROCESSES MEDIATED BY RETINOID X RECEPTORS

RELATED APPLICATIONS

This is a continuation of application Ser. No. 08/141,246 filed on Oct. 22, 1993, which is a continuation-in-part of Ser. No. 08/052,050 filed on Apr. 21, 1993, now abandoned, which is a continuation-in-part of Ser. No. 08/027,747 filed on Mar. 5, 1993, now abandoned, which is a continuation-in-part of Ser. No. 08/003,223 filed on Jan. 11, 1993, now abandoned, which is a continuation-in-part of Ser. No. 07/944,783 filed on Sep. 11, 1992, now abandoned, which is a continuation-in-part of Ser. No. 07/872,707 filed on Apr. 22, 1992, now abandoned.

FIELD OF THE INVENTION

This invention relates to intracellular receptors and ligands therefor. More specifically, this invention relates to compounds having selective activity for specific retinoic acid receptors, and methods for use of such compounds.

BACKGROUND OF THE INVENTION

The vitamin A metabolite retinoic acid has long been recognized to induce a broad spectrum of biological effects. A variety of structural analogues of retinoic acid have been synthesized that also have been found to be bioactive. Some, such as Retin-A® (registered trademark of Johnson & Johnson) and Accutane® (registered trademark of Hoffmann-LaRoche), have found utility as therapeutic agents for the treatment of various pathological conditions. Metabolites of vitamin A and their synthetic analogues are collectively herein called "retinoids".

Synthetic retinoids have been found to mimic many of the pharmacological actions of retinoic acid. However, the broad spectrum of pharmacological actions of retinoic acid is not reproduced in full by all bioactive synthetic retinoids.

Medical professionals have become very interested in the medicinal applications of retinoids. Among their uses approved by the FDA is the treatment of severe forms of acne and psoriasis. A large body of evidence also exists that these compounds can be used to arrest and, to an extent, reverse the effects of skin damage arising from prolonged exposure to the sun. Other evidence exists that these compounds may be useful in the treatments of a variety of severe cancers including melanoma, cervical cancer, some forms of leukemia, and basal and squamous cell carcinomas. Retinoids have also shown an ability to be efficacious in treating premalignant cell lesions, such as oral leukoplakia, and to prevent the occurrence of malignancy.

Use of the retinoids is associated with a number of significant side effects. The most serious of these is that, as a class, they are among the most potent teratogens known. Teratogens are compounds that cause severe birth defects during specific periods of fetal exposure. Other side effects include irritation of the tissues treated, which can be so severe that patients cannot tolerate treatment.

Various investigations have been undertaken to elucidate the structure-activity relationships governing the abilities of synthetic retinoids to induce the various pharmacological consequences of retinoic acid exposure. This has been a complicated task, however, since the assays available to investigators have been bioassays, carried out either in intact animals or in isolated tissues. Technical constraints have often dictated the use of different small animal species for different assays. Interpretation of results has been complicated by possible pharmacokinetic and metabolic effects and possible species differences in the receptors involved. Nevertheless, definite differences in the pharmacological effects of various synthetic retinoids have been observed.

Major insight into the molecular mechanism of retinoic acid signal transduction was gained in 1988. Prior to that time, several high abundance cellular retinoid binding proteins were incorrectly inferred to be the signal transducing receptors for retinoic acid. In 1988, a member of the steroid/thyroid hormone intracellular receptor superfamily (Evans, *Science*, 240: 889–95 (1988)) was shown to transduce a retinoic acid signal (Giguere et al., *Nature*, 330: 624–29 (1987); Petkovich et al., *Nature*, 330: 444–50 (1987)). This unexpected finding related retinoic acid to other non-peptide hormones and elucidated the mechanism of retinoic acid effects in altering cell function. It is now known that retinoids regulate the activity of two distinct intracellular receptor subfamilies; the Retinoic Acid Receptors (RARs) and the Retinoid X Receptors (RXRs).

The first retinoic acid receptor identified, designated RAR-alpha, acts to modulate transcription of specific target genes in a manner which is ligand-dependent, as has been shown to be the case for many of the members of the steroid/thyroid hormone intracellular receptor superfamily. The endogenous low-molecular-weight ligand upon which the transcription-modulating activity of RAR-alpha depends is all-trans-retinoic acid. Retinoic acid receptor-mediated changes in gene expression result in characteristic alterations in cellular phenotype, with consequences in many tissues manifesting the biological response to retinoic acid. Two additional genes closely related to RAR-alpha were recently identified and were designated RAR-beta and RAR-gamma and are very highly related (Brand et al., *Nature*, 332: 850–53 (1988); Ishikawa et al., *Mol. Endocrin.*, 4: 837–44 (1990)). In the region of the retinoid receptors which can be shown to confer ligand binding, the primary amino acid sequences diverge by less than 15% among the three RAR subtypes or isoforms. All-trans-retinoic acid is a natural ligand for the retinoic acid receptors (RARs) and is capable of binding to these receptors with high affinity, resulting in the regulation of gene expression. The newly-discovered retinoid metabolite, 9-cis-retinoic acid, is also an activator of RARs.

A related but unexpected observation was made recently (Mangelsdorf et al., *Nature*, 345: 224–29 (1990)), in which another member of the steroid/thyroid receptor superfamily was also shown to be responsive to retinoic acid. This new retinoid receptor subtype has been designated Retinoid X Receptor (RXR), because certain earlier data suggested that a derivative of all-trans-retinoic acid may be the endogenous ligand for RXR. Like the RARs, the RXRs are also known to have at least three subtypes or isoforms, namely RXR-alpha, RXR-beta, and RXR-gamma, with corresponding unique patterns of expression (Manglesdorf et al., *Genes & Devel.*, 6: 329–44 (1992)).

Although both the RARs and RXRs respond to all-trans-retinoic acid in vivo, the receptors differ in several important aspects. First, the RARs and RXRs are significantly divergent in primary structure (e.g., the ligand binding domains of RARα and RXRα have only 27% amino acid identity). These structural differences are reflected in the different relative degrees of responsiveness of RARs and RXRs to various vitamin A metabolites and synthetic retinoids. In addition, distinctly different patterns of tissue distribution are seen for RARα and RXRS. For example, in contrast to the RARs, which are not expressed at high levels in the visceral tissues, RXRα mRNA has been shown to be most abundant in the liver, kidney, lung, muscle and intestine. Finally, the RARs and RXRs have different target gene specificity. For example, response elements have recently been identified in the cellular retinal binding protein type II (CRBPII) and apolipoprotein AI genes which confer responsiveness to RXR, but not RAR. Furthermore, RAR has also been recently shown to repress RXR-mediated activation through the CRBPII RXR response element (Manglesdorf et al., *Cell*, 66: 555–61 (1991)). These data indicate that two retinoic acid responsive pathways are not simply redundant, but instead manifest a complex interplay. Recently, Heyman etal. (*Cell*, 68: 397–406 (1992)) and Levin et al. (*Nature*, 355: 359–61 (1992)) independently demonstrated that 9-cis-retinoic acid is a natural endogenous ligand for the RXRs. 9-cis-retinoic acid was shown to bind and transactivate the RXRs, as well as the RARs, and therefore appears to act as a "bifunctional" ligand.

In view of the related, but clearly distinct, nature of these receptors, ligands which are more selective for the Retinoid X Receptor subfamily would be of great value for selectively controlling processes mediated by one or more of the RXR isoforms, and would provide the capacity for independent control of the physiologic processes mediated by the RXRs. Ligands which preferentially affect one or more but not all of the receptor isoforms also offer the possibility of increased therapeutic efficacy when used for medicinal applications.

The entire disclosures of the publications and references referred to above and hereafter in this specification are incorporated herein by reference.

SUMMARY OF THE INVENTION

The present invention is directed to compounds, compositions, and methods for modulating processes mediated by one or more Retinoid X Receptors. More particularly, the invention relates to compounds which selectively or preferentially activate Retinoid X Receptors, in comparison to Retinoic Acid Receptors. These compounds selectively modulate processes mediated by Retinoid X Receptors. Accordingly, the invention also relates to methods for modulating processes selectively mediated by one or more Retinoid X Receptors, in comparison to Retinoic Acid Receptors, by use of the compounds of this invention. Examples of compounds used in and forming part of the invention include bicyclic benzyl, pyridinyl, thiophene, furanyl, pyrrole, and polyenoic acid derivatives including carbocyclic polyenoic acids. Pharmaceutical compositions containing the compounds disclosed are also within the scope of this invention. Also included are methods for identifying or purifying Retinoid X Receptors by use of the compounds of this invention.

BRIEF DESCRIPTION OF THE FIGURES

The present invention may be better understood and its advantages appreciated by those skilled in the art by referring to the accompanying drawings wherein.

DETAILED DESCRIPTION OF THE INVENTION

Figure 1:
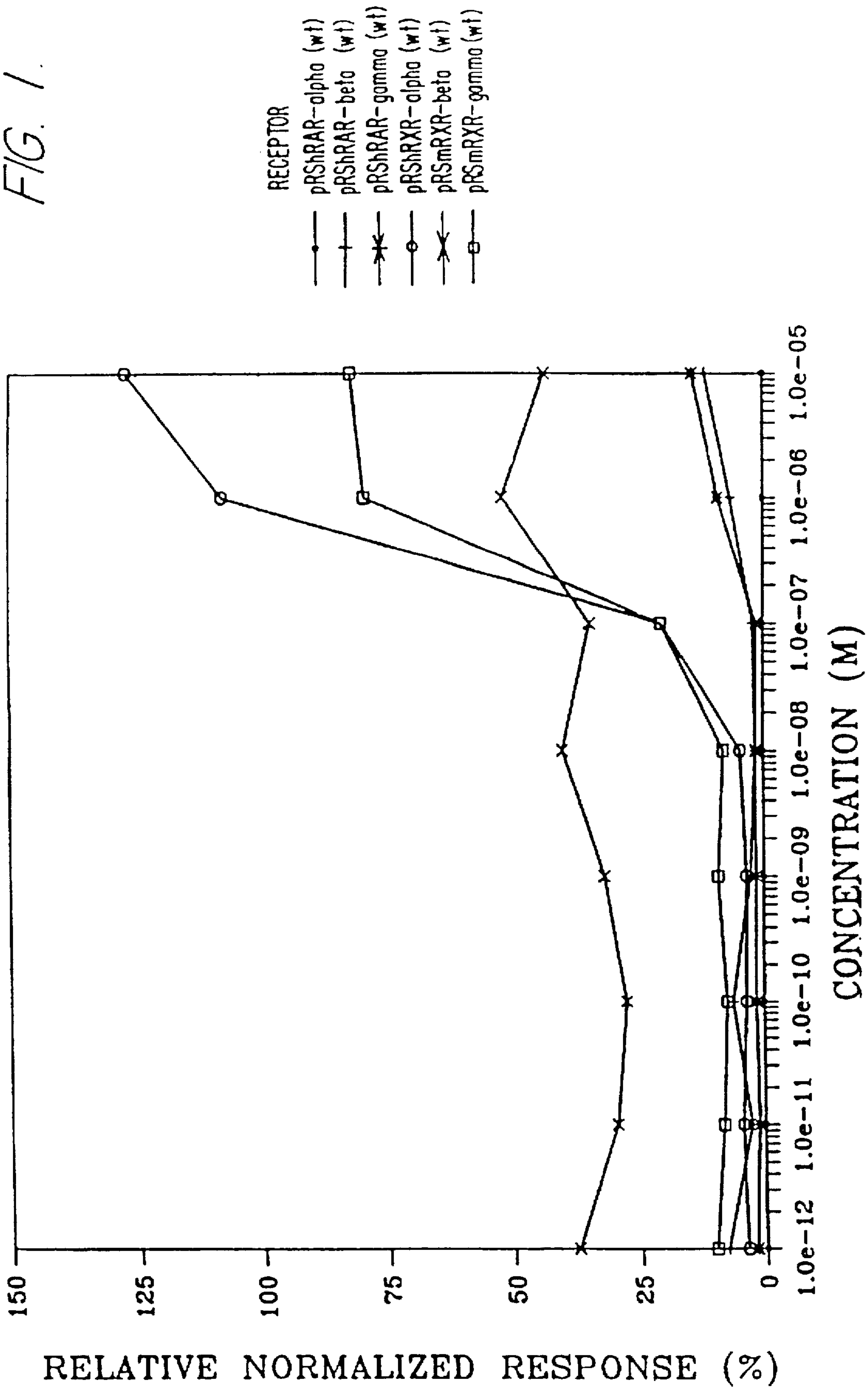
FIG. 1 presents the standardized dose response profiles showing the transactivation of RAR and RXR isoforms by 3-methyl-TTNCB.

This invention discloses retinoid-like compounds or ligands which have selective activity for members of the subfamily of Retinoid X Receptors (RXRs), in comparison to members of the subfamily of Retinoic Acid Receptors (RARs). Examples of such compounds are bicyclic benzyl, pyridinyl, thiophene, furanyl, pyrrole, and polyenoic acid derivatives which can be represented by the formulae:

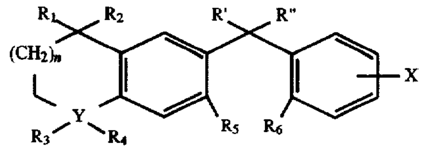

or

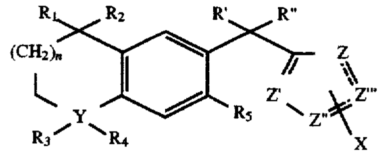

or

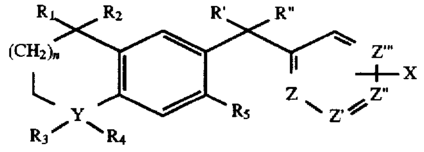

or

-continued

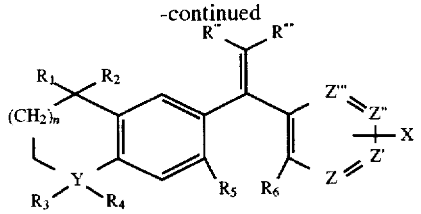

or

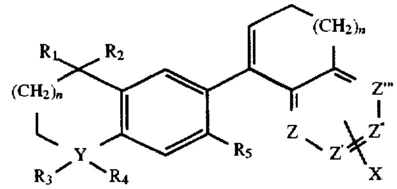

or

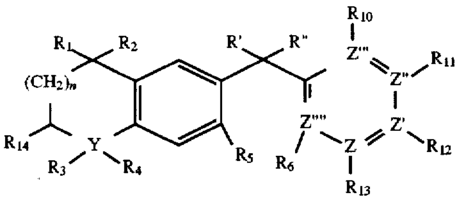

or

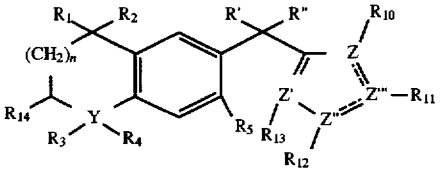

or

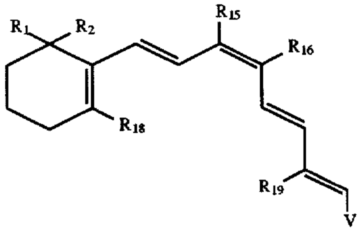

or

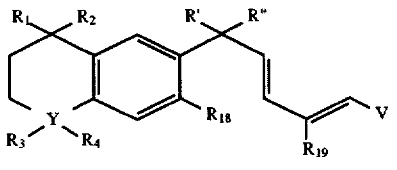

or

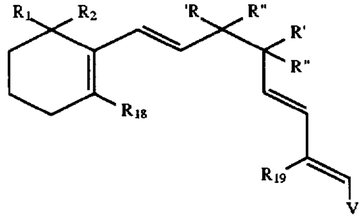

-continued or

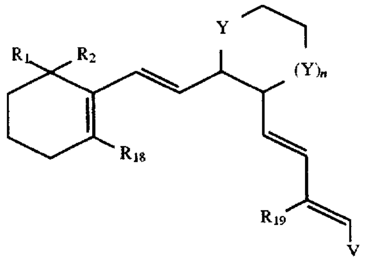

wherein $R_1$ and $R_2$, each independently, represent hydrogen or lower alkyl or acyl having 1–4 carbon atoms;

Y represents C, O, S, N, CHOH, CO, SO, $SO_2$, or a pharmaceutically acceptable salt;

$R_3$ represents hydrogen or lower alkyl having 1–4 carbon atoms where Y is C or N;

$R_4$ represents hydrogen or lower alkyl having 1–4 carbon atoms where Y is C, but $R_4$ does not exist if Y is N, and neither $R_3$ or $R_4$ exist if Y is S, O, CHOH, CO, SO, or $SO_2$;

R' and R" represent hydrogen, lower alkyl or acyl having 1–4 carbon atoms, OH, alkoxy having 1–4 carbon atoms, thiol or thio ether, or amino, or R' or R" taken together form an oxo (keto), methano, thioketo, HO—N=, NC—N=, $(R_7R_8)N$—N=, $R_{17}O$—N=, $R_{17}N$=, epoxy, cyclopropyl, or cycloalkyl group and wherein the epoxy, cyclopropyl, and cycloalkyl groups can be substituted with lower alkyl having 1–4 carbons or halogen;

R'" and R"" represent hydrogen, halogen, lower alkyl or acyl having 1–4 carbon atoms, alkyl amino, or R'" and R"" taken together form a cycloalkyl group having 3–10 carbons, and wherein the cycloalkyl group can be substituted with lower alkyl having 1–4 carbons or halogen;

$R_5$ represents hydrogen, a lower alkyl having 1–4 carbons, halogen, nitro, $OR_7$, $SR_7$, $NR_7R_8$, or $(CF)_nCF_3$, but $R_5$ cannot be hydrogen if together $R_6$, $R_{10}$, $R_{11}$, $R_{12}$ and $R_{13}$ are all hydrogen, Z, Z', Z", Z'", and Z"" are all carbon, and R' and R" represent H, OH, $C_1$–$C_4$ alkoxy or $C_1$–$C_4$ acyloxy or R' and R" taken together form an oxo, methano, or hydroxyimino group;

$R_6$, $R_{10}$, $R_{11}$, $R_{12}$, $R_{13}$ each independently represent hydrogen, a lower alkyl having 1–4 carbons, halogen, nitro, $OR_7$, $SR_7$, $NR_7R_8$ or $(CF)_nCF_3$, and exist only if the Z, Z', Z", Z'", or Z from which it originates is C, or each independently represent hydrogen or a lower alkyl having 1–4 carbons if the Z, Z', Z", Z'", or Z"" from which it originates is N, and where one of $R_6$, $R_{10}$, $R_{11}$, $R_{12}$ or $R_{13}$ is X;

$R_7$ represents hydrogen or a lower alkyl having 1–6 carbons;

$R_8$ represents hydrogen or a lower alkyl having 1–6 carbons;

$R_9$ represents a lower alkyl having 1–4 carbons, phenyl, aromatic alkyl, or q-hydroxyphenyl, g-bromophenyl, q-chlorophenyl, q-florophenyl, or q-idodophenyl, where q=2–4:

$R_{14}$ represents hydrogen, a lower alkyl having 1–4 carbons, oxo, hydroxy, acyl having 1–4 carbons, halogen, thiol, or thioketone;

$R_{15}$ represents a lower or branched alkyl having 1–12 carbons and can be methyl only if $R_{16}$ is a halogen or a lower alkyl having 1–8 carbons;

$R_{16}$ represents hydrogen, a lower alkyl having 1–8 carbons, or halogen, or $R_{15}$ and $R_{16}$ taken together form a phenyl. cyclohexyl. or cyclopental ring. or one of the following:

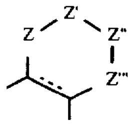
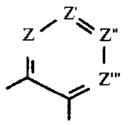
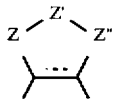
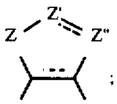
;

$R_{17}$ represents hydrogen. lower alkyl having 1–8 carbons. alkenyl (including halogen. acyl. $OR_7$ and $SR_7$ substituted alkenes). $R_9$. alkyl carboxylic acid (including halogen. acyl. $OR_7$ and $SR_7$ substituted alkyls). alkenyl carboxylic acid (including halogen acyl. $OR_7$ and $SR_7$ substituted alkenes). alkyl amines (including halogen. acyl. $OR_7$ and $SR_7$ substituted alkyls). and alkenyl amines (including halogen. acryl. $OR_7$ and $SR_7$ substituted alkenes);

$R_{18}$ represents hydrogen. a lower alkyl having 1–4 carbons. halogen. nitro. $OR_7$. $SR_7$. $NR_7R_8$ or $(CF)_n$ $CF_3$;

$R_{19}$ represents hydrogen. lower alkyl having 1–8 carbons. halogen. $OR_7$. $SR_7$. or $(CF)_n$ $CF_3$;

X is COOH. tetrazole. $PO_3H$. $SO_3H$. CHO. $CH_2OH$. $CONH_2$. COSH. $COOR_9$. $COSR_9$. $CONHR_9$. or COOW where W is a pharmaceutically acceptable salt. and where X can originate from any C or N on the ring;

V is COOH. tetrazole. $PO_3H$. $SO_3H$. CHO. $CH_2OH$. $CONH_2$. COSH. $COOR_9$. $COSR_9$. $CONHR_9$. or COOW where W is a pharmaceutically acceptable salt;

Z. Z'. Z". Z'". and Z"". each independently. represent C. S. O. N. or a pharmaceutically acceptable salt but is not O or S if attached by a double bond to another such Z or if attached to another such Z which is O or S. and is not N if attached by a single bond to another such Z which is N;

n=0–3; and the dashed lines in the structures depict optional double bonds.

As used in this disclosure. pharmaceutically acceptable salts include but are not limited to: hydrochloric. hydrobromic. hydroiodic. hydrofluoric. sulfuric. citric. maleic. acetic. lactic. nicotinic. succinic. oxalic. phosphoric. malonic. salicylic. phenylacetic. stearic. pyridine. ammonium. piperazine. diethylamine. nicotinamide. formic. urea. sodium. potassium. calcium. magnesium. zinc. lithium. cinnamic. methylamino. methanesulfonic. picric. tartaric. triethylamino. dimethylamino. and tris(hydroxymethyl) aminomethane. Additional pharmaceutically acceptable salts are known to those of skill in the art.

Representative derivatives according to the present invention include the following:

p[3.5.5.8.8-pentamethyl-1.2.3.4-tetrahydro-2-naphthyl-(2-carbonyl)]-benzoic acid. also known as 4-[(3.5.5.8.8-pentamethyl-5.6.7.8-tetrahydro-2-naphthyl)carbonyl] benzoic acid. and designated "3-methyl-TTNCB";

p|5.5.8.8-tetramethyl-1.2.3.4-tetrahydro-3-isopropyl-2-naphthyl-(2-carbonyl)|-benzoic acid. also known as 4-[(3-isopropyl-5.5.8.8-tetramethyl-5.6.7.8-tetrahydro-2-naphthyl)carbonyl|benzoic acid. and designated "3-IPR-TTNCB" or Compound 37;

p|5.5.8.8-tetramethyl-1.2.3.4-tetrahydro-3-isopropyl-2-naphthyl-(2-methano)|-benzoic acid. also known as 4-|1-(3-isopropyl-5.5.8.8-tetramethyl-5.6.7.8-tetrahydro-2naphthyl)ethenyl|benzoic acid. and designated "3-IPR-TTNEB" or Compound 42;

p|5.5.8.8-tetramethyl-1.2.3.4-tetrahydro-3-ethyl-2-naphthyl (2-methano)|-benzoic acid. also known as 4-|1-(3-ethyl-5.5.8.8-tetramethyl-5.6.7.8-tetrahydro-2-naphthyl) ethenyl|benzoic acid. and designated "3-ethyl-TTNEB" or Compound 45;

p|5.5.8.8-tetramethyl-1.2.3.4-tetrahydro-3-bromo-2-naphthyl(2-methano)|-benzoic acid. also known as 4-|1-(3-bromo-5.5.8.8-tetramethyl-5.6.7.8-tetrahydro-2-naphthyl)ethenyl|benzoic acid. and designated "3-bromo-TTNEB" or Compound 46;

p|5.5.8.8-tetramethyl-1.2.3.4-tetrahydro-3-chloro-2-naphthyl(2-methano)|-benzoic acid. also known as 4-|1-(3-chloro-5.5.8.8-tetramethyl-5.6.7.8-tetrahydro-2-naphthyl)ethenyl|benzoic acid. and designated "3-chloro-TTNEB" or Compound 43;

p|3.5.5.8.8-pentamethyl-1.2.3.4-tetrahydro-2-naphthyl-(2-methano)|-benzoic acid. also known as 4-|1-(3.5.5.8.8-pentamethyl-5.6.7.8-tetrahydro-2-naphthyl)ethenyl| benzoic acid. and designated "3-methyl-TTNEB";

p|3.5.5.8.8-pentamethyl-1.2.3.4-tetrahydro-2-naphthyl-(2-hydroxymethyl)|-benzoic acid. also known as 4-|1-(3.5.5.8.8-pentamethyl-5.6.7.8-tetrahydro-2-naphthyl) hydroxymethyl|benzoic acid. and designated "3-methyl-TTNHMB";

p|5.5.8.8-tetramethyl-1.2.3.4-tetrahydro-3-bromo-2-naphthyl-(2-carbonyl)|-benzoic acid. also known as 4-[(3-bromo-5.5.8.8-tetramethyl-5.6.7.8-tetrahydro-2-naphthyl)carbonyl|benzoic acid. and designated "3-bromo-TTNCB" or Compound 41;

p|5.5.8.8-tetramethyl-1.2.3.4-tetrahydro-3-chloro-2-naphthyl-(2-carbonyl)|-benzoic acid. also known as 4-[(3-chloro-5.5.8.8-tetramethyl-5.6.7.8-tetrahydro-2-naphthyl)carbonyl|benzoic acid. and designated "3-chloro-TTNCB" or Compound 38;

p|5.5.8.8-tetramethyl-1.2.3.4-tetrahydro-3-hydroxy-2-naphthyl-(2-carbonyl)|-benzoic acid. also known as 4-[(3-hydroxy-5.5.8.8-tetramethyl- 5.6.7.8-tetrahydro-2-naphthyl)carbonyl|benzoic acid. and designated "3-hydroxy-TTNCB" or Compound 39;

p|5.5.8.8-tetramethyl-1.2.3.4-tetrahydro-3-ethyl-2-naphthyl-(2-carbonyl)|-benzoic acid. also known as 4-[(3-ethyl-5.5.8.8-tetramethyl-5.6.7.8-tetrahydro-2-naphthyl)carbonyl|benzoic acid. and designated "3-ethyl-TTNCB" or Compound 40;

p[3.5.5.8.8-pentamethyl-1.2.3.4-tetrahydro-2-naphthyl-(2-thioketo)]-benzoic acid. also known as 4-[(3.5.5.8.8-pentamethyl-5.6.7.8-tetrahydro-2-naphthyl)thioketo| benzoic acid. and designated "thioketone";

p[3.5.5.8.8-pentamethyl-1.2.3.4-tetrahydro-2-naphthyl-(2-carbonyl)|-N-(4-hydroxyphenyl)benzamide. also known as 4-[(3.5.5.8.8-pentamethyl-5.6.7.8-tetrahydro-2-naphthyl)carbonyl]-N (4-hydroxyphenyl)benzamide. and designated "3-methyl-TTNCHBP";

p[3.5.5.8.8-pentamethyl-1.2.3.4-tetrahydro-2-naphthyl-(2-methano)]-N-(4-hydroxyphenyl)benzamide. also known as 4-[1-(3.5.5.8.8-pentamethyl-5.6.7.8-tetrahydro-2-naphthyl)ethenyl]-N-(4-hydroxyphenyl)benzamide. and designated "3-methyl-TTNEHBP" or Compound 63;

2-[1-(3.5.5.8.8-pentamethyl-5.6.7.8-tetrahydro-2-naphthyl) ethenyl]pyridine-5-carboxylic acid. designated "TPNEP" or Compound 58;

ethyl 2-|1-(3.5.5.8.8-pentamethyl-5.6.7.8-tetrahydro-2-naphthyl)ethenyl|pyridine-5-carboxylate. designated "TPNEPE" or Compound Et-58;

2-|1-(5.5.8.8-tetramethyl-5.6.7.8-tetrahydro-2-naphthyl) ethenyl]pyridine-5-carboxylic acid. designated "TTNEP" or Compound 56;

4-[1-(3.5.5.8.8-pentamethyl-5.6.7.8-tetrahydro-2-naphthyl) epoxy]benzoic acid. designated "TPNEB" or Compound 47;

4-|1-(3.5.5.8.8-pentamethyl-5.6.7.8-tetrahydro-2-naphthyl) cyclopropyl|benzoic acid. designated "TPNCB" or Compound 48;

4-[1-(3,5,5,8,8-pentamethyl-5,6,7,8-tetrahydro-2-naphthyl)ethenyl]benzenetetrazole, designated "3-methyl-TTNEBT" or Compound 55;

5-[1-(3,5,5,8,8-pentamethyl-5,6,7,8-tetrahydro-2-naphthyl)ethenyl]pyridine-2-carboxylic acid, designated "TPNEPC" or Compound 60;

2-[1-(3,5,5,8,8-pentamethyl-5,6,7,8-tetrahydro-2-naphthyl)cyclopropyl]pyridine-5-carboxylic acid, designated "TPNCP" or Compound 62;

methyl 2-[1-(3,5,5,8,8-pentamethyl-5,6,7,8-tetrahydro-2-naphthyl)cyclopropyl)pyridine-5-carboxylate, designated Compound Me-62;

3-methyl-7-propyl-9-(2,6,6-trimethyl-1-cyclohexen-1-yl)-2E, 4E,6Z,8E-nonatetranoic acid, designated Compound 74;

3-methyl-7-isopropyl-9-(2,6,6-trimethyl-1-cyclohexen-1-yl)-2E,4E,6Z,8E-nonatetranoic acid, designated Compound 75;

3-methyl-7-t-butyl-9-(2,6,6-trimethyl-1-cyclohexen-1-yl)-2E, 4E,6Z,8E-nonatetranoic acid, designated Compound 77;

3-methyl-5-{2-[2-(2,6,6-trimethylcyclohexen-1-yl)ethenyl]cyclohexyl}-2E,4E-pentadienoic acid, designated Compound 100;

(2E,4E)-3-methyl-5-[1-(3,5,5,8,8-pentamethyl-5,6,7,8-tetrahydro-2-naphthyl)cyclopropyl]penta-2,4-dienoic acid, designated Compound 104;

(2E,4E)-3-methyl-6-(1-[2,6,6-trimethyl-1-cyclohexenyl)ethenyl]cyclopropyl)-2,4-hexadienoic acid, designated Compound 110;

(2E,4E,6Z)-7-(5,5,8,8-tetramethyl-5,6,7,8-tetrahydro-2-naphthyl)-3,8-dimethyl-nona-2,4,6-trienoic acid, designated Compound 123; and (2E,4E,6Z)-7-(3,5,5,8,8-pentamethyl-5,6,7,8-tetrahydro-2-naphthyl)-3-methyl-octa-2,4,6-trienoic acid, designated Compound 128.

Representative structures for such compounds are as follows:

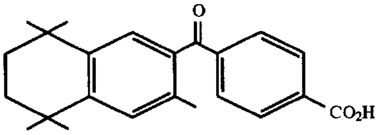

3-methyl-TTNCB

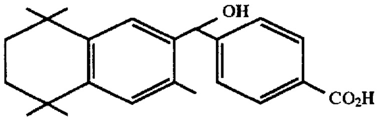

3-methyl-TTNHMB

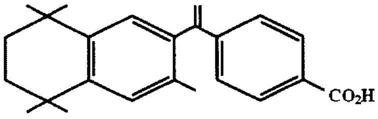

3-methyl-TTNEB

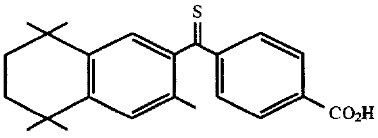

thioketone

-continued

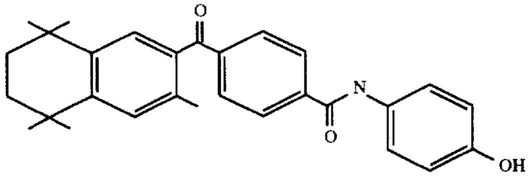

3-methyl-TTNCHBP

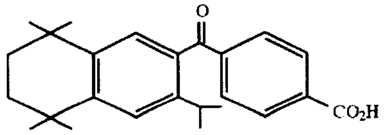 37

4-[(3-isopropyl-5,5,8,8-tetramethyl-5,6,7,8-tetrahydro-2-naphthyl)carbonyl]benzoic acid(3-IPr-TTNCB)

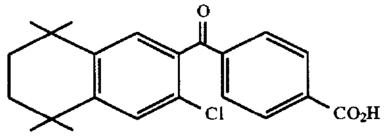 38

4-[(3-chloro-5,5,8,8-tetramethyl-5,6,7,8-tetrahydro-2-naphthyl)carbonyl]benzoic acid(3-chloro-TTNCB)

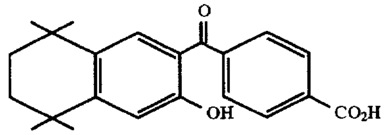 39

4-[(3-hydroxy-5,5,8,8-tetramethyl-5,6,7,8-tetrahydro-2-naphthyl)carbonyl]benzoic acid(3-hydroxy-TTNCB)

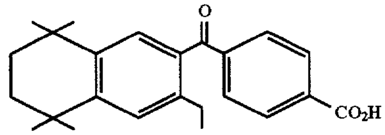 40

4-[(3-ethyl-5,5,8,8-tetramethyl-5,6,7,8-tetrahydro-2-naphthyl)carbonyl]benzoic acid(3-Et-TTNCB)

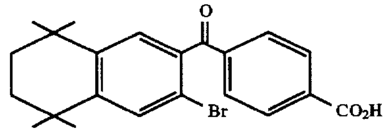 41

4-[(3-bromo-5,5,8,8-tetramethyl-5,6,7,8-tetrahydro-2-naphthyl)carbonyl]benzoic acid(3-bromo-TTNCB)

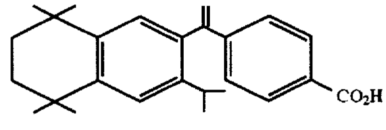 42

4-[1-(3-isopropyl-5,5,8,8-tetramethyl-5,6,7,8-tetrahydro-2-naphthyl)ethenyl]benzoic acid (3-IPr-TTNEB)

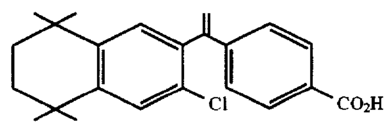 43

4-[1-(3-chloro-5,5,8,8-tetramethyl-5,6,7,8-tetrahydro-2-naphthyl)ethenyl]benzoic acid(3-chloro-TTNEB)

-continued

44

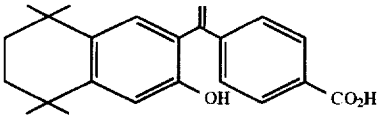

4-[1-(3-hydroxy-5,5,8,8-tetramethyl-5,6,7,8-tetrahydro-2-naphthyl)ethenyl]benzoic acid (3-hydroxy-TTNEB)

45

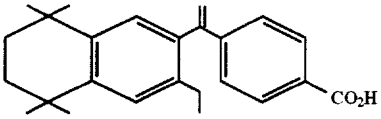

4-[1-(3-ethyl-5,5,8,8-tetramethyl-5,6,7,8-tetrhydro-2-naphthyl)ethenyl]benzoic acid(3-Et-TTNEB)

46

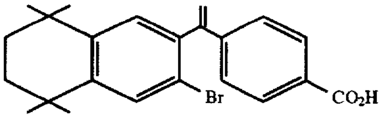

4-[1-(3-bromo-5,5,8,8-tetramethyl-5,6,7,8-tetrhydro-2-naphthyl)ethenyl]benzoic acid(3-bromo-TTNEB)

47

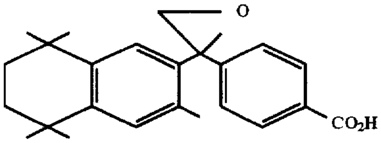

4-[1-(3,5,5,8,8-pentamethyl-5,6,7,8-tetrahydro-2-naphthyl)epoxy]benzoic acid(TPNEB)

48

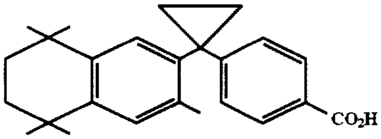

4-[1-(3,5,5,8,8-pentamethyl-5,6,7,8-tetrahydro-2-naphthyl)cyclopropyl]benzoic acid(TPNCB)

49

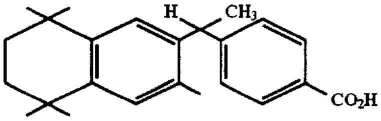

4-[1-(3,5,5,8,8-pentamethyl-5,6,7,8-tetrahydro-2-naphthyl)ethyl]benzoic acid(PTNEB)

50

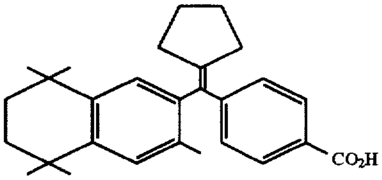

4-[1-(3,5,5,8,8-pentamethyl-5,6,7,8-tetrahydro-2-naphthyl)methylidine cyclopentane]benzoic acid (PTNCB)

51

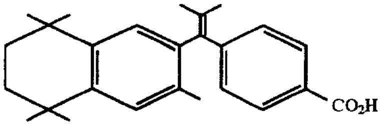

4-[1-(3,5,5,8,8-pentamethyl-5,6,7,8-tetrahydro-

-continued 2-naphthyl)-2-methyl propenyl]benzoic acid(PTNIB)

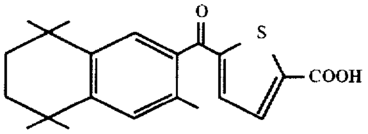

52

4-[1-(3,5,5,8,8-pentamethyl-5,6,7,8-tetrahydro-2-naphthyl)carbonyl]thiopheno-5-carboxylic acid (TTNCTC)

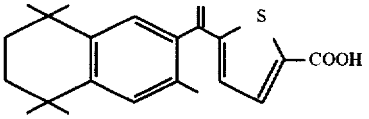

53

2-[1-(3,5,5,8,8-pentamethyl-5,6,7,8-tetrahydro-2-naphthyl)ethenyl]thiopheno-5-carboxylic acid (TTNETC)

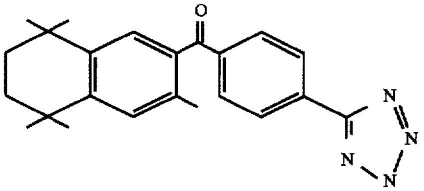

54

4-[1-(3,5,5,8,8-pentamethyl-5,6,7,8-tetrahydro-2-naphthyl)carbonyl]benzenetetrazole (3-methyl-TTNCBT)

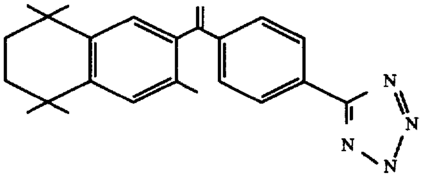

55

4-[1-(3,5,5,8,8-pentamethyl-5,6,7,8-tetrahydro-2-naphthyl)ethenyl]benzenetetrazole (3-methyl-TTNEBT)

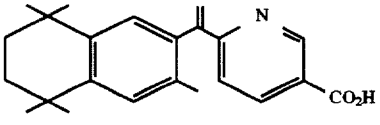

56

2-[1-(5,5,8,8-pentamethyl-5,6,7,8-tetrahydro-2-naphthyl)ethenyl]pyridine-5-carboxylic acid (TTNEP)

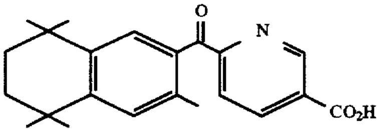

57

2-[(3,5,5,8,8-pentamethyl-5,6,7,8-tetrahydro-2-naphthyl)carbonyl]pyridine-5-carboxylic acid

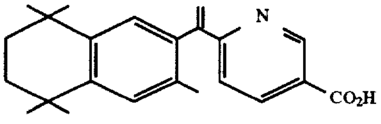

58

2-[1-(3,5,5,8,8-pentamethyl-5,6,7,8-tetrahydro-2-naphthyl)ethenyl]pyridine-5-carboxylic acid (TPNEP)

-continued

Et-58

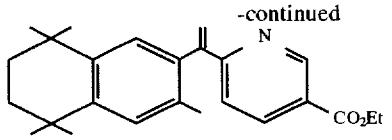

Ethyl-2-[1-(3,5,5,8,8-pentamethyl-5,6,7,8-tetrahydro-2-naphthyl)ethenyl]pyridine-5-carboxylate

59

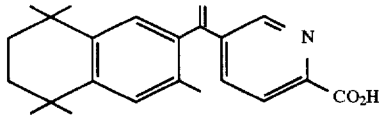

5-[(3,5,5,8,8-pentamethyl-5,6,7,8-tetrahydro-2-naphthyl)carbonyl]pyridine-7-carboxylic acid (TTNCP)

60

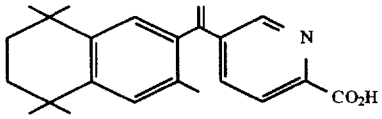

5-[1-(3,5,5,8,8-pentamethyl-5,6,7,8-tetrahydro-2-naphthyl)ethenyl]pyridine-2-carboxylic acid (TPNEPC)

61

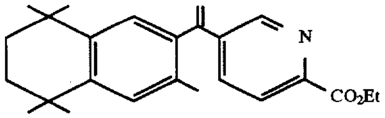

Ethyl-5-[1-(3,5,5,8,8-pentamethyl-5,6,7,8-tetrahydro-2-naphthyl)ethenyl]pyridine-2-carboxylate (3TTNEPE)

62

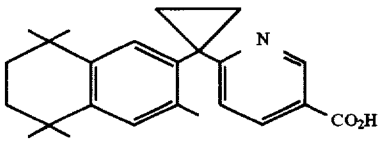

2-[1-(3,5,5,8,8-pentamethyl-5,6,7,8-tetrahydro-2-naphthyl)cyclopropyl]pyridine-5-carboxylic acid (TPNCP)

Me-62

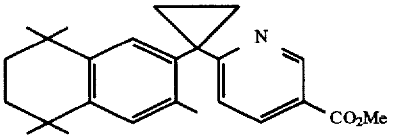

Methyl 2-[1-(3,5,5,8,8-pentamethyl-5,6,7,8-tetrahydro-2-naphthyl)cyclopropyl]pyridine-5-carboxylate Et-62

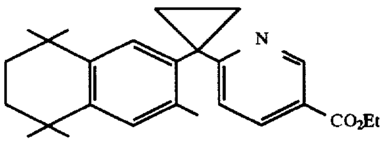

Ethyl-2-[1-(3,5,5,8,8-pentamethyl-5,6,7,8-tetrahydro-2-naphthyl)cyclopropyl]pyridine-5-carboxylate

63

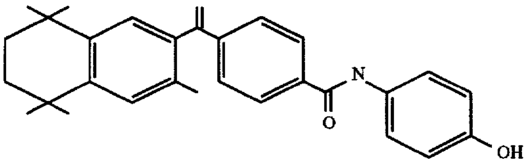

-continued

4-[1-(3,5,5,8,8-pentamethyl-5,6,7,8-tetrahydro-2-naphthyl)ethenyl]-N-(4-hydroxyphenyl)benzamide (3-Me-TTNEHBP)

64

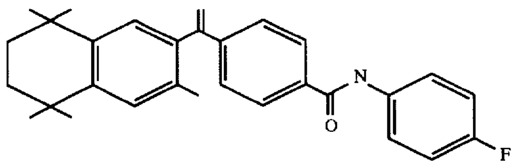

4-[1-(3,5,5,8,8-pentamethyl-5,6,7,8-tetrahydro-2-naphthyl)ethenyl]-N-(4-fluorophenyl)benzamide (3-Me-TTNEFBP)

65

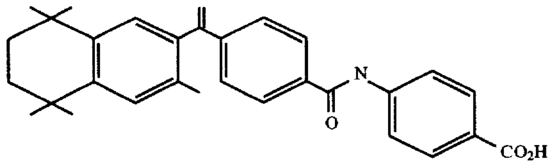

4-[1-(3,5,5,8,8-pentamethyl-5,6,7,8-tetrahydro-2-naphthyl)ethenyl]-N-(4-carboxyphenyl)benzamide (3-Me-TTNECBP)

66

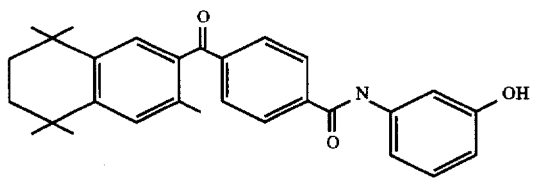

4-[(3,5,5,8,8-pentamethyl-5,6,7,8-tetrahydro-2-naphthyl)carbonyl]-N-(3-hydroxyphenyl)benzamide (3-Me-m-TTNCHBP)

67

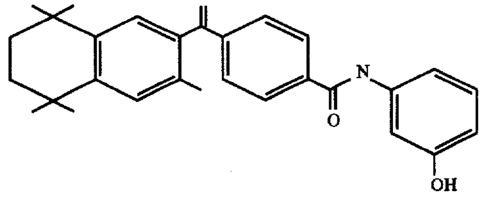

4-[1-(3,5,5,8,8-pentamethyl-5,6,7,8-tetrahydro-2-naphthyl)ethenyl]-N-(3-hydroxyphenyl)benzamide (3-Me-m-TTNEHBP)

68

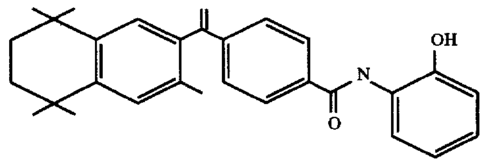

4-[1-(3,5,5,8,8-pentamethyl-5,6,7,8-tetrahydro-2-naphthyl)ethenyl]-N-(2-hydroxyphenyl)benzamide (3-Me-o-TTNCHBP)

69

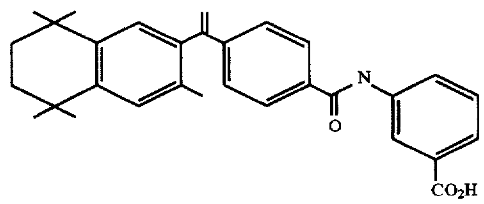

4-[1-(3,5,5,8,8-pentamethyl-5,6,7,8-tetrahydro-

-continued 2-naphthyl)ethenyl]-N-(3-carboxyphenyl)benzamide (3-Me-m-TTNECBP)

70

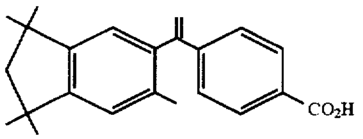

4-[1-(3,5,5,7,7-pentamethyl-2-indanyl)ethenyl]benzoic acid

71

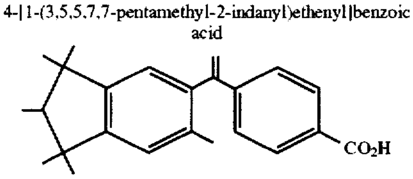

4-[1-(3,5,5,6,7,7-hexamethyl-2-indanyl)ethenyl] benzoic acid

72

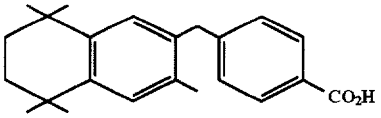

4-[1-(3,5,5,8,8-pentamethyl-5,6,7,8-tetrahydro-2-naphthyl)methyl]benzoic acid

Et-3-methyl-TTNEB

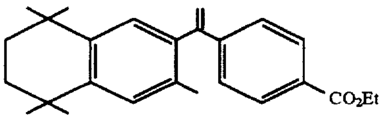

Ethyl-4-[1-(3,5,5,8,8-pentamethyl-5,6,7,8-tetrahydro-2-naphthyl)ethenyl]benzoate

73

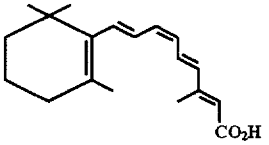

3-methyl-7-ethyl-9-(2,6,6-trimethyl-1-cyclohexen-1-yl)-2E,4E,6Z,8E-nonatetranoic acid

74

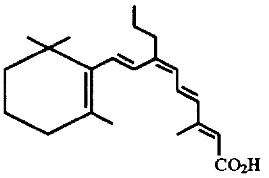

3-methyl-7-propyl-9-(2,6,6-trimethyl-1-cyclohexen-1-yl)-2E,4E,6Z,8E-nonatetranoic acid

75

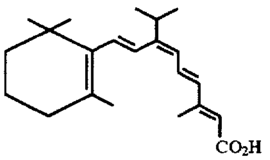

3-methyl-7-isopropyl-9-(2,6,6-trimethyl-1-cyclohexen-1-yl)-2E,4E,6Z,8E-nonatetranoic acid -continued

76

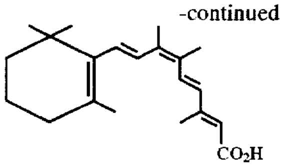

3,6,7-trimethyl-9-(2,6,6-trimethyl-1-cyclohexen-1-yl)-2E,4E,6Z,8E-nonatetranoic acid

77

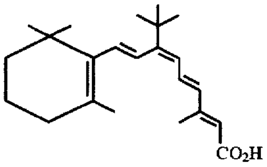

3-methyl-7-t-butyl-9-(2,6,6-trimethyl-1-cyclohexen-1-yl)-2E,4E,6Z,8E-nonatetranoic acid

95

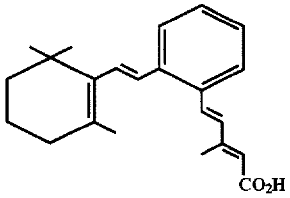

3-methyl-5-{2-[2-(2,6,6-trimethylcyclohexen-1-yl)ethenyl]phenyl}-2E,4E-pentadienoic acid

100

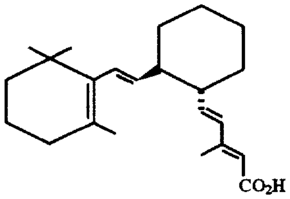

3-methyl-5-{2-[2-(2,6,6-trimethylcyclohexene-1-yl)ethenyl]cyclohexyl}-2E,4E-pentadienoic acid

104

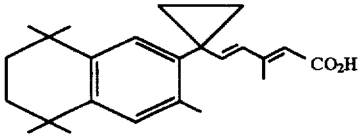

(2E,4E)-3-methyl-5-[1-(3,5,5,8,8-pentamethyl-5,6,7,8-tetrahydro-2-naphthyl)cyclopropyl]penta-2,4-dienoic acid

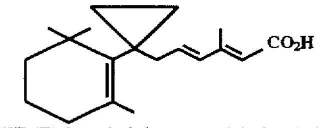

(2E,4E)-3-methyl-6-{1-[2-(2,6,6-trimethyl-1-cyclohexenyl)ethenyl]cyclopropyl}-2,4-hexadienoic acid

123

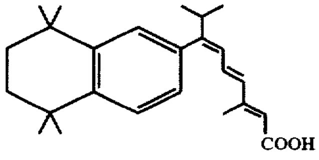

(2E,4E,6Z)-7-(5,5,8,8-tetramethyl-5,6,7,8-tetrahydro-2-naphthyl)-3,8-dimethyl-nona-2,4,6-

-continued trienoic acid

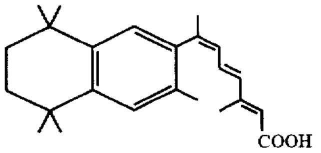

128

(2E,4E,6Z)-7-(3,5,5,8,8-pentamethyl-5,6,7,8-tetrahydro-2-naphthyl)-3-methyl-octa-2,4,6-trienoic acid In addition, thiophene, furanyl, pyridine, pyrazine, pyrazole, pyridazine, thiadiazole, and pyrrole groups function as isosteres for phenyl groups, and may be substituted for the phenyl group of the above bicyclic benzyl derivatives.

Representative derivatives of the present invention can be prepared according to the following illustrative synthetic schemes:

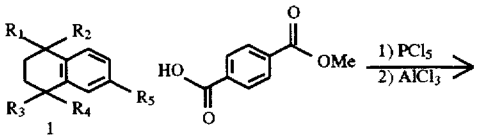

1 2

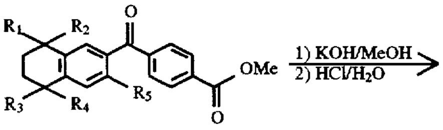

3

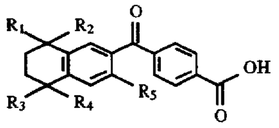

4

Compounds of structure 1 containing $R_5$=lower alkyl are prepared in accordance with U.S. Pat. No. 2,897,237. When $R_5$=Halo, OH, amino, or thio, the products are prepared by standard Friedel-Crafts reaction conditions combining the appropriate substituted benzene with 2,5-dichloro-2,5-dimethyl hexane in the presence of aluminum trichloride.

Condensation of 1 with mono-methyl terephthalate 2 was carried out by addition of $PCl_5$ to 1 and 2 in $CH_2Cl_2$ followed by addition of $AlCl_3$ at room temperature.

The resulting methyl esters 3 are hydrolyzed to the carboxylic acid 4 by refluxing in aqueous KOH-MeOH followed by acidification.

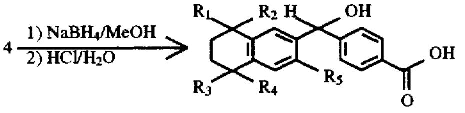

5

3
$(C_6H_5)_3P^+—CH_3Br^-$
$NaNH_2$

-continued

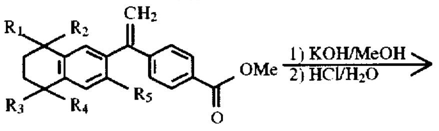

6

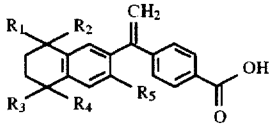

7

Treatment of ketone 4 with $NaBH_4$ afforded alcohol 5.

Treatment of the methyl ester 3 with methyltriphosphonium bromide-sodium amide in THF afforded the methano compound 6.

The carboxylic acid 7 was formed by adding KOH to methano compound 6 in MeOH, followed by acidification.

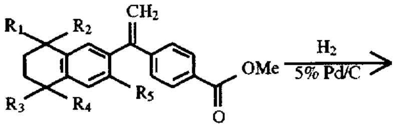

6

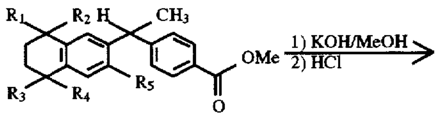

9

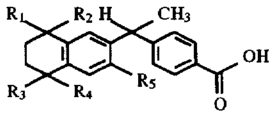

10

Treatment of the methyl ester 6 with hydrogen gas and 5% palladium over carbon in ethyl acetate yields the hydrogenated compound 9.

Treatment of compound 9 with aqueous KOH in refluxing MeOH, followed by acidification, yields the carboxylic acid compound 10.

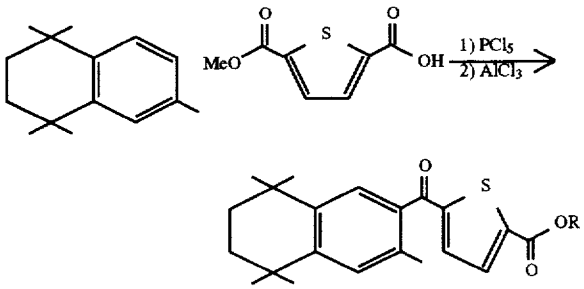

11

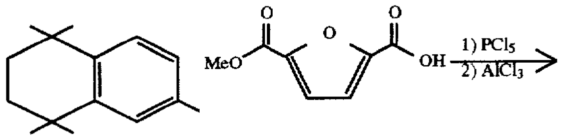

-continued

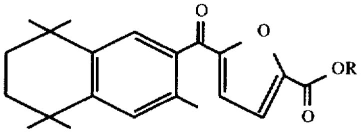

12

R = Me or H

Condensation of 1 with thiophene 2,5-mono methyl dicarboxylic acid or furanyl 2,5-mono methyl dicarboxylic acid was carried out by addition of $PCl_5$ in $CH_2Cl_2$ followed by addition of $AlCl_3$ at room temperature to give esters 11 and 12, which were hydrolyzed with KOH followed by acidification to the corresponding acids.

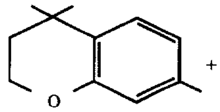

+

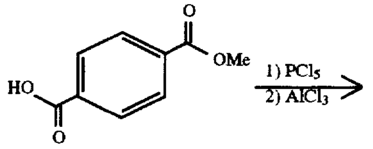

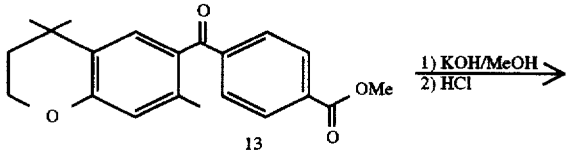

13

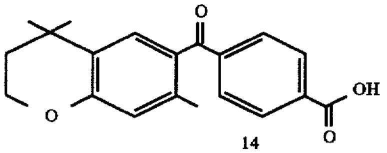

14

4,4-Dimethylchroman and 4,4-dimethyl-7-alkylchroman compounds of type 13 and 14 as well as 4,4-dimethylthiochroman, 4,4-dimethyl-7-alkylthiochroman, 4,4-dimethyl-1,2,3,4-tetrahydroquinoline, and 4,4-dimethyl-7-alkyl-1,2,3,4-tetrahydroquinoline analogs were synthesized by similar methods as compound 3, i.e., Friedel-Crafts conditions combining the appropriate dimethylchroman, dimethylthiochroman or dimethyltetrahydroquinoline with mono-methyl terephthalate acid chloride in the presence of $AlCl_3$ or $SnCl_4$, followed by base hydrolysis and acidification to give the carboxylic acid. For the synthesis of the tetrahydroquinoline analogs, it was necessary to acylate the amine before Friedel-Crafts coupling with mono-methyl terephthalate acid chloride. For the synthesis of the appropriate dimethylchromans, dimethylthiochromans and tetrahydroquinolines, see U.S. Pat. Nos. 5,053,523 and 5,023,341 and European Patent Publication No. 0284288.

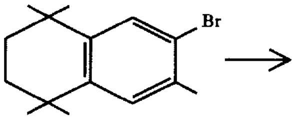

15

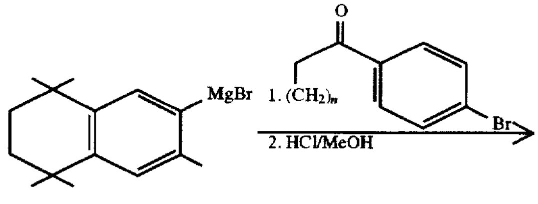

16

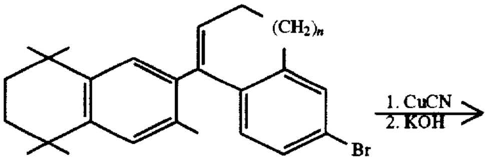

17

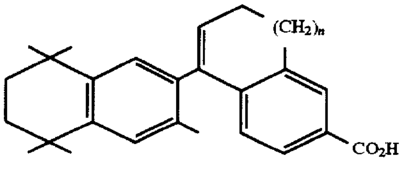

18

Compounds of the type 18 were synthesized by nucleophillic addition of the Grignard reagent 16 to bromotetralone, bromoindane, or other bicyclic ketone derivitive. Treatment of the resulting alcohol with methanolic HCl gave the intermediate 17. Displacement of the bromine with CuCN in quinoline gave the nitrile which was then hydrolyzed to the acid 18 in refluxing KOH. Bromine compound 15 was synthesized from 2,5-dichloro-2,5-dimethylhexane and 2-bromotoluene with a catalytic amount of $AlC_3$.

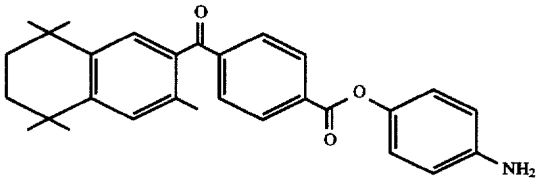

19

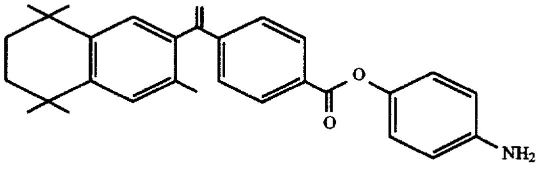

20

Treatment of compounds 3-methyl-TTNCB and 3-methyl-TTNEB with DCC, p-aminophenol, and DMAP resulted in the amino-esters 19 and 20.

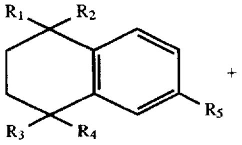

1

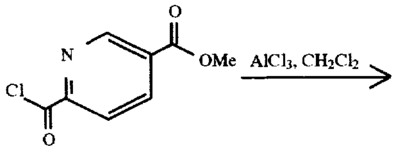

24

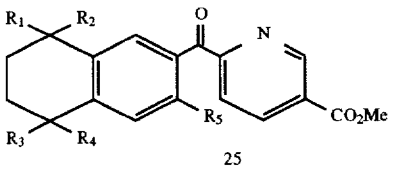

25

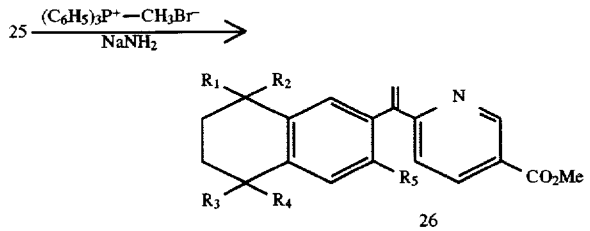

26

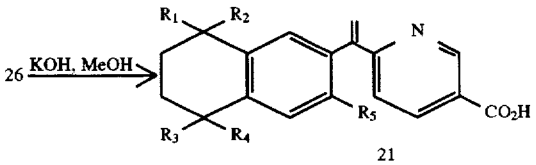

21

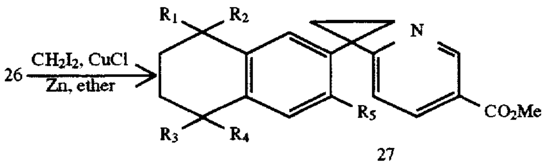

27

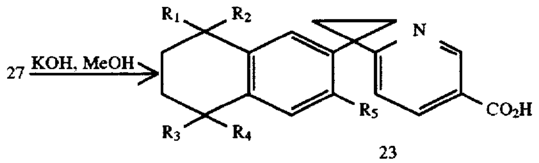

23

-continued

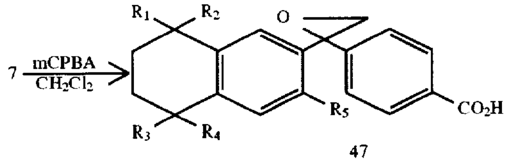

47

Representative pyridinal derivatives (compounds 21, 23, 26, and 27) may be prepared according to the illustrative synthetic schemes shown above. The synthesis of compound 21 is similar to that previously described for compound 7. Pentamethyl tetrahydronaphthalene 1, pyridinal acid chloride 24, and $AlCl_3$ are stirred in $CH_2Cl_2$ to give the ketone 25. Treatment of the ketone 25 with methyl triphosphonium bromide-sodium amide in THF afforded the ethenyl compound 26. Hydrolysis of 26 (KOH.MeOH) followed by acidification gave the acid 21. The cyclopropyl analog 23 was synthesized by treatment of the ethenyl compound 26 with $CH_2I_2$, zinc dust, CuCl in refluxing ether (Simmons-Smith reaction). Hydrolysis of the resulting cyclopropyl ester 27 was achieved with methanolic KOH followed by acidification to give compound 23. When $R_1$–$R_5$ are methyl, for example, compound 62 (TPNCP) is obtained, as shown in Example 33 below.

Other cyclopropyl derivatives such as TPNCB (compound 48) may be likewise prepared by the same method as described for analog 23: olefin 6 is treated with the Simmons-Smith reagent described above, followed by hydrolysis with methanolic-KOH and acidification (HCl) to give the desired cyclopropyl derivative. Epoxy derivatives such as TPNEB (compound 47) may be synthesized by treatment of compound 7 with m-chloroperbenzoic acid at room temperature in $CH_2Cl_2$ for several hours.

Alternatively, pyridinal analogs, such as compounds 58 (TPNEP), 60 (TPNEPC), and 61 (3TTNEPE), may be prepared by the following synthetic route.

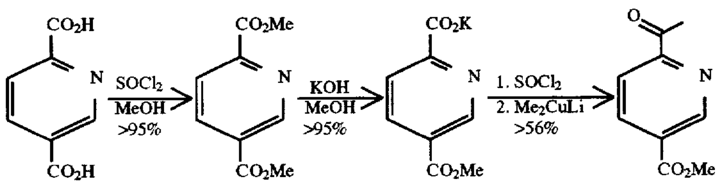

29 30 31 32

-continued
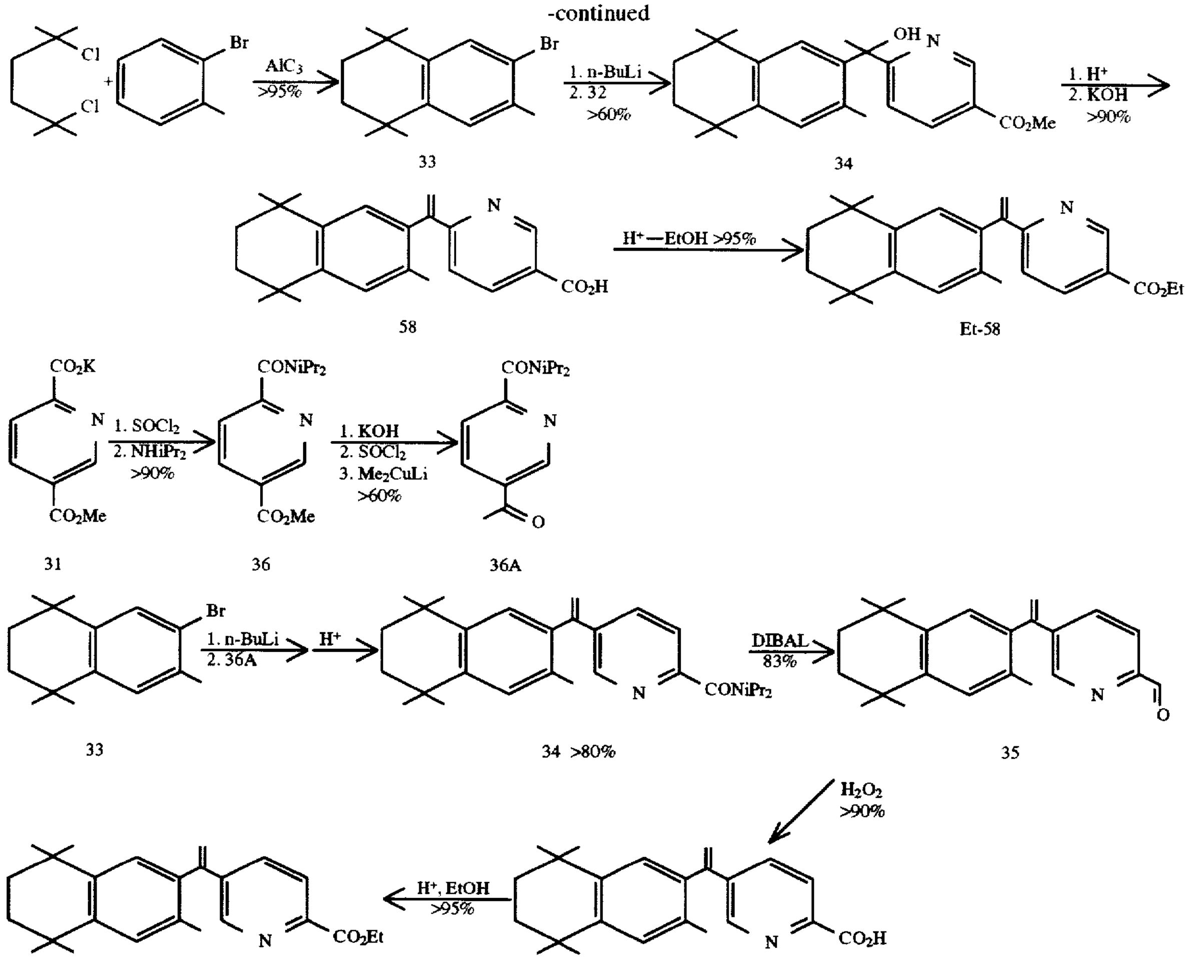
33 34
58 Et-58
31 36 36A
33 34 >80% 35
61 60
The n-alkyl cyclohexenyl nonatetranoic acid derivatives may be prepared as shown in the following synthetic schemes. The particular compound obtained (e.g., 73, 74, 75, 76, or 77) is dependent on the selection of the starting material (e.g., compounds 79, 80, 81, 82, or 83), as shown.
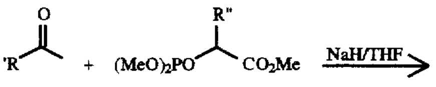
84 85
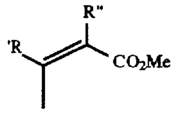
86
R' = Et, iPr, tBu, Pr, Bu etc.
R" = H, Me, iPr, Pr, tBu, Bu etc.
-continued
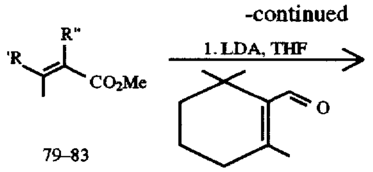
79-83
78
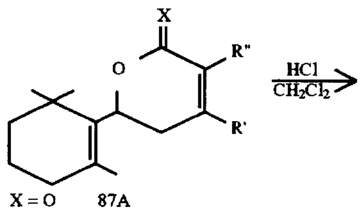
X = O 87A
X = OH, H 87B
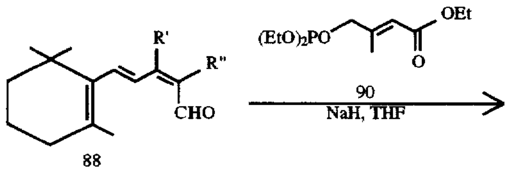
88
90

-continued

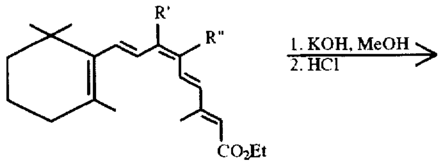

89

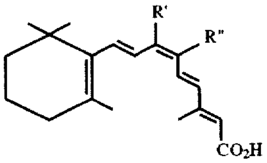

73–77

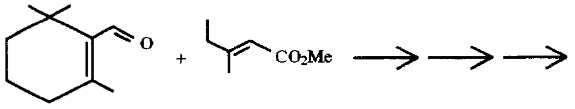

78 79

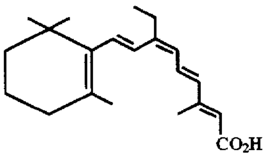

73

78 + 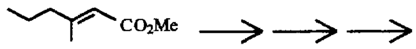

80

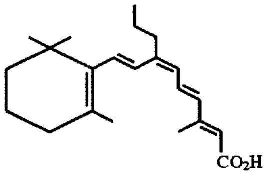

74

78 + 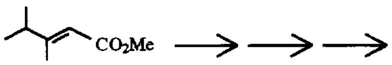

81

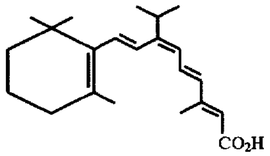

75

-continued

78 + 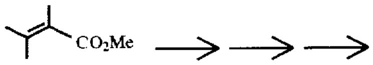

82

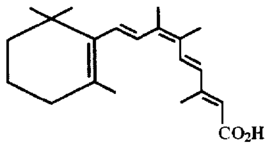

76

78 + 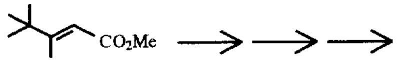

83

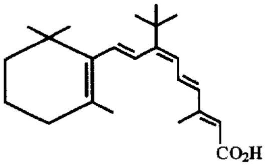

77

Synthesis of 3,7-dialkyl-9-(2,6,6-trimethyl-1-cyclohexen-1-yl)-2E,4E,6Z,8E-nonatetranoic acid and 3,6,7-trialkyl-9-(2,6,6-trimethyl-1-cyclohexen-1-yl)-2E,4E,6Z,8E-nonatetranoic acid derivatives:

Compounds of the type 73–77 were synthesized as follows: Condensation of the appropriate methyl ketone 84 and the appropriate phosphonate anion 85 gave the ester 86. Condensation of the ester 86 (or 79–83) with β-cyclocitral 78 resulted in the lactone 87A, which was treated with $LiAlH_4$ to give the lactol 87B. Treatment of the lactol 87B with HCl in methylene chloride gave the isomerially pure aldehyde 88. Condensation of the alkdehyde 88 with the anion of phosphonate 90 gave the isomerically pure ethyl-3,7-dialkyl-9-(2,6,6-trimethyl-1-cyclohexen-1-yl)-2E,4E,6Z,8E-nonatetranoate, which was hydrolized to give compounds 73–77.

Similarly, compound 95 was synthesized by condensation of the Wittig ylide 91 with benzenedialdehyde 92 to give aldehyde 93. Condensation of aldehyde 93 with the anion of phosphonate 90 gave compound 94, which was then hydrolized to the carboxylic acid 95, as shown below.

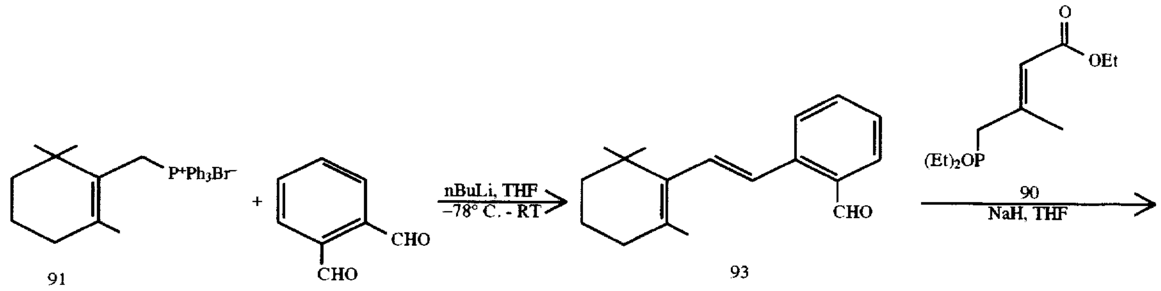
91 92 93
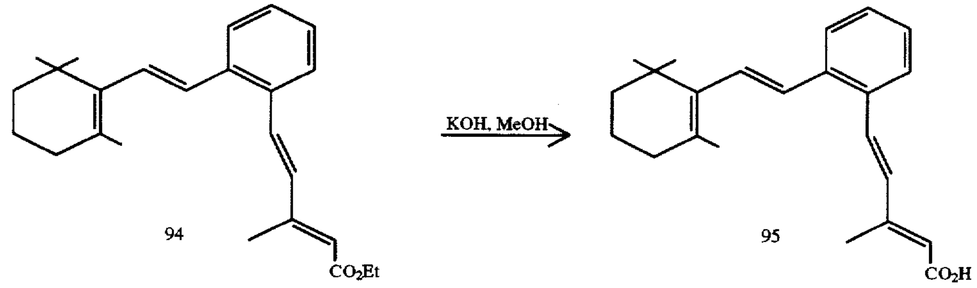
94 95
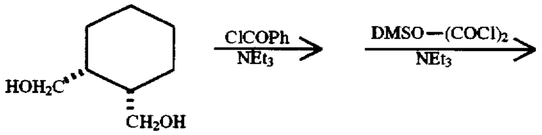
96
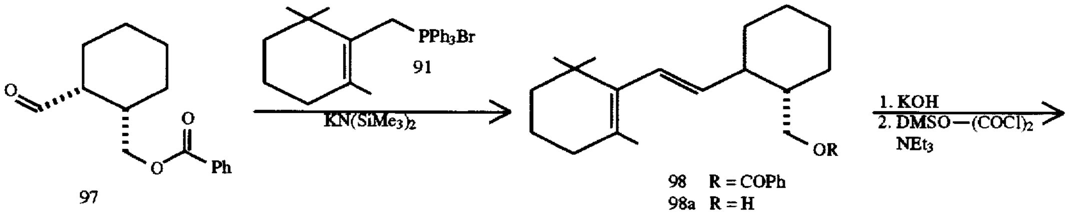
97
98 R = COPh
98a R = H
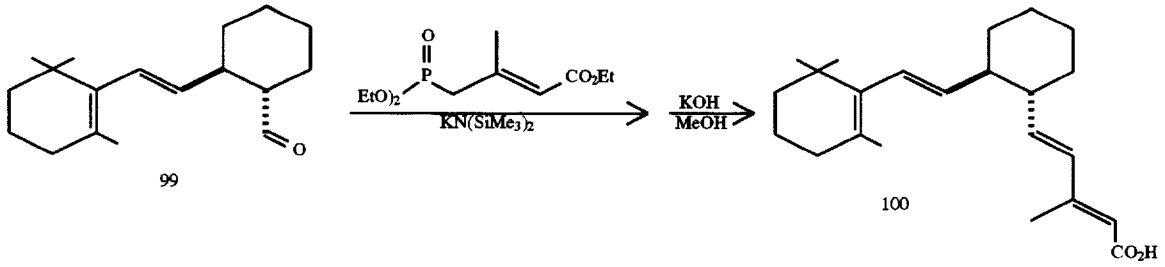
99 100
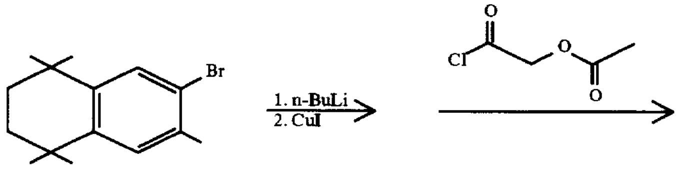
33

-continued
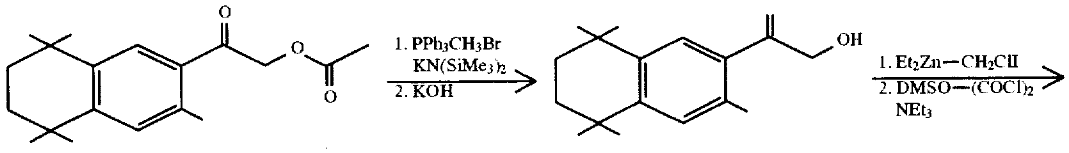
101 102
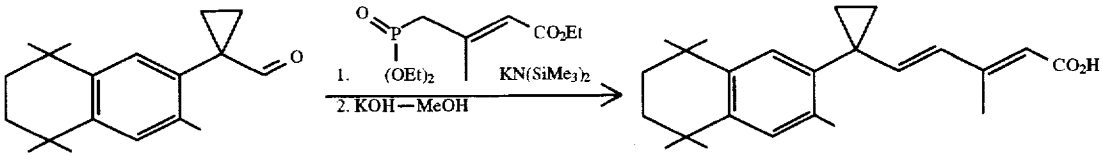
103 104
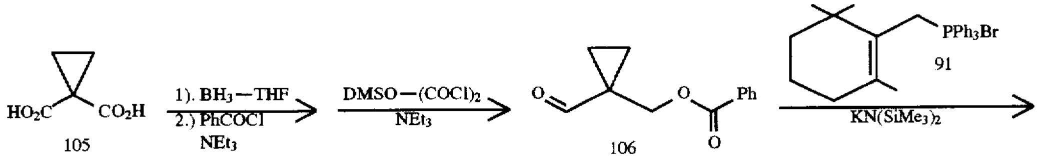
105 106
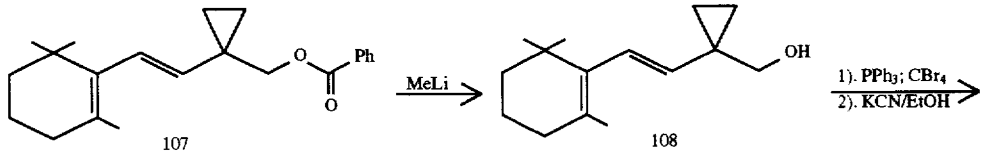
107 108
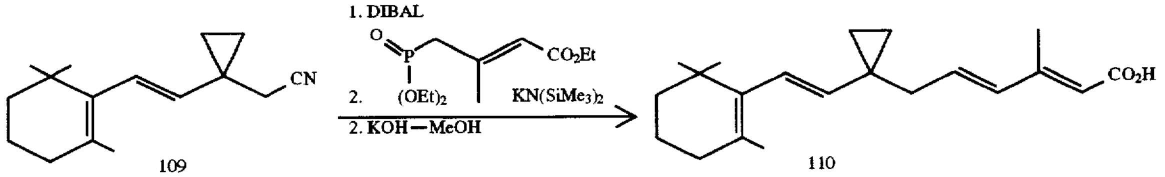
109 110
A synthesis scheme for compounds of the type 100, 104, and 110 is shown above. Further synthesis schemes for compounds of the type 123 and 128 follow below.
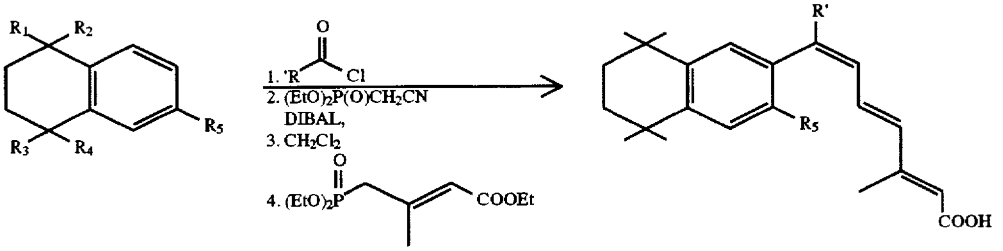
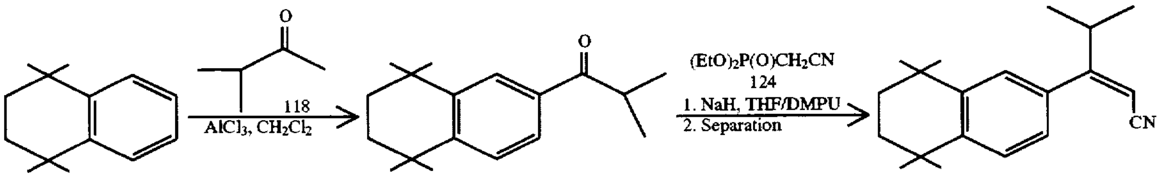
117 119 120
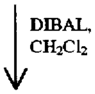

-continued

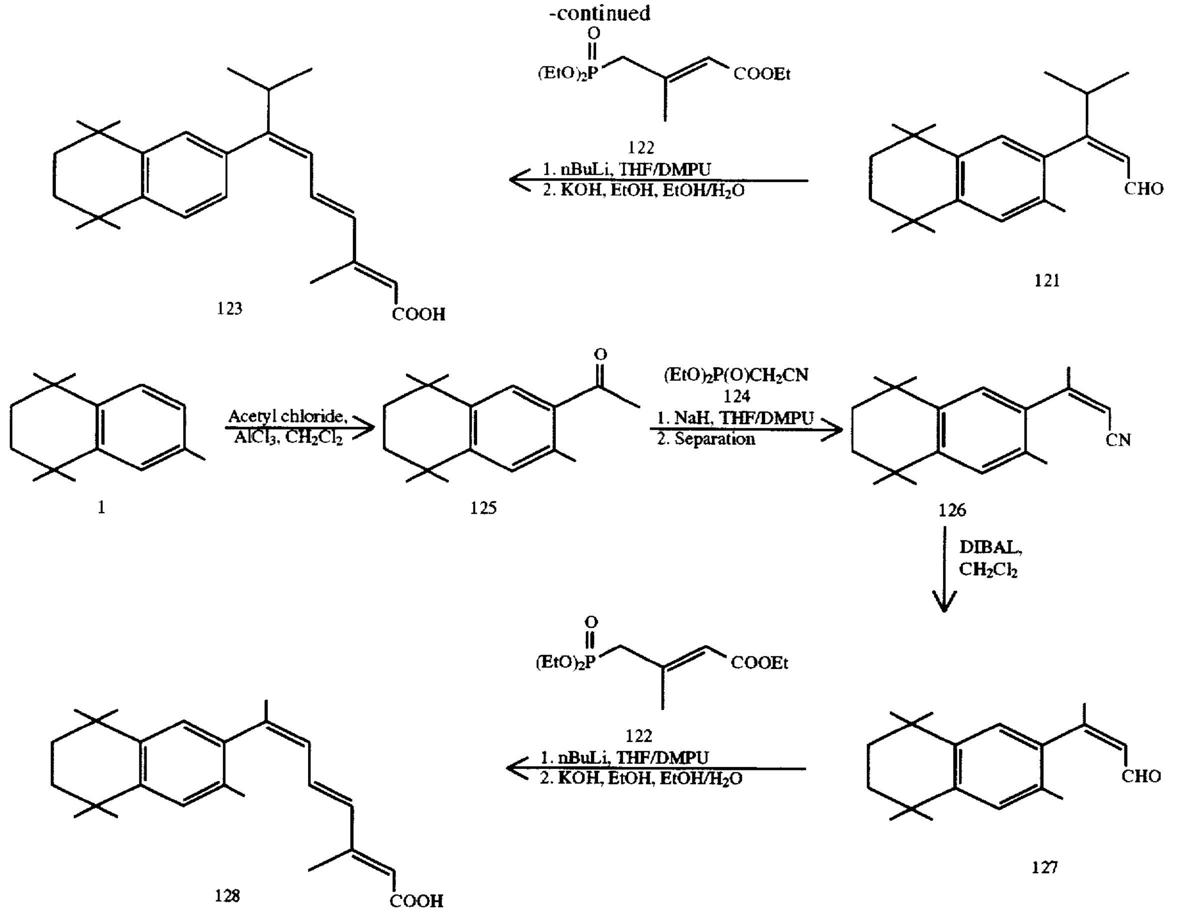

Illustrative examples for the preparation of some of the compounds according to this invention are as follows:

EXAMPLE 1

Preparation of compound 3 where $R_1$, $R_2$, $R_3$, $R_4$ and $R_5$ are methyl, R' and R" are oxo, and X=COOMe:

To 7 gm (34.7 mmol) of 1,1,4,4,6-pentamethyl-1,2,3,4-tetrahydronaphthalene and 6 gm (33.3 mmol) of mono-methyl teraphthalate in 200 mL of $CH_2Cl_2$ was added 8 g (38.8 mmol) of $PCl_5$. The reaction boiled vigorously and turned clear within 10 min. After stirring for an additional 1 h, 6 g (43.5 mmol) of $AlCl_3$ was added in 1 g portions over 15 min. and the reaction was allowed to stir overnight. The mixture was poured into 300 mL of 20% aqueous HCl and extracted with 5% EtOAc-hexanes, dried ($MgSO_4$), concentrated, and crystallized from MeOH to give ca. 6 gm (16.5 mmol) of methyl ester 3.

$^1$HNMR ($CD_3OCD_3$) δ 1.20 (s, 2($CH_3$)), 1.35 (s, 2($CH_3$)), 1.75 (s, 2($CH_2$)), 2.31 (s, $CH_3$), 3.93 (s, $COOCH_3$), 7.21 (s, Ar-CH), 7.23 (s, Ar-CH), 7.85 (d, J=8 Hz, Ar-2(CH)), 8.18 (d, J=8 Hz, Ar-2(CH)).

EXAMPLE 2

Preparation of compound 4 where $R_1$, $R_2$, $R_3$, $R_4$ and $R_5$ are methyl, R' and R" are oxo, and X=COOH (3-methyl-TTNCB):

To 6 gm (16.5 mmol) of methyl ester 3 suspended in 100 mL of MeOH was added 50 mL of 5N aqueous KOH. The mixture was heated under reflux for 1 h, cooled, acidified (20% aqueous HCl) and the organics extracted with EtOAc. After drying ($MgSO_4$), the product was concentrated and precipitated from 1:4 EtOAc-hexanes to give ca. 5 g (14.3 mmol) of acid 4.

$^1$HNMR ($CD_3OCD_3$) δ 1.20 (s, 2($CH_3$)), 1.35 (s, 2($CH_3$)), 1.75 (s, 2($CH_2$)), 2.31 (s, $CH_3$), 7.21 (s, Ar-CH), 7.23 (s, Ar-CH), 7.91 (d, J=8 Hz, Ar-2(CH)), 8.21 (d, J=8 Hz, Ar-2(CH)).

EXAMPLE 3

Preparation of compound 5 where $R_1$, $R_2$, $R_3$, $R_4$ and $R_5$ are methyl, R'=H and R"=OH, and X=COOH (3-methyl-TTNHMB):

To a 1:1 THF-MeOH solution containing 1 g (2.86 mmol) of ketone 4 was added 100 mg of $NaBH_4$. The mixture was heated to 50° C. for 10 min., cooled, acidified (20% aqueous HCl), and the organics extracted (EtOAc). After drying ($MgSO_4$), the product was concentrated and precipitated from 1:3 EtOAc-hexanes to give 550 mg (1.56 mmol) of the alcohol 5.

$^1$HNMR ($CD_3OCD_3$) δ 1.20 (s, $CH_3$)), 1.22 (s,($CH_3$)), 1.22 (s, 2($CH_3$)), 1.65 (s, 2($CH_2$)), 2.21 (s, $CH_3$), 6.00 (s, -CHOH-), 7.09 (s, Ar-CH), 7.41 (s, Ar-CH), 7.53 (d, J=8 Hz, Ar-2(CH)), 8.01 (d, J=8 Hz, Ar2(CH)).

EXAMPLE 4

Preparation of compound 6 where $R_1$, $R_2$, $R_3$, $R_4$ and $R_5$ are methyl, R' and R" are methano, and X=COOMe:

To 1 gm of methyl ester 3 (2.7 mmol) in 25 mL of dry THF was added 1.2 g (3.08 mmol) of methyltriphosphonium bromide-sodium amide. The solution was stirred at RT for 3 h or until complete by TLC (20% EtOAc-hexanes). Water was added and the organics were extracted with EtOAc, dried ($MgSO_4$), concentrated and purified by $SiO_2$ chromatography (5% EtOAc-hexanes) followed by crystallization from MeOH to give 700 mg (1.93 mmol) of methano compound 6.

$^1$HNMR ($CD_3OCD_3$) δ 1.22 (s, 2($CH_3$)), 1.30 (s, 2($CH_3$)), 1.72 (s, 2($CH_2$)), 1.95 (s, $CH_3$), 3.85 (s, $COOCH_3$), 5.29 (s,=CH), 5.92 (s, =CH), 7.19 (s, Ar-CH), 7.20 (s, Ar-CH), 7.39 (d, J=8 Hz, Ar-2(CH)), 7.96 (d, J=8 Hz, Ar-2(CH)).

EXAMPLE 5

Preparation of compound 7 where $R_1$, $R_2$, $R_3$, $R_4$ and $R_5$ are methyl, R' and R" are methano, and X=COOH (3-methyl-TTNEB):

To 500 mg of methano compound 6 (1.38 mmol) in 20 mL of MeOH was added 5 mL of 5N aqueous KOH and the suspension was refluxed for 1 h. After acidification (20% aqueous HCl) the organics were extracted (EtOAc), dried ($MgSO_4$), concentrated, and the solids recrystallized from EtOAc-hexanes 1:5 to give 350 mg (1.0 mmol) of the carboxylic acid 7.

$^1$HNMR ($CD_3OCD_3$), δ 1.22 (s, 2($CH_3$)), 1.30 (s, 2($CH_3$)), 1.72 (s, 2($CH_2$)), 1.95 (s, $CH_3$), 5.22 (s,=CH), 5.89 (s,=CH), 7.19 (s, Ar-CH), 7.20 (s, Ar-CH), 7.39 (d, J=8 Hz, Ar-2(CH)), 7.96 (d, J=8 Hz, Ar-2(CH)).

EXAMPLE 6

Preparation of compound 37 where $R_1$, $R_2$, $R_3$, $R_4$ are methyl, $R_5$ is isopropyl, R' and R" are oxo, and X=COOH (3-IPR-TTNCB):

The compound was prepared in a manner similar to that of compound 4 except that 6-isopropyl-1,1,4,4-tetramethyl-1,2,3,4-tetra-hydronaphthalene was substituted for 1,1,4,4,6-pentamethyl-1,2,3,4-tetrahydronaphthalene in examples 1 and 2. MP: 254° C.; $^1$H-NMR ($CDCl_3$) δ1.19 (d,J=7 Hz,CH($CH_3$)$_2$), 1.21 (s,2($CH_3$)), 1.33 (s,2($CH_3$)), 1.70 (s,2($CH_2$)), 3.12 (q,J=7 Hz,CH($CH_3$)$_2$), 7.14 (s,Ar-CH), 7.37 (s,Ar-CH), 7.92 (d,J=8 Hz, Ar-2(CH)), 8.18 (d,J=8 Hz, Ar-2(CH)).

EXAMPLE 7

Preparation of compound 38 where $R_1$, $R_2$, $R_3$, $R_4$ are methyl, $R_5$ is chloro, R' and R" are oxo, and X=COOH (3-chloro-TTNCB):

The compound was prepared in a manner similar to that of compound 4 except that 6-chloro-1,1,4,4-tetramethyl-1,2,3,4-tetrahydro-naphthalene was substituted for 1,1,4,4,6-pentamethyl-1,2,3,4-tetrahydronaphthalene in examples 1 and 2. MP: 254° C.; $^1$H-NMR ($CDCl_3$) δ1.26 (s,2($CH_3$)), 1.32 (s,2($CH_3$)), 1.72 (s,2($CH_2$)), 7.35 (s,Ar-CH), 7.36 (s,Ar-CH), 7.91 (d,J=8 Hz, Ar-2(CH)), 8.19 (d,J=8 Hz, Ar-2(CH)).

EXAMPLE 8

Preparation of compound 39 where $R_1$, $R_2$, $R_3$, $R_4$ are methyl, $R_5$ is hydroxy, R' and R" are oxo, and X=COOH (3-hydroxy-TTNCB):

The compound was prepared in a manner similar to that of compound 4 except that 6-hydroxy-1,1,4,4-tetramethyl-1,2,3,4-tetrahydro-naphthalene was substituted for 1,1,4,4,6-pentamethyl-1,2,3,4-tetrahydronaphthalene in examples 1 and 2. MP: 264° C.; $^1$H-NMR ($CDCl_3$) δ1.17 (s,2($CH_3$)), 1.31 (s,2($CH_3$)), 1.68 (s,2($CH_2$)), 7.02 (s,Ar-CH), 7.44 (s,Ar-CH), 7.77 (d,J=8 Hz, Ar-2(CH)), 8.27 (d,J=8 Hz, Ar-2(CH)), 11.50 (s,-OH).

EXAMPLE 9

Preparation of compound 40 where $R_1$, $R_2$, $R_3$, $R_4$ are methyl, $R_5$ is ethyl, R' and R" are oxo, and X=COOH (3-Et-TTNCB):

The compound was prepared in a manner similar to that of compound 4 except that 6-ethyl-1,1,4,4-tetramethyl-1,2,3,4-tetrahydro-naphthalene was substituted for 1,1,4,4,6-pentamethyl-1,2,3,4-tetrahydronaphthalene in examples 1 and 2. MP: 226° C.; $^1$H-NMR ($CDCl_3$) δ1.16 (t,J=7.5 Hz,-$CH_2CH_3$), 1.19 (s,2($CH_3$)), 1.32 (s,2($CH_3$)), 1.69 (s,2($CH_2$)), 2.69 (q,J=7.5 Hz, $CH_2CH_3$), 7.20 (s,Ar-CH), 7.25 (s,Ar-CH), 7.87 (brd,Ar-2(CH)), 8.20 (brd,Ar-2(CH)).

EXAMPLE 10

Preparation of compound 41 where $R_1$, $R_2$, $R_3$, $R_4$ are methyl, $R_5$ is bromo, R' and R" are oxo, and X=COOH (3-bromo-TTNCB):

The compound was prepared in a manner similar to that of compound 4 except that 6-bromo-1,1,4,4-tetramethyl-1,2,3,4-tetrahydro-naphthalene was substituted for 1,1,4,4,6-pentamethyl-1,2,3,4-tetrahydronaphthalene in examples 1 and 2. MP: 275° C.; $^1$H-NMR ($CDCl_3$) δ1.25 (s,2($CH_3$), 1.32 (s,2($CH_3$)), 1.71 (s,2($CH_2$)), 7.30 (s,Ar-CH), 7.54 (s,Ar-CH), 7.90 (d,J=8 Hz, Ar-2(CH)), 8.18 (d,J=8 Hz,Ar-2(CH)).

EXAMPLE 11

Preparation of compound 42 where $R_1$, $R_2$, $R_3$, $R_4$ are methyl, $R_5$ is isopropyl, R' and R" are methano, and X=COOH (3-IPR-TTNEB):

The compound was prepared in a manner similar to that of compound 7 except that 6-isopropyl-1,1,4,4-tetramethyl-1,2,3,4-tetrahydro-naphthalene was substituted for 1,1,4,4,6-pentamethyl-1,2,3,4-tetrahydronaphthalene in examples 1, 2, 4, and 5. MP: 252° C.; $^1$H-NMR ($CDCl_3$) δ1.05 (d,J=7 Hz, CH($CH_3$)$_2$), 1.27 (s,2($CH_3$)), 1.32 (s,2($CH_3$)), 1.70 (s,2($CH_2$)), 2.73 (q,J=7 Hz,CH($CH_3$)$_2$), 5.32 (s,=CH), 5.87 (s,=CH) 7.06 (s,Ar-CH), 7.23 (s,Ar-CH), 7.40 (d,J=8 Hz,Ar-2(CH)), 8.040 (d,J=8 Hz,Ar-2(CH)).

EXAMPLE 12

Preparation of compound 43 where $R_1$, $R_2$, $R_3$, $R_4$ are methyl, $R_5$ is chloro, R' and R" are methano, and X=COOH (3-chloro-TTNEB):

The compound was prepared in a manner similar to that of compound 7 except that 6-chloro-1,1,4,4-tetramethyl-1,2,3,4-tetrahydro-naphthalene was substituted for 1,1,4,4,6-pentamethyl-1,2,3,4-tetrahydronaphthalene in examples 1, 2, 4, and 5. MP: 233° C.; $^1$H-NMR ($CDCl_3$) δ1.28 (s,2($CH_3$)), 1.31 (s,2($CH_3$)), 1.71 (s,2($CH_2$)), 5.42 (s, =CH), 5.89 (s, =CH), 7.23 (s,Ar-CH), 7.28 (s,Ar-CH), 7.37 (d,J=8 Hz,Ar-2(CH)), 8.03 (d,J=8 Hz,Ar-2(CH)).

EXAMPLE 13

Preparation of compound 44 where $R_1$, $R_2$, $R_3$, $R_4$ are methyl, $R_5$ is hydroxy, R' and R" are methano, and X=COOH (3-hydroxy-TTNEB):

The compound was prepared in a manner similar to that of compound 7 except that 6-hydroxy-1,1,4,4-tetramethyl-1,2,3,4-tetrahydro-naphthalene was substituted for 1,1,4,4,6-pentamethyl-1,2,3,4-tetrahydronaphthalene in examples 1, 2, 4, and 5. MP: 216° C.; $^1$H-NMR ($CDCl_3$) δ1.21 (s,2($CH_3$), 1.30 (s,2($CH_3$)), 1.68 (s,2($CH_2$)), 5.54 (s,=CH), 5.94 (s,=CH), 6.86 (s,Ar-CH), 7.00 (s,Ar-CH), 7.48 (d,J=8.4 Hz, Ar-2(CH)), 8.07 (d,J=8.4 Hz, Ar-2(CH)).

EXAMPLE 14

Preparation of compound 45 where $R_1$, $R_2$, $R_3$, $R_4$ are methyl, $R_5$ is ethyl, R' and R" are methano, and X=COOH (3-Et-TTNEB):

The compound was prepared in a manner similar to that of compound 7 except that 6-ethyl-1,1,4,4-tetramethyl-1,2, 3,4-tetrahydro-naphthalene was substituted for 1,1,4,4,6-pentamethyl-1,2,3,4-tetrahydronaphthalene in examples 1, 2, 4, and 5. MP: 236° C.; $^1$H-NMR ($CDCl_3$) δ0.99 (t,J=7.6 Hz,-$CH_2CH_3$), 1.27 (s,2($CH_3$)), 1.31 (s,2($CH_3$)), 1.70 (s,2 ($CH_2$)), 2.29 (q,J=7.6 Hz,-$CH_2CH_3$), 5.34 (s,=CH), 5.83 (s,=CH), 7.08 (s,Ar-CH), 7.12 (s,Ar-CH), 7.38 (d,J=8 Hz, Ar2(CH)), 8.00 (d,J=8 Hz, Ar-2(CH)).

EXAMPLE 15

Preparation of compound 46 where $R_1$, $R_2$, $R_3$, $R_4$ are methyl, $R_5$ is bromo, R' and R" are methano, and X=COOH (3-bromo-TTNEB):

The compound was prepared in a manner similar to that of compound 7 except that 6-bromo-1,1,4,4-tetramethyl-1,2,3,4-tetrahydro-naphthalene was substituted for 1,1,4,4,6-pentamethyl-1,2,3,4-tetrahydronaphthalene in examples 1, 2, 4, and 5. MP: 235° C.; $^1$H-NMR ($CDCl_3$) δ1.27 (s,2($CH_3$)), 1.31 (s,2($CH_3$)), 1.71 (s,$CH_3$), 5.40 (s,=CH), 5.90 (s,=CH), 7.26 (s,Ar-CH), 7.36 (s,Ar-CH), 7.43 (d,J=8 Hz,Ar-2(CH)), 8.04 (d,J=8 Hz,Ar-2(CH)).

EXAMPLE 16

Preparation of compound 47 where $R_1$, $R_2$, $R_3$, $R_4$, $R_5$ are methyl, R' and R" taken together are $CH_2$-O (epoxide), and X=COOH (TPNEB):

The compound was prepared from compound 6 where $R_1$, $R_2$, $R_3$, $R_4$, $R_5$ are methyl. To 1 g (2.76 mmol) of olefin 6 in 5 mL of $CH_2Cl_2$ was added 600 mg (3.46 mmol) of mCPBA and the reaction was stirred at room temperature for 2 h. Water was added followed by extraction of the organics with ether. The ether layer was washed with water, 1N $Na_2CO_3$, brine and dried ($MgSO_4$), filtered and concentrated. Crystallization from MeOH gave the desired epoxidemethyl ester. The methyl ester was hydrolized in refluxing methanolic KOH followed by acidification (1N HCl) to give the crude epoxide-acid 47 which was purified by crystallization from EtOAc-hex to give 600 mg (1.64 mmol) of a white powder (59% yield). MP: 168° C.; $^1$H-NMR ($CDCl_3$) δ1.26 (s,$CH_3$), 1.27 (s,$CH_3$), 1.30 (s,$CH_3$), 1.31 (s,$CH_3$), 1.69 (s,(2$CH_2$)), 2.14 (s,$CH_3$), 3.15 (d,J=5.6 Hz,CH-O), 3.41 (d,J=5.6 Hz,CH-O), 7.09 (s,Ar-CH), 7.28 (d,J=8.3 Hz, Ar-2 (CH)), 7.32 (s,Ar-CH), 8.01 (d,J=8.3 Hz,Ar-2(CH)).

EXAMPLE 17

Preparation of compound 48 where $R_1$, $R_2$, $R_3$, $R_4$, $R_5$ are methyl, R' and R" taken together are $CH_2$-$CH_2$ (cyclopropyl), and X=COOH (TPNCB):

The compound was prepared from compound 6 where $R_1$, $R_2$, $R_3$, $R_4$, $R_5$ are methyl. To a dry 100 mL three necked round bottom flask fitted with a reflux condensor, dropping funnel, and magnetic stir bar was added 722 mg (11.65 mmol) of zinc dust, 109 mg (1.105 mmol) of cuprous chloride (CuCl), 7.5 mL of dry THF, and 1.48 g (5.52 mmol) of diiodomethane. To the addition funnel is added 1 g (2.76 mmol) of compound 6 in 5 mL of dry THF. The flask is heated to 80° C., followed by dropwise addition of 6. After the addition of 6 was complete, the reaction was allowed to reflux for 30 h or until completion, followed by dilution with 50 mL of ether and 20 mL of saturated aqueous ammonium chloride solution. The organic layer was washed with 10% NaOH (3×20 mL), brine and dried over anhydrous $MgSO_4$. The product was concentrated and purified by preparative TLC (2% EtOAc-hexane) to give 220 mg (0.59 mmol) of the methyl ester of 48. Hydrolysis of the methyl ester with refluxing methanolic KOH, followed by acidification (1N HCl), gave 150 mg (0.41 mmol) of the desired compound 48 after crystallization from EtOAc-hexane (15% yield). MP: 244° C.; $^1$H-NMR ($CDCl_3$) δ1.28 (s,4 ($CH_3$)), 1.39 (s,$CH_2$-$CH_2$), 1.69 (s,2($CH_2$)), 2.12 (s,$CH_3$), 6.98 (d,J=8.4 Hz,Ar-2(CH)), 7.06 (s,Ar-CH), 7.29 (s,Ar-CH), 7.91 (d,J=8.4 Hz,Ar-2(CH)).

EXAMPLE 18

Preparation of compound 49 where $R_1$, $R_2$, $R_3$, $R_4$, $R_5$ are methyl, R'=H and R"=$CH_3$, and X=COOH (PTNEB):

The compound was prepared from compound 7 where $R_1$, $R_2$, $R_3$, $R_4$, $R_5$ are methyl. To 1 g (2.87 mmol) of compound 7 in 25 mL of EtOAc was added 10 mg of 10% Pd/C. The mixture was degassed under vacuum followed by addition of $H_2$, and allowed to stir under $H_2$ for 2 h. The reaction was filtered through celite and the product crystallized from EtOAc-hexane to give 750 mg (2.14 mmol) of the desired product 49 (75% yield). MP: 208° C.; $^1$H-NMR ($CDCl_3$) δ1.24 (s,$CH_3$), 1.25 (s,$CH_3$), 1.26 (s,$CH_3$), 1.29 (s,$CH_3$), 1.61 (d,J=7.2 Hz,$CH_3$), 1.67 (s,2($CH_2$)), 2.12 (s,$CH_3$), 4.30 (q,J=7.2 Hz, CH), 7.02 (s,Ar-CH), 7.20 (s,Ar-CH), 7.24 (d,J=8.4 Hz, Ar-2(CH)), 7.99 (d,J=8.4 Hz,Ar-2(CH)).

EXAMPLE 19

Preparation of compound 50 where $R_1$, $R_2$, $R_3$, $R_4$, $R_5$ are methyl, R' and R"=methylidenecyclopentane, and X=COOH (PTNCB):

The compound was prepared from compound 4 where $R_1$, $R_2$, $R_3$, $R_4$, $R_5$ are methyl. To 1 g (2.87 mmol) of 4 in 25 mL of THF at 0° C. was added 8.6 mL of a 1M cyclopentenyl magnesium chloride solution (8.6 mmol). After stirring for 30 m, water was added and acidified with 5N HCl. The acidified mixture was heated for 5m, cooled, and the organic product extracted with EtOAc. The EtoAc layer was washed with water and brine, dried ($MgSO_4$), filtered, and concentrated to give the crude product. Crystallization from EtOAc-hexane gave 340 mg (0.85 mmol) of 50 as a white powder (30% yield). MP: 201° C.; $^1$H-NMR ($CDCl_3$) δ1.27 (s,4($CH_3$)), 1.64 (br t,$CH_2$), 1.68 (s,2($CH_2$)), 1.70 (br t,$CH_2$), 1.97 (s,$CH_3$), 2.15 (br t,$CH_2$), 2.56 (br t,$CH_2$), 7.04 (s,Ar-CH), 7.05 (s,Ar-CH), 7.29 (d,J=8 Hz,Ar-2(CH)), 7.97 (d,J=8 Hz,Ar-2(CH)).

EXAMPLE 20

Preparation of compound 51 where $R_1$, $R_2$, $R_3$, $R_4$, $R_5$ are methyl, R' and R"=isopropylidene, and X=COOH (PTNIB):

The compound was prepared from compound 4 where $R_1$, $R_2$, $R_3$, $R_4$, $R_5$ are methyl. To 1 g (2.87 mmol) of 4 in 25 mL of THF at 0° C. was added 8.6 mL of a 1M isopropyl magnesium chloride solution (8.6 mmol). After stirring for 30 m, water was added and acidified with 5N HCl. The acidified mixture was heated for 5m, cooled, and the organic product extracted with EtOAc. The EtOAc layer was washed with water and brine, dried ($MgSO_4$), filtered, and concentrated to give the crude isopropylidene product. Crystallization from EtOAc-hexane gave 550 mg (1.46 mmol) of 51 as a white powder (51% yield). MP: 297° C.; $^1$H-NMR ($CDCl_3$) δ1.25 (br s,4($CH_3$)), 1.64 (s,=$CCH_3$), 1.66 (s,=$CCH_3$) 1.87 (s,2($CH_2$)), 1.96 (s,$CH_3$), 7.00 (s,Ar-CH), 7.03 (s,Ar-CH), 7.25 (d,J=8 Hz,Ar-2(CH)), 7.97 (d,J=8 Hz,Ar-2 (CH)).

EXAMPLE 21

Preparation of compound 52 where $R_1$, $R_2$, $R_3$, $R_4$, $R_5$ are methyl, R' and R"=oxo, Z=S, and X=COOH (TTNCTC):

To 1 g (4.9 mmol) of 1,1,4,4,6-pentamethyl-1,2,3,4-tetrahydro-naphthalene and 1 g (4.9 mmol) of mono methyl thiophene carboxylic acid chloride in 25 mL of $CH_2Cl_2$ was added 1 g (7.5 mmol) of $AlCl_3$. The reaction was heated to reflux for 15 m followed by cooling and addition of 20% aqueous HCl. The product was extracted with EtOAc, washed ($H_2O$, brine), dried ($MgSO_4$), filtered, concentrated, and purified by crystallization from MeOH to give 450 mg (1.21 mmol) of the methyl ester of 52 (25% yield). The methyl ester was hydrolized in methanolic KOH followed by acidification (20% HCl) extraction with EtOAc, washed ($H_2O$, brine), dried ($MgSO_4$), filtered, concentrated, and purified by crystallization from EtOAc-hexane to give 375 mg (1.05 mmol) of 52 (87% yield). MP: 206° C.; $^1$H-NMR ($CDCl_3$) δ1.26 (s,2($CH_3$)), 1.31 (s,2($CH_3$)), 1.71 (s,2($CH_2$)), 2.38 (s,$CH_3$), 7.21 (s,Ar-CH), 7.44 (s,Ar-CH), 7.48 (d,J=4 Hz, Thio Ar-CH), 7.85 (d,J=4 Hz,Thio Ar-CH).

EXAMPLE 22

Preparation of compound 53 where $R_1$, $R_2$, $R_3$, $R_4$, $R_5$ are methyl, R' and R"=methano, Z=S, and X=COOH (TTNETC):

Compound 53 was prepared from the methyl ester of 52 in a manner similar to examples 4 and 5. MP: 200° C.; $^1$H-NMR ($CDCl_3$) δ1.26 (s,2($CH_3$)), 1.30 (s,2($CH_3$)), 1.69 (s,2($CH_2$)), 2.10 (s,$CH_3$), 5.21 (s,=CH), 5.88 (s,=CH), 6.76 (d,J=4 Hz,Thio Ar-CH), 7.11 (s, ArCH), 7.23 (s,Ar-CH), 7.68 (d,J=4 Hz,Thio Ar-CH).

EXAMPLE 23

Preparation of compound 54 where $R_1$, $R_2$, $R_3$, $R_4$, $R_5$ are methyl, R' and R"=oxo, and X=tetrazole (3-methyl-TTNCBT):

To 500 mg (1.51 mmol) of 4-((3,5,5,8,8-pentamethyl-5,6,7,8-tetrahydro-2-naphthyl) carbonyl]benzonitrile (synthesized by $AlCl_3$ catalyzed condensation of 1,1,4,4,6-pentamethyl-1,2,3,4-tetra hydronaphthalene with 4-cyanobenzoic acid chloride in $CH_2Cl_2$) in toluene was added 342 mg (1.66 mmol) of trimethyl tin azide. The mixture was refluxed for 23 h and cooled to give 537 mg (1.44 mmol) of the desired tetrazole 54 as a white precipitate (96% yield). LRMS: 374.15; $^1$H-NMR ($CD_3SOCD_3$) δ1.19 (s,2($CH_3$)), 1.32 (s,2($CH_3$)), 1.70 (s,2($CH_2$)), 2.25 (s, $CH_3$), 3.19 (s,N-H), 7.30 (s,Ar-CH), 7.32 (s,Ar-CH), 7.90 (d,J=8 Hz,Ar-2(CH)), 8.20 (d,J=8 Hz,Ar-2(CH)).

EXAMPLE 24

Preparation of compound 55 where $R_1$, $R_2$, $R_3$, $R_4$, $R_5$ are methyl, R' and R"=methano, and X=tetrazole (3-methyl-TTNEBT):

To 500 mg (1.52 mmol) of 4-[1-(3,5,5,8,8-pentamethyl-5,6,7,8-tetrahydro-2-naphthyl)ethenyl]benzonitrile (synthesized by $AlCl_3$ catalyzed condensation of 1,1,4,4,6-pentamethyl-1,2,3,4-tetrahydronaphthalene with 4-cyanobenzoic acid chloride in $CH_2Cl_2$ followed by treatment of the ketone with $CH_3PPh_3Br$-$NaNH_2$) in toluene was added 342 mg (1.67 mmol) of trimethyl tin azide. The mixture was refluxed for 23 h and cooled to give 535 mg (1.44 mmol) of the desired tetrazole 55 as a white precipitate (95% yield). LRMS: 372.25; $^1$H-NMR ($CD_3SOCD_3$) δ1.21 (s,2($CH_3$)), 1.24 (s,2($CH_3$)), 1.68 (s,2($CH_2$)), 1.92 (s,$CH_3$), 2.55 (s,N-H), 5.27 (=CH), 5.97 (s,=CH), 7.10 (s,Ar-CH), 7.18 (s,Ar-CH), 7.47 (d,J=8 Hz,Ar-2(CH)), 8.00 (d,J=8 Hz,Ar-2(CH)).

EXAMPLE 25

Preparation of compound 25 where $R_1$, $R_2$, $R_3$, $R_4$ are methyl, R' and R"=oxo, and X=COOMe:

The compound was prepared in a manner similar to that of compound 4 except that 1,1,4,4-tetramethyl-1,2,3,4-tetrahydronaphthalene was substituted for 1,1,4,4,6-pentamethyl-1,2,3,4-tetrahydronaphthalene and 4-methyl ester pyridinic 2-acid chloride was substituted for mono-methyl terephthalic acid chloride (see examples 1 and 2).

EXAMPLE 26

Preparation of compound 56 where $R_1$, $R_2$, $R_3$, $R_4$ are methyl, R' and R"=methano, and X=COOH (TTNEP):

Compound 25 was treated with $CH_3PPh_3Br$-$NaNH_2$ as in example #4. Hydrolysis of the resulting olefinic methyl ester with methanolic KOH, followed by acidification (20% HCl) and crystallization from EtOAc-hexane gave compound 56. MP: 173° C.; $^1$H-NMR ($CDCl_3$) δ1.26 (s,($CH_3$)), 1.27 (s,$CH_3$), 1.30 (s,2($CH_3$)), 1.70 (s,($CH_2$)), 5.70 (s,=CH), 6.10 (s,=CH), 7.08 (d,J=8 Hz,Pyr-CH), 7.27 (s,Ar-CH), 7.19 (d,J=8 Hz,Ar-CH), 7.39 (d,J=8 Hz,Ar-CH), 8.28 (d,J=8 Hz,Pyr-CH), 9.31 (s,Pyr-CH).

EXAMPLE 27

Preparation of compound 57 where $R_1$, $R_2$, $R_3$, $R_4$, $R_5$ are methyl, R' and R"=oxo, and X=COOH:

Compound 57 was prepared in a manner similar to that of compound 6 (example #4) except that 4-methylester-pyridinic-2-acid chloride was substituted for mono-methyl terephthalic acid chloride (see examples 1 and 2). The resulting methyl ester was hydrolyzed as in example #5 to give compound 57. $^1$H-NMR ($CDCl_3$) δ1.22 (s,2($CH_3$)), 1.30 (s, 2($CH_3$)), 1.69 (s,2($CH_2$)), 2.40 (s,$CH_3$), 7.22 (s,Ar-CH), 7.43 (s,Ar-CH), 8.13 (d,J=8.0 Hz,Pyr-CH), 8.54 (d,J=8 Hz,Pyr-CH), 9.34 (s,Pyr-CH).

EXAMPLE 28

Preparation of compound 58 where $R_1$, $R_2$, $R_3$, $R_4$, $R_5$ are methyl, R' and R"=methanol and X=COOH (TPNEP):

The methyl ester from example #26 was treated with $CH_3PPh_3Br$-$NaNH_2$ as in example #4 followed by hydrolysis with methanolic KOH at reflux for 1 h and acidification with 20% aqueous HCl and crystallization from EtOAc-hexane to give compound 58. MP: 235° C.; $^1$H-NMR ($CDCl_3$) δ1.27 (s,2($CH_2$)), 1.31 (s,2($CH_3$)), 1.70 (s,2($CH_2$)), 2.00 (s,$CH_3$), 5.55 (s,=CH), 6.57 (s,=CH), 7.06 (d,J=8.3 Hz,Pyr-CH), 7.12 (s;Ar-CH), 7.14 (s,Ar-CH), 8.20 (d,J=8.1 Hz,Pyr-CH), 9.29 (s,Pyr-CH).

EXAMPLE 29

Preparation of methyl 2-acetyl-5-pyridinecarboxylate 32:

To a slurry of the 2,5-pyridinedicarboxylic acid 29 (34 g, 0.2 mol) in 120 mL of methanol at 0° C. was added dropwise 15 mL of thionyl chloride and the resulting slurry was warmed up to room temperature, giving rise to a clear solution. The mixture then was heated at reflux for 12 h and to afford a yellow slurry. Filtration of the reaction mixture provided dimethyl-2,5-pyridinedicarboxylate 30 in quantitative yield as a yellow crystalline solid.

The pyridinedicarboxylate 30 (19.5 g, 0.1 mol) was treated with solid KOH (6.51 g, 0.1 mol) in 300 mL of methanol at room temperature for 2 h, giving rise to a thick pale white suspension, which was filtered and dried to provide the mono-potassium pyridinecarboxylate 3 in quantitative yield.

The crude mono-pyridinecarboxylate 31 (880 mg, 4 mmol) was treated with 3 mL of thionyl chloride at reflux for 2 h and the excess $SOCl_2$ was removed by the usual method. To the crude acid chloride in 8 mL of THF at −78° C. was added slowly a freshly prepared 1.0M ether solution (5.5 mL, 5.5 mmol) $Me_2CuLi$. The resulting dark slurry was allowed to stir at −78° C. for 60 min. and then was quenched with 2% HCl. Standard work-up and chromatography of the crude mixture afforded methyl-2-acetyl-5-pyridinecarboxylate 32 in over 56% yield as a yellow solid.

EXAMPLE 30

Preparation of compound 58 (TPNEP) (by an alternate scheme than in Example 28) and of corresponding ester Et-58 where $R_1$, $R_2$, $R_3$, $R_4$, $R_5$ are methyl, R' and R" are methano, and =COOH:

A solution of 2-bromotoluene (8.5 g, 50 mmol) and 2,2-dichloro-2,2-dimethylhexane (9.15 g, 50 mmol) in 100 mL of dichloroethane was treated with aluminum trichloride (0.66 g, 5 mmol). The resulting dark brown solution was allowed to stir at room temperature for 30 min. and was then quenched with ice. Removal of solvent and recrystallization from methanol afforded 2-bromo-3,5,5,8,8-pentamethyl-5,6,7,8-tetrahydronaphthlalene 95% yield as a white solid. A THF (4 mL) solution containing the bromocompound 33 (141 mg, 0.5 mmol) at −78° C. was treated with a 1.6M hexane solution (0.4 mL, 0.6 mmol) of n-BuLi, and the resulting mixture was then cannulated to a THF (2 mL) solution of the 2-acetyl-5-pyridinecarboxylate 32 (72 mg, 0.4 mmol) at −78° C. The mixture was allowed to stir at −78° C. for 60 min. and was quenched with 2% HCl. Removal of the solvent and chromatography of the crude mixture provided the intermediate 34, which was then treated with 5% HCl at reflux followed by KOH-MeOH at 70° C. for 30 min. Standard work-up and chromatography of the crude mixture provided 2-|1-(3,5,5,8,8-pentamethyl-5,6,7,8-tetrahydro-2 naphthyl)ethenyl|pyridine-5-carboxylic acid 58 in over 50% yield as a white solid. $^1$H-NMR ($CDCl_3$) δ1.27 (s,2($CH_3$)), 1.31 (s,2($CH_3$)), 1.70 (s,2($CH_2$)), 2.00 (s, $CH_3$), 5.56 (s,=CH), 6.55 (s,=CH), 7.08 (d,J=8.3 Hz, Pyr-CH), 7.12 (s,Ar-CH), 7.15 (s,Ar-CH), 8.23 (d,J=8.3 Hz,Pyr-CH) and 9.32 (s,Pyr-CH).

Treatment of the pyridinecarboxylic acid 58 (15 mg, 0.004 mmol) with one drop of $SOCl_2$ in 5 mL of ethanol at reflux for 60 m, followed by a flash chromatography, gave rise to a quantitative yield of the ethyl ester Et-58 as a white solid. $^1$H-NMR ($CDCl_3$) δ1.27 (s,2($CH_3$)), 1.31 (s,2($CH_3$)), 1.40 (t,J=7.1 Hz, —$CH_2CH_3$), 1.70 (s,2($CH_2$)), 1.99 (s,$CH_3$), 4.40 (q,J=7.1 Hz, —$CH_2CH_3$), 5.51 (s,=CH), 6.53 (s,=CH), 7.01 (d, J=8.0 Hz,Pyr-CH), 7.12 (s,Ar-CH), 7.14 (s,Ar-CH), 8.15 (d,J=8.0 Hz,Pyr-CH) and 9.23 (s,Pyr-CH).

EXAMPLE 31

Preparation of 3-acetyl-2-pyridinecarboxylic acid N,N-diisopropylamide 36a:

The mono-potassium pyridinecarboxylate 31 (1.1 g, 5 mmol) was treated with $SOCl_2$ (5 mL, excess) at 70° C. for 2 h and the excess thionyl chloride was removed to give a yellowish solid. To a solution of diisopropylamine (1 g, 10 mmol) in 10 mL of methylene chloride at 0° C. was added the $CH_2Cl_2$ solution (10 mL) of the above acid chloride. The resulting slurry was allowed to stir at room temperature for 3 h and was filtered from the ammonium salts. Removal of solvent and chromatography of the crude residue afforded the product 36a in 90% yield as a white solid.

EXAMPLE 32

Preparation of compounds 60 (TPNEPC) and 61 (3TTNEPE):

2-Bromo-3,5,5,8,8-pentamethyl-5,6,7,8-tetrahydronaphthalene 33 (620 mg, 2.2 mmol) and the acetylpyridineamide 36a (500 mg, 2 mmol) were converted by a similar method as described above to obtain the intermediate 34 in over 80% yield. To a solution of the pyridine amide 34 (432 mg, 1 mmol) in 5 mL of THF at −78° C. was added 1.5M DIBAL toluene solution (0.7 mL, 1.05 mmol) and the resulting yellow clear solution was warmed up to −20° C. slowly in 60 min. and then was quenched with water. Removal of solvent and chromatography of the crude mixture afforded the pyridinealdehyde 35 in 83% yield as a white solid. $^1$H-NMR ($CDCl_3$) δ1.25 (s,2($CH_3$)), 1.29 (s,2 ($CH_3$)), 1.70 (s,2($CH_2$)), 1.96 (s,$CH_3$), 5.47 (s,=CH), 5.92 (s,=CH), 7.10 (s,ArCH), 7.11 (s,Ar-CH), 7.70 (d,J=8.0 Hz,Pyr-CH), 7.88 (d,J=8.0 Hz,Pyr-CH), 8.72 (s, Pyr-CH), 10.06 (s,CHO).

The pyridinealdehyde 35 (10 mg, 0.03 mmol) was treated with 2.0 mL of $H_2O_2$ in 2 mL of methanol-water 1:1 mixture at room temperature for 10 h and then was quenched with 10% HCl. Extraction of the mixture with EtOAc (40 mL) and removal of solvent gave rise to 5-|1-(3,5,5,8,8-pentamethyl-5,6,7,8-tetrahydro-2-naphthyl)ethenyl| pyridine-2-carboxylic acid 60 as a white solid in almost quantitative yield. $^1$H-NMR ($CDCl_3$) δ1.26 (s,2($CH_3$)), 1.30 (s,2($CH_3$)), 1.70 (s,2($CH_2$)), 1.94 (s,$CH_3$), 5.47 (s,=CH), 5.92 (s,=CH), 7.10 (s,Ar-2(CH)), 7.76 (bs,Pyr-CH, 8.16 (bs,Pyr-CH) and 8.65 (s,Pyr-CH).

Treatment of the pyridinecarboxylic acid 60 (5 mg) with one drop of $SOCl_2$ in 1 mL of ethanol at reflux for 60 min followed by a flash chromatography gave rise to a quantitative yield of the ethyl ester 61 as a white solid. $^1$H-NMR ($CDCl_3$) δ1.26 (s,2($CH_3$)), 1.29 (s,2($CH_3$)), 1.44 (t,J=7.1 Hz,-$CH_2CH_3$), 1.69 (s,2($CH_2$)), 1.95 (s,$CH_3$), 4.46 (q,J=7.1 Hz,-$CH_2CH_3$)), 5.43 (s,=CH), 5.88 (s,=CH), 7.09 (s,Ar-CH), 7.10 (s,Ar-CH), 7.64 (d,J=8.0 Hz, Pyr-CH), 8.03 (d,J=8.0 Hz,Pyr-CH) and 8.68 (s,Pyr-CH).

EXAMPLE 33

Preparation of compound 62 where $R_1$, $R_2$, $R_3$, $R_4$, $R_5$ are methyl and R' and R" together are $CH_2CH_2$ (TPNCP):

To 162 mg (2.48 mmol) of zinc dust, 25 mg (0.25 mmol) of CuCl, and 332 mg (1.24 mmol) of $CH_2I_2$ in 3 mL of dry ether was added dropwise 150 mg (0.413 mmol) of olefin 26 where $R_1$, $R_2$, $R_3$, $R_4$, $R_5$ are methyl in 5 mL of dry ether. The mixture was heated at reflux for 12 h or until complete by H-NMR. Water was added and the organics extracted with ether, washed with $NH_4Cl$, brine and dried over $MgSO_4$. The desired cyclopropyl compound was purified by crystallization from ether-MeOH to give 60 mg (0.159 mmol) of the methyl ester of 62 as a pale yellow solid (39% yield). MP: 177° C.; $^1$H-NMR ($CDCl_3$) δ1.27 (s,2($CH_3$)), 1.31 (s,2($CH_3$)), 1.35 (s,$CH_2$), 1.70 (s,2($CH_2$)), 1.85 (s,$CH_2$), 2.11 (s,$CH_3$), 3.90 (s,$CH_3$), 6.75 (d,J=8.0 Hz,Pyr-CH), 7.14 (s,Ar-CH), 7.26 (s,Ar-CH), 7.98 (d,J=8.0 Hz,Pyr-CH) and 9.23 (s,Pyr-CH).

To 60 mg (0.16 mmol) of the above methyl ester in 10 mL of MeOH was added 1 mL of an aqueous 6N KOH solution. After stirring at room temperature for 1 h, the hydrolysis was complete and the reaction was acidified with 1N aqueous HCl until the solids precipitated. The product was extracted with ether, washed with water, brine and dried over $MgSO_4$. Crystallization from EtOAc-hexanes gave 33 mg (0.094 mmol) of the pyridinal carboxylic acid 62 (59% yield). MP: 275° C.; $^1$H-NMR($CDCl_3$) δ1.25 (s,2($CH_3$)), 1.35 (s,2($CH_3$) ), 1.40 (s,CH,), 1.72 (s,2($CH_2$)), 1.85 (s,$CH_2$), 2.15 (s,$CH_3$), 6.78 (d,J=8.0 Hz,Pyr-CH), 7.14 (s,Ar-CH), 7.26 (s,Ar-CH), 8.02 (d,J=8.0 Hz,Pyr-CH) and 9.15 (s,Pyr-CH).

EXAMPLE 34

Preparation of compound 63 where $R_1$, $R_2$, $R_3$, $R_4$, $R_5$ are methyl, R' and R" are methano, X=$CONHR_9$, and $R_9$=4-hydroxyphenyl (3-methyl-TTNEHBP):

To 750 mg (10 mml) of DMF in 22 mL of anhydrous ether was added 1.3 g (10 mmol) of oxalyl chloride. The reaction was stirred for 1 h, followed by removal of solvent to give a crude white solid (dimethylchloroformadinium chloride). To the dimethylchloroformadinium chloride was added 2.87 g (8.24 mmol) of compound 7 in 12 mL of dry DMF. The reaction was stirred for 20 m at room temperature followed by cooling to 0° C. The cooled solution of the acid chloride of 7 was added dropwise to a cooled DMF (0° C.) solution containing 3.62 g (33 mmol) of 4-aminophenol and 1.68 g (16.3 mmol) of triethyl amine. After stirring at 0° C. for 30 m, the reaction was warmed to room temperature for 12 h. Aqueous 20% HCl was added and the resulting solid was filtered and washed with water, acetone, and EtOAc to give 600 mg (1.36 mmol) of the desired compound 63 (17% yield). $^1$H-NMR (CDCl$_3$) δ1.29 (s,2(CH$_3$)), 1.31 (s,2(CH$_3$)), 1.71 (s,(CH$_2$)), 1.99 (s,CH$_3$), 5.31 (s,=CH), 5.80 (s,=CH), 6.85 (d,Ar-2(CH)), 7.09 (s,Ar-CH), 7.16 (s,Ar-CH), 7.40 (d,Ar-2(CH)), 7.48 (d,Ar-2(CH)), 8.40 (d,Ar-2(CH)).

EXAMPLE 35

Preparation of compound 64 where R$_1$, R$_2$, R$_3$, R$_4$, R$_5$ are methyl, R' and R" are methano, X=CONHR$_9$, and R$_9$=4-fluorophenyl (3-methyl-TTNEFBP):

The compound was prepared in a manner similar to that of compound 63 except that 4-fluoroaniline was substituted for 4-aminophenol. MP: 203° C.; $^1$H-NMR (CDCl$_3$) 61.28 (s,2(CH$_3$)), 1.31 (s,2(CH$_3$)), 1.70 (s,2(CH$_2$)), 1.96 (s,CH$_3$), 5.33 (s,=CH), 5.81 (s,=CH), 7.05 (d,J=9 Hz),Ar-2(CH)), 7.09 (s,Ar-CH), 7.13 (s,Ar-CH), 7.39 (d,J=8.4 Hz,Ar-2(CH)), 7.59 (dd,J=5.9 Hz,Ar-2CH), 7.75 (brs NH), 7.78 (d,J=8.4 Hz,Ar-2(CH)).

EXAMPLE 36

Preparation of compound 65 where R$_1$, R$_2$, R$_3$, R$_4$, R$_5$ are methyl, R' and R" are methano, X=CONHR$_9$, and R$_9$=4-phenylcarboxylic acid (3-methyl-TTNECBP):

The compound was prepared in a manner similar to that of compound 63 except that methyl 4-aminophenyl carboxylate was substituted for 4-aminophenol. The resulting ester was hydrolyzed in methanolic KOH, followed by acidification (20% HCl) to give the desired compound 65. MP: 200° C.; $^1$H-NMR (CDCl$_3$) δ1.28 (s,2(CH$_3$)), 1.31 (s,2(CH$_3$)), 1.71 (s,2(CH$_2$)), 1.97 (s,CH$_3$), 5.34 (s,=CH), 5.85 (s,=CH), 7.09 (s,Ar-CH), 7.14 (s,Ar-CH), 7.40 (d,J=8 Hz,Ar-CH), 7.80 (d,J=8 Hz,Ar-2(CH)), 7.87 (br s,Ar-2(CH)), 8.14 (br s,Ar-2(CH)).

EXAMPLE 37

Preparation of compound 66 where R$_1$, R$_2$, R$_3$, R$_4$, R$_5$ are methyl, R' and R" are oxo, X=CONHR$_9$, and R$_9$=3-hydroxyphenyl (3-methyl-m-TTNCHBP):

To 750 mg (10 mml) of DMF in 22 mL of anhydrous ether was added 1.3 g (10 mmol) of oxalyl chloride. The reaction was stirred for 1 h, followed by removal of solvent to give a crude white solid (dimethylchloroformadinium chloride). To the dimethylchloroformadinium chloride was added 2.88 g (8.24 mmol) of compound 4 in 12 mL of dry DMF. The reaction was stirred for 20 m at room temperature, followed by cooling to 0° C. The cooled solution of the acid chloride of 7 was added dropwise to a cooled DMF (0° C.) solution containing 3.62 g (33 mmol) of 4-aminophenol and 1.68 g (16.3 mmol) of triethyl amine. After stirring at 0° C. for 30 m, the reaction was warmed to room temperature for 12 h. Aqueous 20% HCl was added and the resulting solid was filtered and washed with water, acetone, and EtOAc to give 750 mg (1.70 mmol) of the desired compound 66 (21% yield). MP: 182° C.; $^1$H-NMR (CDCl$_3$) δ1.22 (s,2(CH$_3$)), 1.32 (s,2(CH$_3$)), 1.70 (s,2(CH$_2$)), 2.37 (s,CH$_3$), 6.58 (m,Ar-2(CH)), 7.20 (d,J=8 Hz,Ar-CH), 7.22 (s,Ar-CH), 7.28 (s,Ar-Ch), 7.91 (d,J=8.3 Hz,Ar-2(CH)), 8.26 (d,J=8.3 Hz,Ar-2(CH)).

EXAMPLE 38

Preparation of compound 67 where R$_1$, R$_2$, R$_3$, R$_4$, R$_5$ are methyl, R' and R" are methano, X=CONHR$_9$, and R$_9$=3-hydroxyphenyl (3-methyl-mT-TNEHBP):

The compound was prepared in a manner similar to that of compound 63 except that 3-aminophenol was substituted for 4-aminophenol. MP: 136° C.; $^1$H-NMR (CDCl$_3$) 61.28 (s,2(CH$_3$)), 1.31 (s,2(CH$_3$)), 1.70 (s,2(CH$_2$)), 1.97 (s,CH$_3$), 5.35 (s,=CH), 5.84 (s,=CH), 6.57 (m,Ar-2(CH)), 7.09 (s,Ar-CH), 7.14 (s,Ar-CH), 7.16 (m,Ar-CH), 7.39 (d,J=8.3 Hz,Ar-2(CH)), 8.09 (d,J=8.3 Hz,Ar-2(CH)).

EXAMPLE 39

Preparation of compound 68 where R$_1$, R$_2$, R$_3$, R$_4$, R$_5$ are methyl, R' and R" are methano, X=CONHR$_9$, and R$_9$=2-hydroxyphenyl (3-methyl-o-TTNCHBP):

The compound was prepared in a manner similar to that of compound 63 except that 2-aminophenol was substituted for 4-aminophenol. MP: 180° C.; $^1$H-NMR (CDCl$_3$) 61.28 (s,2(CH$_3$)), 1.31 (s,2(CH$_3$)), 1.71 (s,2(CH$_2$)), 1.97 (s,CH$_3$), 5.35 (s,=CH), 5.84 (s,=CH), 6.9 (m,Ar-CH), 7.08–7.2 (m,Ar-CH), 7.09 (s,Ar-CH), 7.13 (s,Ar-CH), 7.42 (d,J=8.4 Hz,Ar-2(CH)), 7.83 (d,J=8.4 Hz,Ar-2(CH)), 8.03 (brs,Ar-CH), 8.64 (s,NH).

EXAMPLE 40

Preparation of compound 69 where R$_1$, R$_2$, R$_3$, R$_4$, R$_5$ are methyl, R' and R" are methano, X=CONHR$_9$, and R$_9$=3-phenylcarboxylic acid (3-methyl-m-TTNECBP):

The compound was prepared in a manner similar to that of compound 63 except that methyl-3-amino phenyl carboxylate was substituted for 4-aminophenol. The resulting ester was hydrolyzed in methanolic KOH followed by acidification (20% HCl) to give the desired compound 69. MP: 250° C.; $^1$H-NMR (CDCl$_3$) 61.28 (s,2(CH$_3$)), 1.31 (s,2(CH$_3$)), 1.71 (s,2(CH$_2$)), 1.97 (s,CH$_3$), 5.34 (s,=CH), 5.85 (s,=CH), 7.09 (s,Ar-CH), 7.14 (s,Ar-CH), 7.40 (d,J=8 Hz, Ar-2(CH)), 7.55 (m,Ar-CH), 7.76 (m,Ar-CH), 7.80 (d,J=8 Hz, Ar-2(CH)), 7.87 (s,Ar-CH), 8.14 (s,NH).

EXAMPLE 41

Preparation of compound 70 where R$_1$, R$_2$, R$_3$, R$_4$, R$_5$ are methyl, R' and R" are methano, n=0, and X=COOH:

The compound was prepared in a manner similar to that of compound 7 except that 1,1,3,3,5-pentamethylindane was substituted for 1,1,4,4,6-pentamethyl-1,2,3,4-tetrahydronaphthalene in examples 1, 2, 4, and 5. MP: 145° C.; $^1$H-NMR (CDCl$_3$) δ1.05 (s,2(CH$_3$)), 1.28 (s,CH$_3$), 1.31 (s,CH$_3$), 1.38 (s,CH$_2$), 1.98 (s,CH$_3$), 5.34 (s,CH), 5.84 (s,CH), 6.90 (s, Ar-CH), 6.92 (s, Ar-CH), 7.36 (d,J=8.4 Hz, Ar-2 (CH)), 8.00 (d,J=8.4 Hz,Ar-2(CH)).

EXAMPLE 42

Preparation of compound 71 where R$_1$, R$_2$, R$_3$, R$_4$, R$_5$, R$_{14}$ are methyl, R' and R" are methano, n=0, and X=COOH:

The compound was prepared in a manner similar to that of compound 7 except that 1,1,2,3,3,5-pentamethylindane was substituted for 1,1,4,4,6-pentamethyl-1,2,3,4-tetrahydronaphthalene in examples 1, 2, 4, and 5. MP: 217° C.; $^1$H-NMR (CDCl$_3$) δ1.01 (d,J=7.3 Hz,CH$_3$); 1.08 (s,CH$_3$), 1.10 (s,CH$_3$), 1.27 (s,CH$_3$), 1.30 (s,CH$_3$), 1.88 (q,CH), 2.00 (s,CH$_3$), 5.35 (s,=CH), 5.85 (s,=CH), 6.95 (s,Ar-CH), 6.98 (s,Ar-CH), 7.38 (d,J=8.3 Hz,Ar-2(CH)), 8.00 (d,J=8.3 Hz,Ar-2(CH)).

EXAMPLE 43

Preparation of compound 72 where R$_1$, R$_2$, R$_3$, R$_4$, R$_5$ are methyl, R' and R" are H, and X=COOH:

The compound was prepared in a manner similar to that of compound 4 (examples 1 and 2) except that methyl-4-(bromomethyl)benzoate was substituted for mono-methyl terephthalic acid chloride. MP: 237° C.; $^1$H-NMR (CDCl$_3$)

δ1.23 (s,2($CH_3$)), 1.27 (s,2($CH_3$)), 1.67 (s,2($CH_2$)), 2.16 (s,$CH_3$), 4.06 (s,$CH_2$), 7.01 (s,Ar-CH), 7.08 (s,Ar-CH), 7.25 (d,J=8 Hz,Ar-2(CH)), 8.01 (d,J=8 Hz,Ar-2(CH)).

EXAMPLE 44

Preparation of compound 81:

To 4.56 g (25.0 mmol) of trimethylphosphonoacetate in 50 mL of THF under argon at 0° C. was added 902 mg (22.5 mmol) of NaH (60% in oil) in three portions. After stirring for 30 m at 0° C., 2.27 mL (21.2 mmol) of isopropyl-methylketone in 10 mL of THF was added. The reaction mixture was heated to 65° C. for 3 hr, then cooled to room temperature, poured into saturated aqueous $NH_4Cl$ (50 mL), and the organic products extracted with ether (250 mL). The ether layer was washed with water (2×30 mL), brine (30 mL), dried ($MgSO_4$), filtered through a short bed of silica gel, and concentrated to afford 1.6 g of an essentially pure E,Z mixture of the desired ester 81(65% yield).

EXAMPLE 45

Preparation of compound 87A where R' is isopropyl and R" is H:

To a solution of 1.2 mL (8.6 mmol) of diisopropylamine in 5 mL of THF at −78° C. was added 2.57 mL (6.4 mml) of a 2.5M solution of nBuLi. The mixture was stirred for 10 m, followed by dropwise addition of 609 mg (4.3 mmol) of the ester 81. The reaction was warmed to room temperature and stirred for an additional 30 m, followed by addition of 651 mg (4.3 mmol) of cyclocitral in 5 mL of THF. After stirring for 30 m, the reaction was poured into 10 mL of saturated aqueous $NH_4Cl$ and the organic layer extracted with ether. The ether layer was washed with water and brine, dried ($MgSO_4$), filtered, and concentrated to afford 729 mg of essentially pure lactone 87A.

To 1.1 g (4.2 mmol) of the lactone 87A in 21 mL of $CH_2Cl_2$ at −78° C., was added DIBAL (5.0 mmol, 5 mL of a 1M hexane solution). After stirring at −78° C. for 30 m, the reaction was quenched with 20 mL of saturated aqueous KNa-tartrate solution, followed by extraction of the reaction products with 100 mL of EtOAc. The EtOAc solution was dried over $MgSO_4$, filtered, and concentrated to give the lactol 87B in quantitative yield. The lactol was used in the next step without further purification.

EXAMPLE 46

Preparation of compound 88 where R' is isopropyl and R" is H:

To a $CH_2Cl_2$ solution containing 380 mg (1.44 mmol) of the lactol 87B at room temperature was added HCl (0.12M in $CH_2Cl_2$, 3 mL, 0.36 mmol). The reaction was stirred for 3 h or until all of the lactol was consumed by TLC. The reaction mixture was poured into saturated $NaHCO_3$ at 0° C., followed by extraction with 50 mL of $CH_2Cl_2$. The lower organic layer was washed with water (2×10 mL), dried ($MgSO_4$), and concentrated to obtain 310 mg (1.26 mmol) of virtually pure aldehyde 88(88% yield).

EXAMPLE 47

Preparation of compound 89 where R' is isopropyl and R" is H:

To a solution of 815 mg (3.1 mmol) of the phosphono reagent 90 in 6 mL of THF was added 93 mg (2.3 mmol) of a NaH (60% in oil), and the mixture stirred for 10 m. To this mixture at room temperature was added 380 mg of the aldehyde 88 (from example #46). After stirring for 30 m, aqueous $NH_4Cl$ was added, followed by extraction of the organic products with ether. The ethereal layer was washed (water, brine), dried ($MgSO_4$), filtered, concentrated, and purified by flash chromatography (silica gel, 60% benzene in hexanes) to give the ester 89.

EXAMPLE 48

Preparation of compound 75:

To a solution of 15 mg (0.042 mmol) of compound 89 in 1 mL of a 1:1 MeOH-$H_2O$ solution at room temperature was added 4.3 mg (0.26 mmol) of KOH. The mixture was heated to 70° C. for 2 h, cooled to 0° C., diluted with ether (10 mL), and acidified with 0.1M HCl. The ether layer was washed (water, brine), dried ($MgSO_4$), concentrated, and purified by silica gel chromatography (10% MeOHCH$Cl_3$) to give the pure acid 75. $^1$H-NMR ($CDCl_3$) δ 1.02 (s, 2($CH_3$); 1.12 (d, J=4.5 Hz, (2($CH_3$)), 1.50 (m, $CH_2$), 1.62 (m, $CH_2$), 1.75 (s, $CH_3$), 2.05 (t, J=5 Hz, $CH_2$), 2.31 (s, $CH_3$), 2.75 (q, J=4.5 Hz, CH($CH_3$)$_2$), 5.78 (s, CH), 6.08 (d, J=12 Hz, CH), 6.24 (d, J=16 Hz, CH), 6.26 (d, J=16 Hz, CH), 7.21 (dd, J=16, 12 Hz, CH).

EXAMPLE 49

Preparation of compound 73:

Compound 73 was prepared in a manner similar to compound 75 (examples 44–48) except compound 79, rather than compound 81, was utilized as a starting material. Compound 79 was prepared in a manner similar to compound 81 except that ethyl-methylketone was used instead of isopropyl-methylketone. For intermediate compounds 87, 88, and 89, R' is ethyl and R" is H. $^1$H-NMR ($CDCl_3$) δ 1.05 (s, 2($CH_3$)), 1.151 (t, J=4.5 Hz, $CH_2CH_3$), 1.51 (m, $CH_2$), 1.62 (m, $CH_2$), 1.71 (s, $CH_3$), 2.05 (m, $CH_2$), 2.30 (s, $CH_3$), 2.35 (t, J=4.5 Hz, $CH_2CH_3$), 5.78 (s, CH), 6.05 (d, J=11 Hz, CH), 6.25 (d, J=15 Hz, CH), 6.30 (d, J=15 Hz, CH), 6.52 (dd, J=15, 11 Hz, CH).

EXAMPLE 50

Preparation of compound 74:

Compound 74 was prepared in a manner similar to compound 75 (examples 44–48) except compound 80, rather than compound 81, was utilized as a starting material. Compound 80 was prepared in a manner similar to compound 81 except that n-propyl-methylketone was used instead of isopropyl-methylketone. For intermediate compounds 87, 88, and 89, R' is n-propyl and R" is H. $^1$H-NMR ($CDCl_3$) δ0.9 (t, J=5 Hz, $CH_2CH_3$), 1.02 (s, 2($CH_3$)), 1.40–1.65 (m, 3($CH_2$)), 1.70 (s, $CH_3$), 2.00 (m, $CH_2$), 2.40 (m, $CH_2CH_2CH_3$), 5.75 (s, CH), 6.05 (d, J=12 Hz, CH), 6.21 (d, J=15 Hz, CH), 6.25 (d, J=16 Hz, CH), 6.50 (d, J=16 Hz, CH), 7.10 (dd, J=15, 12 Hz, CH).

EXAMPLE 51

Preparation of compound 76:

Compound 76 was prepared in a manner similar to compound 75 (examples 44–48) except compound 82, rather than compound 81, was utilized as a starting material. Compound 82 was prepared in a manner similar to compound 81 except that methyl-trimethylphosphonoacetate was used instead of trimethylphosphonoacetate and acetone was used instead of isopropyl-methylketone. For intermediate compounds 87, 88, and 89, R' is methyl and R" is methyl. $^1$H-NMR ($CDCl_3$) δ 1.05 (s, 2($CH_3$)), 1.50 (m, ($CH_2$), 1.65 (m, $CH_2$), 1.75 (s, $CH_3$), 1.95 (s, $CH_3$), 2.05 (m, $CH_2$+$CH_3$), 2.35 (s, $CH_3$), 5.81 (s, CH), 6.25 (d, J=16 Hz, CH), 6.30 (d, J=16 Hz, CH), 6.72 (d, J=16 Hz, CH), 7.35 (d, J=16 Hz, CH).

EXAMPLE 52

Preparation of compound 77:

Compound 77 was prepared in a manner similar to compound 75 (examples 44–48) except compound 83, rather than compound 81, was utilized as a starting material. Compound 83 was prepared in a manner similar to compound 81 except that t-butyl-methylketone was used instead of isopropyl-methylketone. For intermediate compounds 87, 88, and 89, R' is t-butyl and R" is H. $^1$H-NMR ($CDCl_3$) δ 0.89 (s, $CH_3$), 0.90 (s, $CH_3$), 1.00 (s, $C(CH_3)_3$), 1.45 (m, $CH_2$), 1.65 (m, $CH_2$), 1.70 (s, $CH_3$), 2.01 (t, J=5 Hz, $CH_2$), 2.32 (s, $CH_3$), 5.71 (s, CH), 6.00 (d, J=12 Hz, CH), 6.32 (d, J=16 Hz, CH), 6.50 (d, J=16 Hz, CH), 7.10 (dd, J=16, 12 Hz, CH).

EXAMPLE 53

Preparation of compound 95:

To 1.4 g (2.9 mmol) of the phosphonium salt 91 in 20 mL of dry THF under argon at 0° C. was added 1.1 mL (2.6 mmol) of a 2.4M nBuLi solution. The dark red ylide was stirred at 0° C. for 30 m and cooled to −78° C. To the ylide was added 391 mg (2.9 mmol) of the dialdehyde 92 in 2 mL of THF. The reaction was stirred for 20 m and then poured into aqueous $NH_4Cl$, diluted with ether (50 mL), the ethereal layer washed with water, brine, dried ($MgSO_4$), filtered, and concentrated. The crude product was purified by chromatography ($SiO_2$, 5% ether-hexane) to give 543 mg (2.14 mmol) of the pure aldehyde 93 (74% yield).

Compound 94 was prepared in a manner similar to example #47.

Compound 95 was prepared in a manner similar to example #48. $^1$H-NMR ($CDCl_3$) δ 1.06 (s, $(CH_3)_2$), 1.50 (m, $CH_2$), 1.65 (m, $CH_2$), 1.75 (s, $CH_3$), 2.05 (t, J=5 Hz, $CH_2$), 2.40 (s, $CH_3$), 5.90 (s, CH), 6.45 (d, J=16 Hz, CH), 6.60 (d, J=16 Hz, CH), 6.72 (d, J=16 Hz, CH), 7.20–7.50 (m, Ar-H+CH).

EXAMPLE 54

Preparation of compound 100:

To a solution containing cis-1,2-cyclohexanedimethanol 96 (400 mg, 2.9 mmol) and triethylamine (300 mg, 3.0 mmol) in 30 mL of ether was added benzoyl chloride (400 mg, 2.9 mmol), giving rise to a white cloudy solution. The reaction mixture was stirred at room temperature for 15 h. Filtration from the white solid provided the crude mixture, which was then chromatographed to afford the monoprotected diol in 50% yield. To a solution of DMSO (0.3 mL, 4 mmol) in 3 mL of methylene chloride at −78° C. was added 2.0M $CH_2Cl_2$ solution (1.0 mL, 2.0 mmol) of oxalyl chloride and the resulting clear solution was stirred at −60° C. for 20 m before the above alcohol (370 mg, 1.5 mmol) was introduced as a $CH_2Cl_2$ solution. The reaction mixture was allowed to stir at −60° C. for an additional 20 m and triethylamine was added. The mixture was then warmed to room temperature and quenched with water. Standard work-up followed by chromatography gave the cis-aldehyde 97 in 87% isolated yield as a colorless oil; $^1$H-NMR ($CDCl_3$, 400 MHz) 1.40–1.60 (m, 3 H), 1.63–1.75 (m, 4 H), 1.90–2.00 (m, 1 H), 2.35–2.48 (m, 1 H), 2.62–2.68 (m, 1 H), 4.44 (d, J=7.2 Hz, 2 H), 7.44 (t, J=7.6 Hz, 2 H), 7.54 (t, J=7.6 Hz, 1 H), 7.99 (d, J=7.6 Hz, 2 H) and 9.86 (s, 1 H).

The reaction of 2,6,6-trimethylcyclohexenylmethyltriphenylphosphonium bromide 91 (1.0 g, 2 mmol) with 0.5M toluene solution of KN$(SiMe_3)_2$ (3 mL, 1.5 mmol) in THF gave a dark red slurry at room temperature, to which the aldehyde 97 in THF (320 mg, 1.3 mmol) was slowly added over 30 min. After stirring for 2 h, the reaction mixture was quenched with 2% HCl and was extracted with ethyl acetate. Removal of solvent and chromatography of the crude residue afforded the diene product 98 in about 40% yield, which was then hydrolyzed to give the alcohol 98a; $^1$H-NMR ($CDCl_3$, 400 MHz) 0.97 (s, 3 H), 0.98 (s, 3 H), 1.20–1.45 (m, 8 H), 1.55–2.00 (m, 8 H), 1.66 (s, 3 H), 3.44–3.52 (m, 1 H), 3.65–3.71 (m, 1 H), 5.26 (dd, J=12.5 and 7.5 Hz, 1 H) and 5.88 (dd, J=12.5 and 1.0 Hz, 1 H).

The alcohol 98a was oxidized by similar method described above to afford the aldehyde 99 in excellent yield, which then was coupled by a standard Wittig rection to form the ethyl ester of the final product. Hydrolysis of the ester with KOH in methanol/water provided 100 as a colorless oil; $^1$H-NMR ($CDCl_3$, 400 MHz) 0.89 (s, 3 H), 0.92 (s, 3 H), 1.20–1.80 (m, 14 H), 1.58 (s, 3 H), 1.90–1.98 (m, 2 H), 2.23 (s, 3 H), 5.12 (dd, J=13.1 and 7.0 Hz, 1 H), 5.655.82 (m, 2 H) and 6.08–6.13 (m, 2 H).

EXAMPLE 55

Preparation of compound 104:

To a clear solution of the bromocompound 33 (1.41 g, 5.0 mmol) in THF at −78° C. was added 1.6M n-BuLi hexane solution (3.5 mL, 5.6 mmol), generating a cloudy yellowish mixture, which was stirred at the temperature for 15m. The anion solution was cannulated to a CuI THF slurry at −30° C. and the resulting dark mixture was allowed to stir for 20m before being cannulated to another flask charged with acetoxyacetyl chloride THF solution at −78° C. The reaction mixture was stirred at low temperature for 20m and then was warmed up to RT followed by addition of water to quench the reaction. Standard work-up and purification by flash chromatography of the mixture afforded the product 101 in 55% yield; $^1$H-NMR ($CDCl_3$, 400 MHz) 1.28 (s, 6 H), 1.29 (s, 6 H), 1.69 (s, 4 H), 2.21 (s, 3 H), 2.47 (s, 3 H), 5.20 (s, 2 H), 7.18 (s, 1 H) and 7.26 (s, 1 H).

The intermediate 101 (200 mg, 0.7 mmol) was treated with the ylide derived from KN$(SiMe_3)_2$ and methyltriphenylphosphonium bromide (357 mg, 1.0 mmol) in 20 mL of THF at room temperature for 16 h followed by hydrolysis of the product to give the allylic alcohol 102 in 50% yield; $^1$H-NMR ($CDCl_3$, 400 MHz) 1.26 (s, 6 H), 1.28 (s, 6 H), 1.67 (s, 4 H), 2.25 (s, 3 H), 4.31 (d, J=6.0 Hz, 2 H), 5.05 (s, 1 H), 5.45 (s, 1 H), 7.03 (s, 1 H) and 7.10 (s, 1 H).

To a solution of the allylic alcohol 102 (95 mg, 0.35 mmol) in 1 mL of ethylene dichloride was added $Et_2Zn$ (0.21 mL, 2 mmol), and then $CH_2ICl$ (700 mg, 4 mmol) at 0° C. The resulting mixture was stirred for 60 m till all starting material disappeared. Standard work-up followed by chromatography of the mixture afforded the cyclopropanol; $^1$H-NMR ($CDCl_3$, 400 MHz) 0.90–1.10 km, 4 H), 1.26 12 H), 1.65 (s, 4 H), 2.37 (s, 3 H), 3.57 (d, J=5.5 Hz, 2 H), 7.05 (s, 1 H) and 2.21 (s, 1 H). The intermediate was oxidized to the corresponding aldehyde 103 by the method described above; $^1$H-NMR ($CDCl_3$, 400 MHz) 0.90–1.10 (m, 4 H), 1.25 (s, 6 H), 1.27 (s, 6 H), 1.65 (s, 4 H), 2.21 (s, 3 H), 7.10 (s, 1 H), 7.11 (s, 1 H) and 9.67 (s, 1 H).

The aldehyde was converted by the standard Wittig coupling and ester hydrolysis sequence described previously to the final acid 104; $^1$H-NMR ($CDCl_3$, 400 MHz) 1.05–1.13 (m, 4 H), 1.25 (s, 6 H), 1.28 (s, 6 H), 1.70 (s, 4 H), 2.22 (s, 3 H), 2.24 (s, 3 H), 5.53 (d, J=15.5 Hz, 1 H), 5.85 (d, J=15.5 Hz, 1 H), 6.14 (s, 1 H), 7.05 (s, 1 H) and 7.12 (s, 1 H).

EXAMPLE 56

Preparation of compound 110:

To a solution of the diacid 105 (5 g, 38 mmol) in 60 mL of THF at 0° C. was added dropwise the $BH_3$-THF solution, generating a white slurry, which was stirred at room temperature for 16 h. Then, 22 mL of THF-$H_2O$ (1:1) was added followed by $K_2CO_3$. After stirring for 60 m, the reaction mixture was filtered and the filtrate was dried and concentrated to provide the crude diol, which was directly treated with benzoyl chloride (7 g, 50 mmol) and $Et_3N$ (6 g, 60 mmol) in ether for 2 h. Filtration from the white solid and chromatography of the residue afforded the mono-ester of the diol and the diester in good yield. The monoester was then oxidized by the same method to give the corresponding aldehyde 106; $^1H$-NMR ($CDCl_3$, 400 MHz) 1.24–1.36 (m, 4 H), 4.56 (s, 2 H), 7.43 (t, J=7.9 Hz, 2 H), 7.55 (t, J=7.9 Hz, 1 H), 8.01 (d, J=7.9 Hz, 2 H) and 9.06 (s, 1 H).

To a yellow solution of 2,6,6-trimethylcyclohexenylmethyltriphenylphosphonium bromide 91 (1.5 g, 3 mmol) in 10 mL of THF/DMPU (5/1) at −78° C. was added a 1.0M $LiN(SiMe_3)_2$ THF solution (3 mL, 3 mmol), generating a dark red solution, which was warmed up to RT. The aldehyde 106 (1.1 g, 5 mmol) in 3 mL of THF was cannulated slowly over 60 m to the above ylide solution and the reaction mixture was allowed to stir for an additional 1 h. Standard work-up followed by chromatography afforded the product 107 in 40% yield; $^1H$-NMR ($CDCl_3$, 400 MHz) 0.76–0.86 (m, 4 H), 0.95 (s, 6 H), 1.41–1.46 (m, 2 H), 1.56–1.62 (m, 2 H), 1.64 (s, 3 H), 1.95 (t, J=4.0 Hz, 1 H), 4.34 (s, 2 H), 5.31 (d, J=16.0 Hz, 1 H), 5.95 (d, J=16.0 Hz, 1 H), 7.41 (t, J=7.6 Hz, 2 H), 7.54 (t, J=7.6 Hz, 1 H) and 8.04 (d, J=7.6 Hz, 2 H).

Treatment of the ester 107 with MeLi in THF provided the alcohol 108 in quantitative yield as a colorless oil; $^1H$-NMR ($CDCl_3$, 400 MHz) 0.68 (s, 4 H), 0.97 (s, 6 H), 1.42–1.47 (m, 2 H), 1.581.63 (m, 2 H), 1.65 (s, 3 H), 1.99 (t, J=5.2 Hz, 2 H), 3.58 (d, J=6.0 Hz, 2 H), 5.27 (d, J=16.0 Hz, 1 H) and 5.94 (d, J=16.0 Hz, 1 H).

The alcohol 108 was converted to the intermediate 109 by the Wittig sequence described previously: Treatment of 108 (180 mg, 0.8 mmol) with triphenyl phosphine (262 mg, 1.0 mmol) and carbontetrabomide (332 mg, 1.0 mmol) in 10 mL of THF for 1 h provided the bromo compound, which was reacted with excess of potassium cyanide in ethanol/water (2/1) for 6 h to give the cyano compound 109; $^1H$-NMR ($CDCl_3$, 400 MHz) 0.78–0.82 (m, 4 H), 0.99 (m, 6 H), 1.45–1.60 (m, 4 H), 1.84 (s, 3 H), 1.95–2.00 (m, 2 H) 2.54 (s, 2 H), 5.18 (d, J=15.5 Hz, 1 H) and 5.90 (d, J=15.5 Hz, 1 H).

The cyano compound 109 was reduced to the aldehyde with DIBAL followed by the Wittig reaction and ester hydrolysis described for compounds 100 and 104, Zto give the desired product 110; $^1H$-NMR ($CDCl_3$, 400 MHz) 0.59–0.68 (m, 4 H), 0.93 (s, 6 H), 1.40–1.45 (m, 2 H), 1.55–1.60 (m, 2 H), 1.61 (s, 3 H), 1.94 (t, J=6.2 Hz, 2 H), 2.27 (s, 3 H), 2.33 (d, J=5.4 Hz, 2 H), 5.16 (d, J=16.0 Hz, 1 H), 5.71 (s, 1 H), 5.24 (d, J=16.0 Hz, 1 H), and 6.20–6.30 (m, 2 H).

EXAMPLE 57

Preparation of compound 123:

Condensation of 117 with the isopropyl-methyl ketone 118 was carried out by addition of $AlCl_3$ in $CH_2Cl_2$ at 25° C. to give the ketone 119, which was then condensed with the cyanomethylphosphonate 124 under NaH treatment using THF and DMPU as cosolvent at 80° C., followed by column chromatography to afford the pure cis-nitrile 120. DIBAL reduction of the nitrile 120 afforded the corresponding cis-aldehyde 121. Coupling of the aldehyde 121 with the phosphonate 122 under nBuLi treatment using THF and DMPU as cosolvent and subsequent hydrolysis of the Wittig product gave, after column chromatography, pure 123 as a light yellow solid, MP=170°–171° C.; $^1H$-NMR($CDCl_3$): ppm 1.07 (d, J=7 Hz, $2xCH_3$), 1.25 (s, $2xCH_3$), 1.28 (s, $2xCH_3$), 1.68 (s, $CH_2CH_2$), 2.11 (s, $CH_3$), 2.70 (m, CH), 5.73 (s, CH), 6.16 (d, J=11 Hz, CH), 6.27 (d, J=15 Hz, CH), 6.66 (dd, J=11, 15 Hz, CH), 6.90 (dd, J=2, 8 Hz, Ar-CH), 7.03 (d, J=2 Hz, Ar-CH), 7.25 (d, J=8 Hz, Ar-CH).

EXAMPLE 58

Preparation of compound 128:

Consensation of 1,1,4,4,6-pentamethyl-1,2,3,4-tetrahydronaphthalene 1 with acetyl chloride was carried out by addition of $AlCl_3$ in $CH_2Cl_2$ at 25° C. to give ketone 125, which was then condensed with the cyanomethyl phosphonate 124 under NaH treatment using THF and DMPU as cosolvent at 80° C., followed by column chromatography to afford the pure cis-nitrile 126. DIBAL reduction of the nitrile 126 afforded the corresponding cis-aldehyde 127. Coupling of aldehyde 127 with the phosphonate 122 under nBuLi treatment using THF and DMPU as cosolvent and subsequent hydrolysis of the Wittig product gave, after column chromatography, pure 128; $^1H$-NMR($CDCl_3$) ppm 1.22 (s, $2xCH_3$), 1.27 (s, $2xCH_3$), 1.66 (s, $CH_2CH_2$) 2.07 (s, $CH_3$), 2.08 (s, $CH_3$), 2.13 (s, $CH_3$), 5.72(s, CH), 6.19 (d, J=16 Hz, CH), 6.22(d, J=8 Hz, CH), 6.33 (dd, J=8, 16 Hz, CH), 6.90 (s, Ar-CH), 7.08 (s, Ar-CH).

Evaluation of Retinoid Receptor Subtype Selectivity

Representative synthetic retinoid compounds of the current invention were analyzed and found to exhibit subtype selectivity for retinoid receptors, and to be capable of modulating processes selectively mediated by retinoid X receptors, as discussed more fully below.

As employed herein, the phrase "processes selectively mediated by retinoid X receptors" refers to biological, physiological, endocrinological, and other bodily processes which are mediated by receptors or receptor combinations which are responsive to retinoid X receptor selective processes, e.g., compounds which selectively activate one and/or multiple members of the RXR subfamily. Modulation includes activation or enhancement of such processes as well as inhibition or repression, and can be accomplished in vitro or in vivo. In vivo modulation can be carried out in a wide range of subjects, such as, for example, humans, rodents, sheep, pigs, cows, and the like. It is well accepted that modulation of such processes has direct relevance to use in treating disease states.

The receptors which are responsive to retinoid X receptor selective ligands include: retinoid X receptor-alpha, retinoid X receptor-beta, retinoid X receptor-gamma, and splicing variants encoded by the genes for such receptors, as well as various combinations thereof (i.e., homodimers, homotrimers, heterodimers, heterotrimers, and the like). Also included are combinations of retinoid X receptors with other members of the steroid/thyroid superfamily of receptors with which the retinoid X receptors may interact by forming heterodimers, heterotrimers, and the higher heteromultimers. For example, the retinoic acid receptor-alpha, -beta, or -gamma isoforms form a heterodimer with any of the retinoid X receptor isoforms, (i.e., alpha, beta, or gamma, including any combination of the different receptor isoforms), and the various retinoid X receptors form a heterodimer with thyroid receptor and form a heterodimer with vitamin D receptor. Members of the retinoid X receptor subfamily form a heterodimer with certain "orphan receptors" including PPAR (Issemann and Green, *Nature*, 347: 645–49 (1990)); HNF4 (Sladek et al., *Genes & Development* 4: 2353–65 (1990)); the COUP family of receptors (e.g., Miyajima et al., *Nucleic Acids Research* 16: 11057–74 (1988), and Wang et al., *Nature*, 340: 163–66 (1989) ); COUP-like receptors and COUP homologs, such as those described by Mlodzik etal. (*Cell*, 60: 211–24 (1990)) and Ladias et al. (*Science*, 251: 561–65 (1991)); the ultraspiracle receptor (e.g., Oro et al., *Nature*, 347: 298–301 (1990)); and the like.

As employed herein, the phrase "members of the steroid/thyroid superfamily of receptors" (also known as "nuclear receptors" or "intracellular receptors") refers to hormone binding proteins that operate as ligand-dependent transcription factors. Furthermore, this classification includes identified members of the steroid/thyroid superfamily of receptors for which specific ligands have not yet been identified (referred to hereinafter as "orphan receptors"). All members of the intracellular receptor superfamily have the intrinsic ability to bind to specific DNA sequences. Following binding, the transcriptional activity of a target gene (i.e., a gene associated with the specific DNA sequence) is modulated as a function of the ligand bound to the receptor. Also, see Heyman et al., *Cell*, 68: 397–406 (1992), and copending U.S. Ser. No. 809,980, filed Dec. 18, 1991, whose entire disclosures are incorporated herein by reference.

The modulation of gene expression by the ligand retinoic acid and its receptors can be examined in a reconstituted system in cell culture. Such a system was used to evaluate the synthetic retinoid compounds of this invention for their interaction with the retinoid receptor subtypes RARα, RARβ, RARγ, RXRα, RXRβ, and RXRγ.

The system for reconstituting ligand-dependent transcriptional control, which was developed by Evans et al., *Science*, 240: 889–95 (1988), has been termed a "co-transfection" or "cis-trans" assay. This assay is described in further detail in U.S. Pat. Nos. 4,981,784 and 5,071,773, which are incorporated herein by reference. Also see Heyman et al., *Cell*, 68: 397–406 (1992). The co-transfection assay provides a mechanism to evaluate the ability of a compound to modulate the transcription response initiated by an intracellular receptor. The co-transfection assay is a functional, rapid assay that monitors hormone or ligand activity, is a good predictor of an in vivo system, and can be used to quantitate the pharmacological potency and utility of such ligands in treating disease states. Berger, et al., *J. Steroid Biochem Molec. Biol.*, 41: 733–38 (1992).

Briefly, the co-transfection assay involves the introduction of two plasmids by transient transfection into a retinoid receptor-negative mammalian cell background. The first plasmid contains a retinoid receptor cDNA and directs constitutive expression of the encoded receptor. The second plasmid contains a cDNA that encodes for a readily quantifiable protein, e.g., firefly luciferase or chloramphenicol acetyl transferase (CAT), under control of a promoter containing a retinoid acid response element, which confers retinoid dependence on the transcription of the reporter. In this co-transfection assay, all retinoid receptors respond to all-trans-retinoic acid in a similar fashion. This assay can be used to accurately measure efficacy and potency of retinoic acid and synthetic retinoids as ligands that interact with the individual retinoid receptor subtypes.

Accordingly, synthetic retinoid compounds of the current invention were evaluated for their interaction with retinoid receptor subtypes using the co-transfection assay in which CV-1 cells were co-transfected with one of the retinoid receptor subtypes, a reporter construct, and an internal control to allow normalization of the response for transfection efficiency. The following example is illustrative.

EXAMPLE 59

Retinoids: All-trans-retinoic acid (RA) and 13-cis-retinoic acid (13-cis-RA) were obtained from Sigma. 9-cis-retinoic acid (9-cis-RA) was synthesized as described in Heyman et al., *Cell*, 68: 397–406 (1992). Retinoid purity was established as greater than 99% by reverse phase high-performance liquid chromatography. Retinoids were dissolved in dimethylsulfoxide for use in the transcriptional activation assays.

Plasmids: The receptor expression vectors used in the co-transfection assay have been described previously (pRShRAR-α: Giguere et al. (1987); pRShRAR-β and pRShRAR-γ: Ishikawa et al. (1990); pRShRXR-α: Mangelsdorf et al., (1990); pRSmRXR-β and pRSmRXR-γ: Mangelsdorf et al., *Genes & Devel.*, 6: 329–44 (1992)). A basal reporter plasmid Δ-MTV-LUC (Hollenberg and Evans, *Cell*, 55: 899–906 (1988)) containing two copies of the TRE-palindromic response element 5'-TCAGGTCATGACCTGA-3' (Umesono et al., *Nature*, 336: 262–65 (1988)) was used in transfections for the RARs, and CRBPIIFKLUC, which contains an RXRE (retinoid X receptor response element (Mangelsdorf et al., *Cell*, 66: 555–61 (1991)), was used in transfections for the RXRs.

Co-transfection Assay In CV-1 Cells: A monkey kidney cell line, CV-1, was used in the cis-trans assay. Cells were transfected with two plasmids. The trans-vector allowed efficient production of the retinoid receptor in these cells, which do not normally express this receptor protein. The cis-vector contains an easily assayable gene product, in this case the firefly luciferase, coupled to a retinoid-responsive promoter, i.e., an RARE or RXRE. Addition of retinoic acid or an appropriate synthetic retinoid results in the formation of a retinoid-RAR or -RXR complex that activates the expression of luciferase gene, causing light to be emitted from cell extracts. The level of luciferase activity is directly proportional to the effectiveness of the retinoid-receptor complex in activating gene expression. This sensitive and reproducible co-transfection approach permits the identification of retinoids that interact with the different receptor isoforms.

Cells were cultured in DMEM supplemented with 10% charcoal resin-stripped fetal bovine serum, and experiments were conducted in 96-well plates. The plasmids were transiently transfected by the calcium phosphate method (Umesono and Evans, *Cell*, 57: 1139–46 (1989) and Berger et al., *J. Steroid Biochem. Molec. Biol.*, 41: 733–38 (1992)) by using 10 ng of a pRS (Rous sarcoma virus promoter) receptor-expression plasmid vector, 50 ng of the reporter luciferase (LUC) plasmid, 50 ng of pRSβ-GAL(β-galactosidase) as an internal control, and 90 ng of carrier plasmid, pGEM. Cells were transfected for 6 h and then washed to remove the precipitate. The cells were then incubated for 36 h with or without retinoid. After the transfection, all subsequent steps were performed on a Beckman Biomek Automated Workstation. Cell extracts were prepared, then assayed for luciferase and β-galactosidase activities, as described by Berger et al. (1992). All determinations were performed in triplicate in two independent experiments and were normalized for transfection efficiency by using β-galactosidase as the internal control. Retinoid activity was normalized relative to that of alltrans-retinoic acid and is expressed as potency (EC50), which is the concentration of retinoid required to produce 50% of the maximal observed response, and efficacy (%), which is the maximal response observed relative to that of all-trans-retinoic acid at $10^{-5}$M. The data obtained is the average of at least four independent experiments. Efficacy values less than 5% are not statistically different than the 0% background. Compounds with an efficacy of less than 20% at concentrations of $10^{-5}$M are considered to be inactive. At higher concentrations of compound, such as $10^{-4}$M, these compounds are generally toxic to cells and thus the maximal efficacy at $10^{-5}$M is reported in the tables and figures contained herein.

Figure 2:
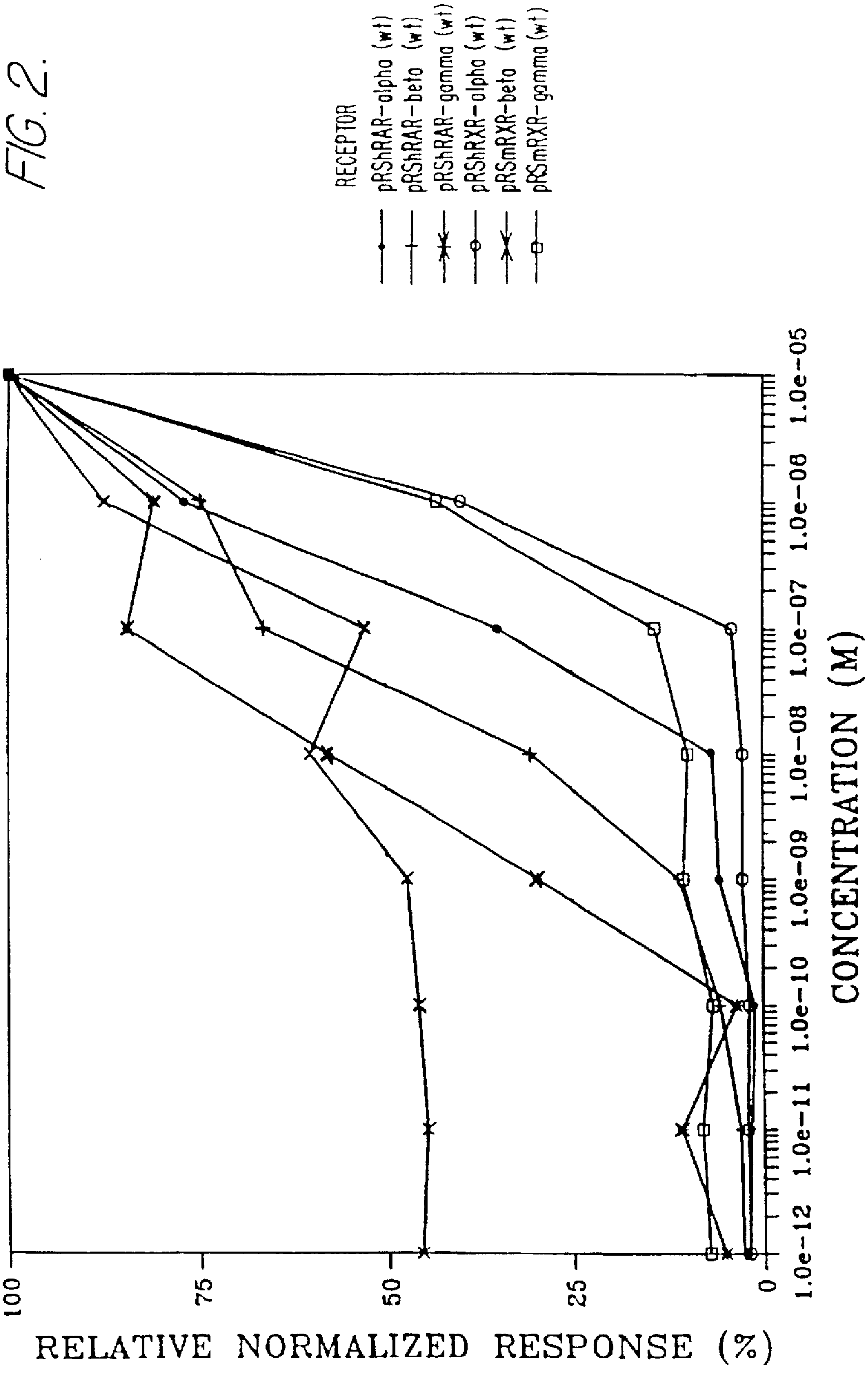
FIG. 2 presents the standardized dose response profiles showing the transactivation of RAR and RXR isoforms by all-trans-retinoic acid.
Figure 3:
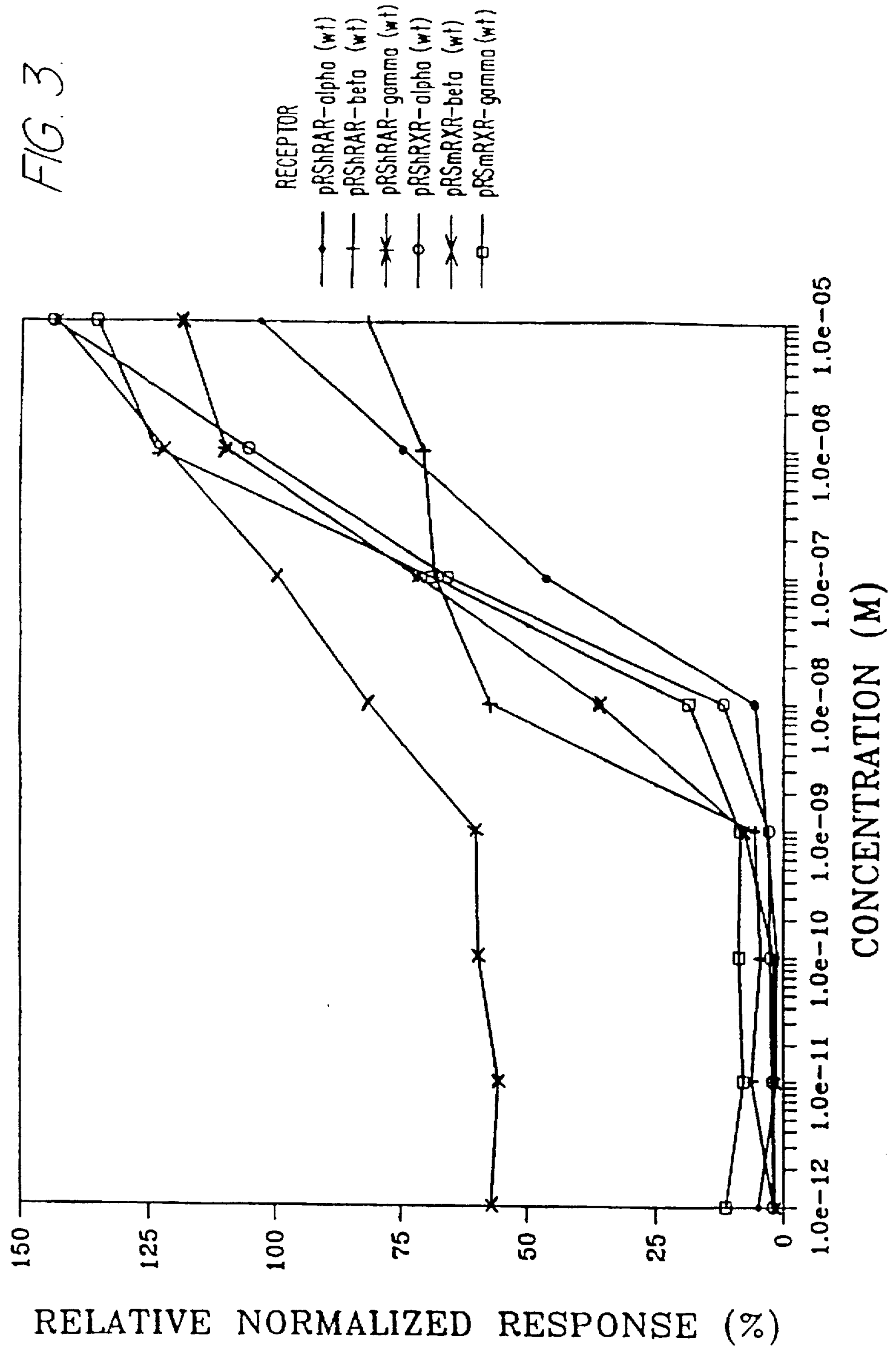
FIG. 3 presents the standardized dose response profiles showing the transactivation of RAR and RXR isoforms by 9-cis-retinoic acid.
Figure 4:
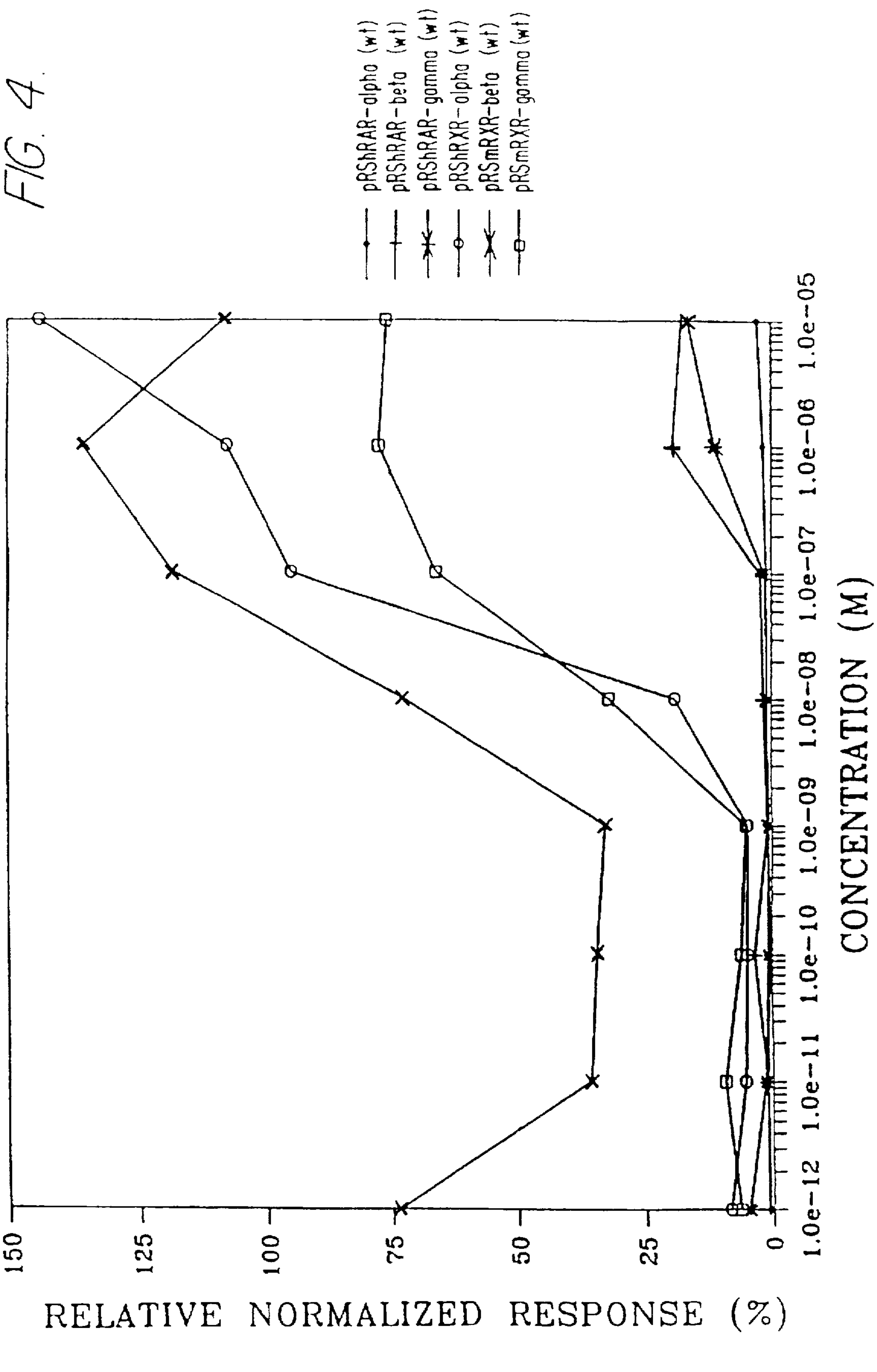
FIG. 4 presents the standardized dose response profiles showing the transactivation of RAR and RXR isoforms by 3-methyl-TTNEB.
Figure 5:
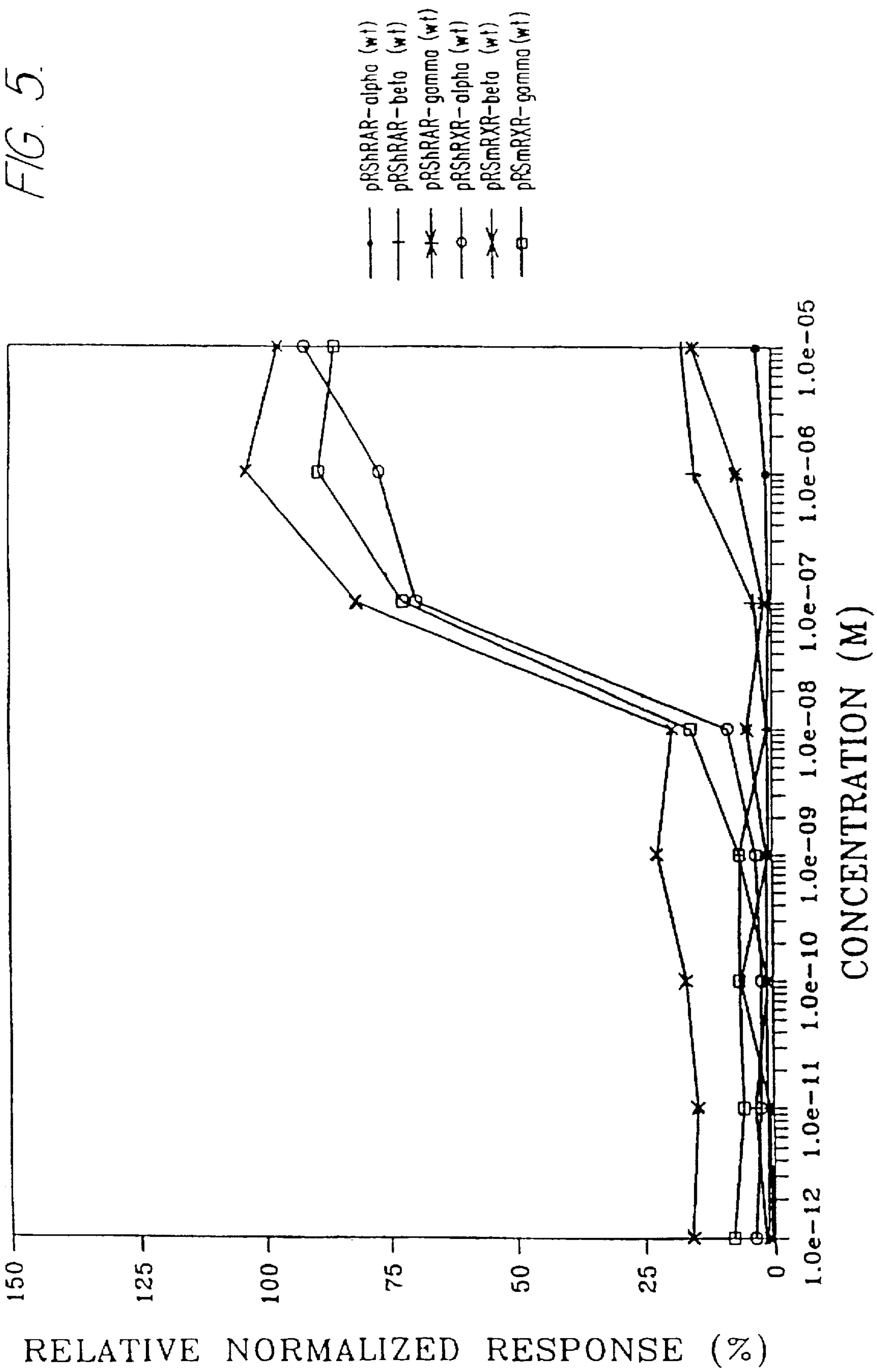
FIG. 5 presents the standardized dose response profiles showing the transactivation of RAR and RXR isoforms by 3-bromo-TTNEB.
Figure 6:
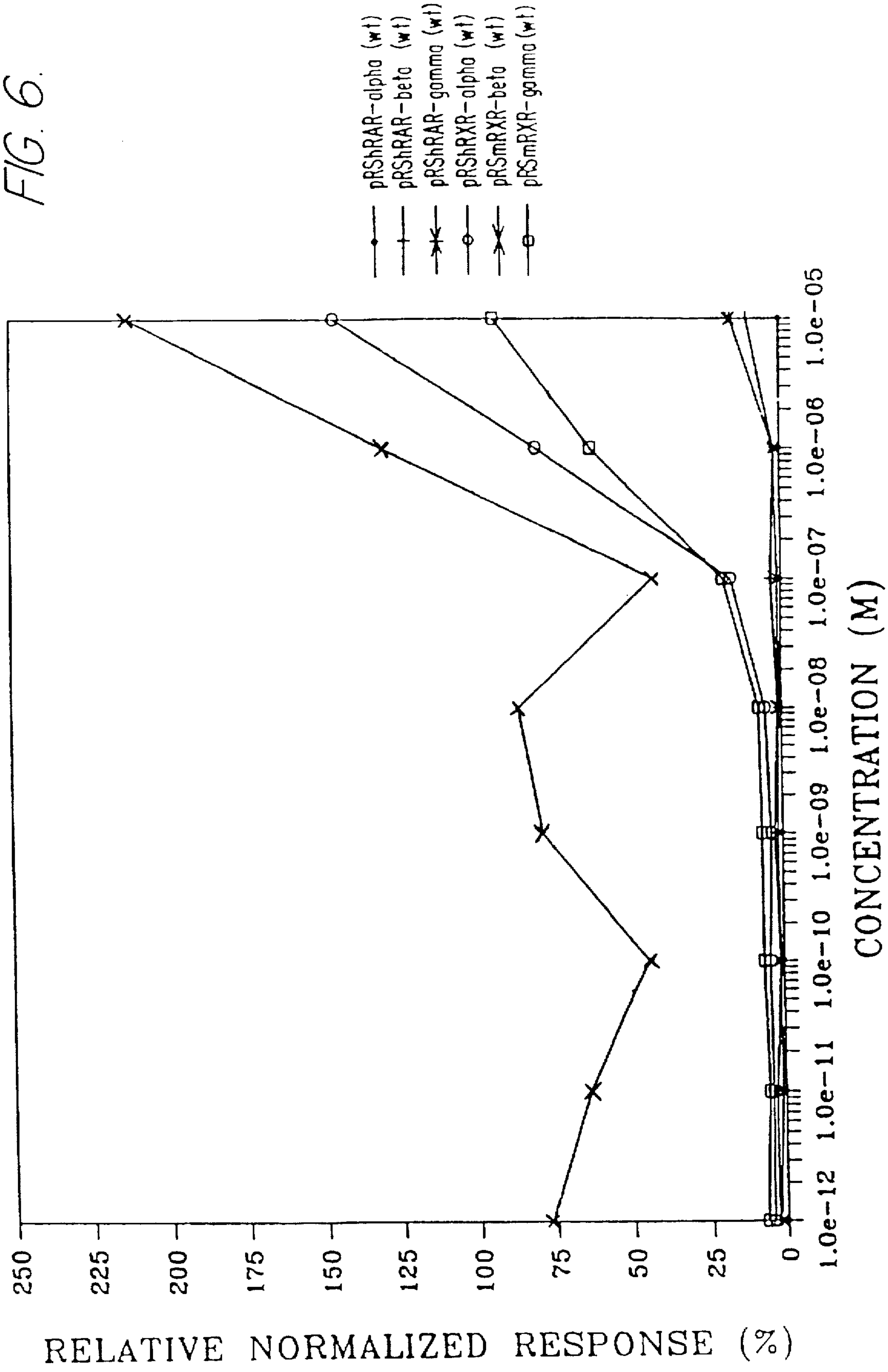
FIG. 6 presents the standardized dose response profiles showing the transactivation of RAR and RXR isoforms by 3-methyl-TTNCHBP.
Figure 7:
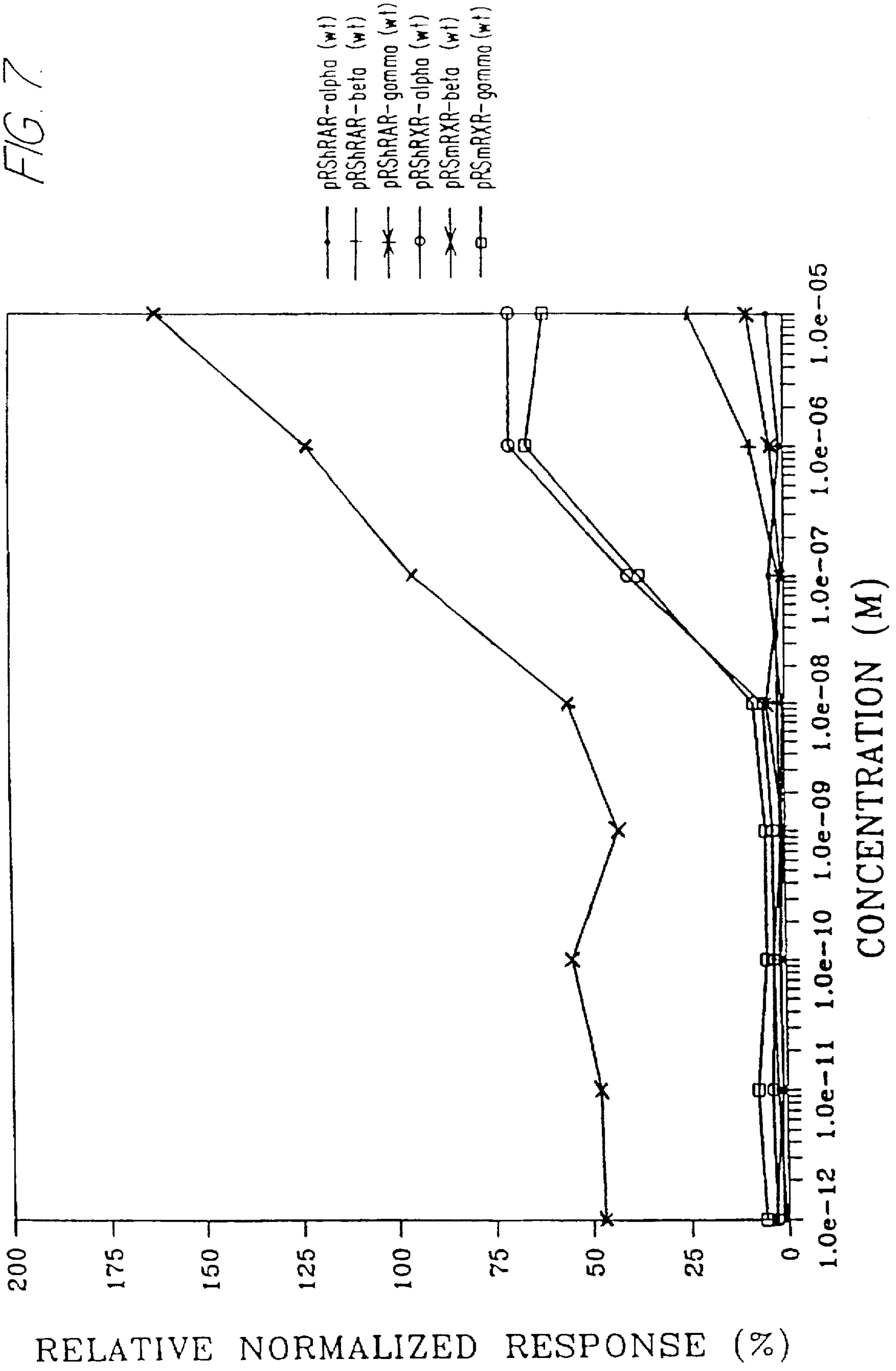
FIG. 7 presents the standardized dose response profiles showing the transactivation of RAR and RXR isoforms by 3-methyl-TTNEHBP.

The synthetic retinoid compound 3-methyl-TTNCB, as described above, was evaluated for its ability to regulate gene expression mediated by retinoid receptors. As shown in FIG. 1, this compound is capable of activating members of the RXR subfamily, i.e., RXRα, RXRβ, and RXRγ, but clearly has no significant activity for members of the RAR subfamily, ie., RARα, RARβ, and RARγ. Assays using all-trans-retinoic acid (FIG. 2) and 9-cis-retinoic acid (FIG. 3) were run for reference, and demonstrate that these retinoic acid isomers activate members of both the RAR and RXR subfamilies.

Potency and efficacy were calculated for the 3-methyl-TTNCS compound, as summarized in the following table. For reference, the data for 9-cis-retinoic acid are also included.

TABLE 1

| | Potency (nM) | Efficacy |
|---|---|---|
| 3-Methyl-TTNCB | | |
| RXRα | 330 | 130% |
| RXRβ | 200 | 52% |
| RXRγ | 260 | 82% |
| RARα | >10,000 | <2% |
| RARβ | >10,000 | <4% |
| RARγ | >10,000 | <4% |
| 9-cis-retinoic acid | | |
| RXRα | 150 | 140% |
| RXRβ | 100 | 140% |
| RXRγ | 110 | 140% |
| RARα | 160 | 100% |
| RARβ | 5 | 82% |
| RARγ | 47 | 120% |

As shown by the data in Table 1, 3-methyl-TTNCB readily and at low concentrations activates RXRs. Further, 3-methyl-TTNCB is more potent an activator of RXRs than RARs, and preferentially activates RXRs in comparison to RARs, in that much higher concentrations of the compound are required to activate the RARs. In contrast, 9-cis-retinoic acid does not preferentially activate the RXRs, as also shown in Table 1. Rather, 9-cis-retinoic acid activates the RARβ and RARγ isoforms at lower concentrations and more readily than the RXRβ and RXRγ isoforms, and has substantially the same, within the accuracy of the measurement, activity for the RARα isoform in comparison to the RXRα isoform.

An extract reported to contain 9-cis-retinoic acid has previously been reported as at least 10-fold more potent in inducing RXRα than RARα (Heyman et al., *Cell*, 68: 397,399 (Jan. 24, 1992)). Presently available data indicate that 9-cis-retinoic acid does not preferentially activate RXRs in comparison to RARs, as shown and discussed above. The compounds of this invention preferentially activate RXRs in comparison to RARs, and are preferably at least three times more potent as activators of RXRs than RARs.

Potency and efficacy have also been calculated for the 3-methyl-TTNEB, 3-bromo-TTNEB, 3-methyl-TTNCHBP, 3-methyl-TTNEHBP, TPNEP, and TPNCP compounds, as summarized below in Table 2.

TABLE 2

| | Potency (nM) | Efficacy |
|---|---|---|
| 3-Methyl-TTNEB | | |
| RXRα | 40 | 83% |
| RXRβ | 21 | 102% |

TABLE 2-continued

| | Potency (nM) | Efficacy |
|---|---|---|
| RXRγ | 34 | 80% |
| RARα | >10,000 | 6% |
| RARβ | >10,000 | 17% |
| RARγ | >10,000 | 19% |
| 3-Bromo-TTNEB | | |
| RXRα | 64 | 88% |
| RXRβ | 54 | 49% |
| RXRγ | 52 | 71% |
| RARα | >10,000 | 3% |
| RARβ | >10,000 | 18% |
| RARγ | >10,000 | 15% |
| 3-Methyl-TTNCHBP | | |
| RXRα | 1100 | 113% |
| RXRβ | 1100 | 155% |
| RXRγ | 300 | 128% |
| RARα | >10,000 | <2% |
| RARβ | >10,000 | 7% |
| RARγ | >10,000 | 17% |
| 3-Methyl-TTNEHBP (63) | | |
| RXRα | 140 | 125% |
| RXRβ | 71 | 121% |
| RXRγ | 48 | 163% |
| RARα | >10,000 | <2% |
| RARβ | 1,900 | 25% |
| RARγ | >10,000 | 10% |
| TPNEP (58) | | |
| RXRα | 5 | 75% |
| RXRβ | 5 | 138% |
| RXRγ | 6 | 100% |
| RARα | >10,000 | <2% |
| RARβ | >10,000 | <2% |
| RARγ | 1,500 | 24% |
| TPNCP (62) | | |
| RXRα | 4 | 63% |
| RXRβ | 4 | 93% |
| RXRγ | 3 | 49% |
| RARα | >10,000 | <2% |
| RARβ | >10,000 | <2% |
| RARγ | >10,000 | <2% |

As shown by the data in Table 2, 3-methyl-TTNEB, 3-bromo-TTNEB, 3-methyl-TTNCHBP, 3-methyl-TTNEHBP, TPNEP, and TPNCP each readily and preferentially activate the RXRs, and are more potent as activators of RXRs than of RARs. The diminished activity of these compounds for the RARs in comparison to the RXRs is also shown for some of these compounds in FIGS. 4–7.

Potency and efficacy for the n-alkyl cyclohexenyl nonatetranoic acid derivative compounds 74, 75, and 77 are as shown below in Table 3, and for compounds 100, 104, 110, 123, and 128 in Table 3A. As shown, these compounds also preferentially activate RXRs, in comparison to RARs. Other geometric isomers of these compounds have also been found to exhibit this same activity.

TABLE 3

| | Potency (nM) | Efficacy |
|---|---|---|
| Compound 74 | | |
| RXRα | 11 | 78% |
| RXRβ | 6 | 91% |
| RXRγ | 12 | 85% |
| RARα | >10,000 | <2% |
| RARβ | 38 | 50% |

TABLE 3-continued

| | Potency (nM) | Efficacy |
|---|---|---|
| RARγ | 37 | 61% |
| Compound 75 | | |
| RXRα | 21 | 100% |
| RXRβ | 18 | 142% |
| RXRγ | 11 | 106% |
| RARα | >10,000 | <2% |
| RARβ | 180 | 58% |
| RARγ | 150 | 119% |
| Compound 77 | | |
| RXRα | 16 | 75% |
| RXRβ | 11 | 99% |
| RXRγ | 9 | 71% |
| RARα | >10,000 | <2% |
| RARβ | 140 | 63% |
| RARγ | 170 | 44% |

TABLE 3A

| | Potency (nM) | Efficacy |
|---|---|---|
| Compound 100 | | |
| RXRα | 123 | 63% |
| RXRβ | 71 | 54% |
| RXRγ | 106 | 72% |
| RARα | >10,000 | 9% |
| RARβ | >10,000 | 5% |
| RARγ | >10,000 | 4% |
| Compound 104 | | |
| RXRα | 5 | 75% |
| RXRβ | 13 | 133% |
| RXRγ | 7 | 85% |
| RARα | >10,000 | 7% |
| RARβ | >10,000 | 5% |
| RARγ | 144 | 28% |
| Compound 110 | | |
| RXRα | 85 | 79% |
| RXRβ | 70 | 73% |
| RXRγ | 198 | 87% |
| RARα | >10,000 | 9% |
| RARβ | 446 | 29% |
| RARγ | 1772 | 37% |
| Compound 123 | | |
| RXRα | 24 | 90% |
| RXRβ | 21 | 105% |
| RXRγ | 24 | 97% |
| RARα | >10,000 | 11% |
| RARβ | 75 | 55% |
| RARγ | 283 | 49% |
| Compound 128 | | |
| RXRα | 11 | 108% |
| RXRβ | 22 | 154% |
| RXRγ | 10 | 115% |
| RARα | >10,000 | 12% |
| RARβ | 180 | 40% |
| RARγ | 309 | 37% |

The selective activity of the compounds of this invention for Retinoid X Receptors is not exhibited by other known compounds. For example, compounds such as those described in U.S. Pat. No. 4,833,240 (Maignan et al.) appear structually similar to the compounds of this invention, but lack a functional group (such as methyl, ethyl, isopropyl, bromo, chloro, etc.) at the 3-position. Such compounds have little or no potency and lack any selectivity for RXRs.

For example, a representative compound of U.S. Pat. No. 4,833,240 (Maignan) is shown below, along with the compound 3-methyl-TTNCB of this invention.

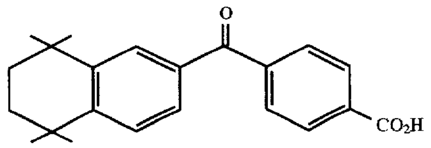

Maignon Ex. II

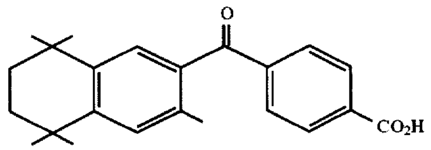

3-methyl-TTNCB

The potency and efficacy of the Maignon compound and that of 3-methyl-TTNCB are summarized below:

| | Potency (nM) | Efficacy |
|---|---|---|
| Maignon Ex. II | | |
| RXRα | 3,000 | 82% |
| RXRβ | 3,000 | 44% |
| RXRγ | 3,000 | 64% |
| RARα | >10,000 | 11% |
| RARβ | 1,900 | 58% |
| RARγ | 2,000 | 56% |
| 3-Methyl-TTNCB | | |
| RXRα | 330 | 130% |
| RXRβ | 200 | 52% |
| RXRγ | 260 | 82% |
| RARα | >10,000 | <2% |
| RARβ | >10,000 | <4% |
| RARγ | >10,000 | <4% |

As shown, the Maignon compound is virtually inactive and shows no selectivity for RXRs. In contrast, the compounds of this invention such as 3-methyl-TTNCB, which have a substituant at the 3-position, are potent activators of RXRs and exhibit the unexpected RXR selectivity shown in Table 1 (as well as Tables 2, 3, and 3A) and discussed above.

It can be expected that synthetic retinoid ligands, such as those exemplified in Tables 1, 2, 3, and 3A which preferentially affect some but not all of the retinoid receptor isoforms, can, in pharmacological preparations, provide pharmaceuticals with higher therapeutic indices and a better side effect profile than currently used retinoids. For example, the compounds of the present invention have been observed to be less irritating to the skin than previously known retinoids.

Figure 8:
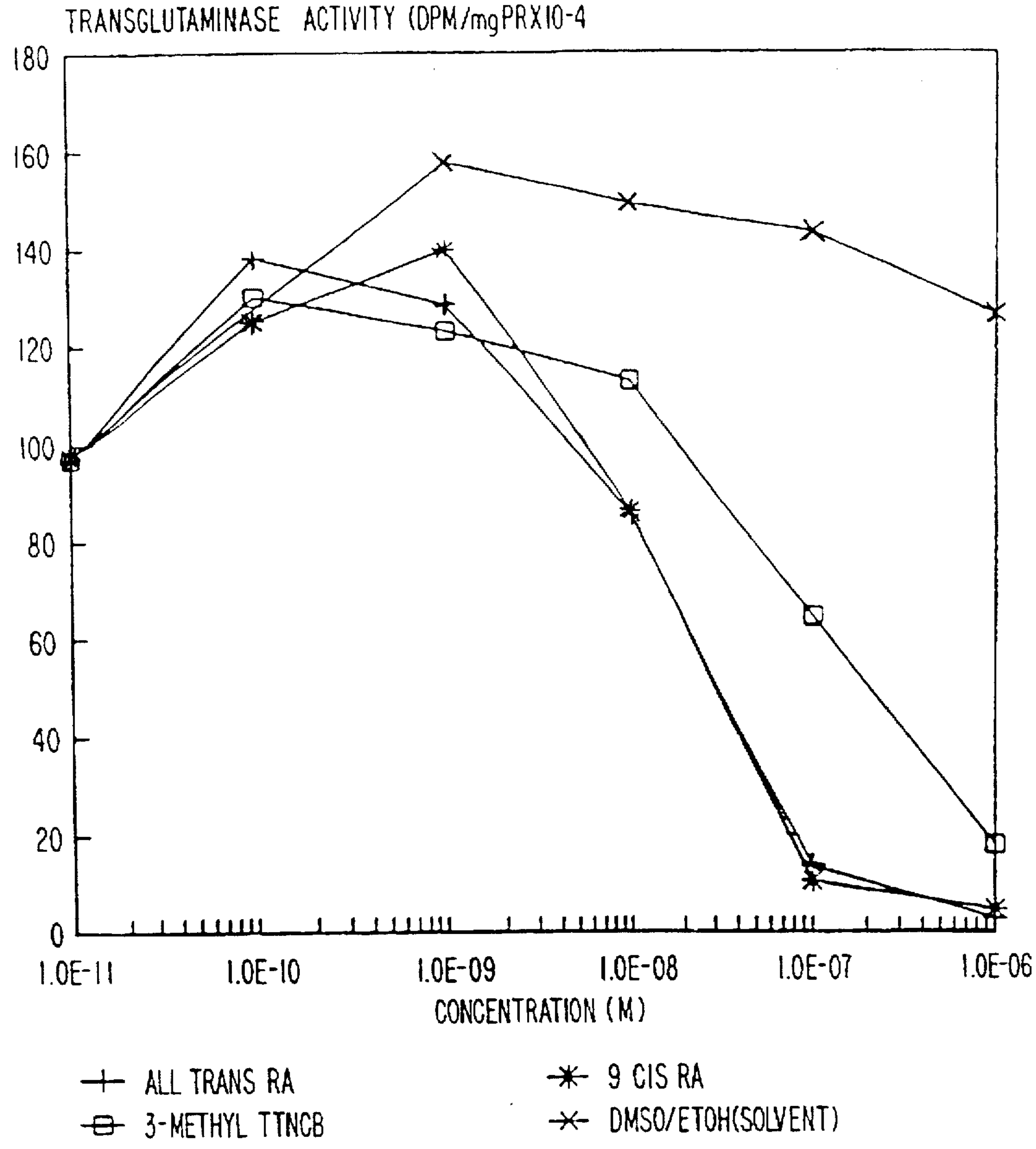
FIG. 8 presents the inhibition of transglutaminase activity by 9-cis-retinoic acid, all-trans-retinoic acid, and 3-methyl-TTNCB.

The retinoid compounds of this invention are useful for the treatment of certain dermatological conditions such as keratinization disorders, i.e., differentiation/proliferation. A standard assay to determine the activity of these compounds is the measurement of the enzymatic activity for transglutaminase; this is a measure of the antiproliferative action of retinoids. Retinoids have been shown to inhibit the pathway of differentiation, which is indicated by a decrease in several biochemical markers that are associated with the expression of squamous cell phenotype, such as transglutaminase. (Yuspa et al., *Cancer Research*, 43: 5707–12 (1983)). As can be seen from FIG. 8, the 3-methyl-TTNCB compound is capable of inhibiting transglutaminase activity and inhibits 50% of the enzyme activity at $1\times10^{-7}$M.

The retinoid compounds of this invention have been demonstrated in in vitro tests to block (or antagonize) AP-1 activity, a set of oncogenes which drive cellular proliferation. Many proliferative disorders are the results of oncogenes/oncogene activation, and therefore a compound which blocks the AP-1 oncogene pathway can be used to treat diseases associated with proliferative disorders including cancers, inflammatory diseases, psoriasis, etc. For example, the compound 3-methyl-TTNEB was evaluated using the co-transfection assay in which HeLa cells were co-transfected with a plasmid expressing RXRA under the control of a constitutive promoter, and a plasmid which expresses the reporter enzyme luciferase under the control of a conditional promoter (collagenase) containing an AP-1 responsive element. E.g., Angel et al., *Mol. Cell. Biol.*, 7: 2256 (1987); Lafyatis et al., *Mol. Endocrinol.*, 4: 973 (1990). Following AP-1 activation, the assay results showed antagonism of AP-1 activity by the 3-methyl-TTNEB compound via RXRα in a dose-dependent manner. Other compounds of this invention have shown similar antagonism of AP-1 activity. These results demonstrate that RXR-selective compounds such as 3-methyl-TTNEB can be used as antiproliferatives to limit cell growth and treat diseases associated with hyperproliferation.

Figure 9:
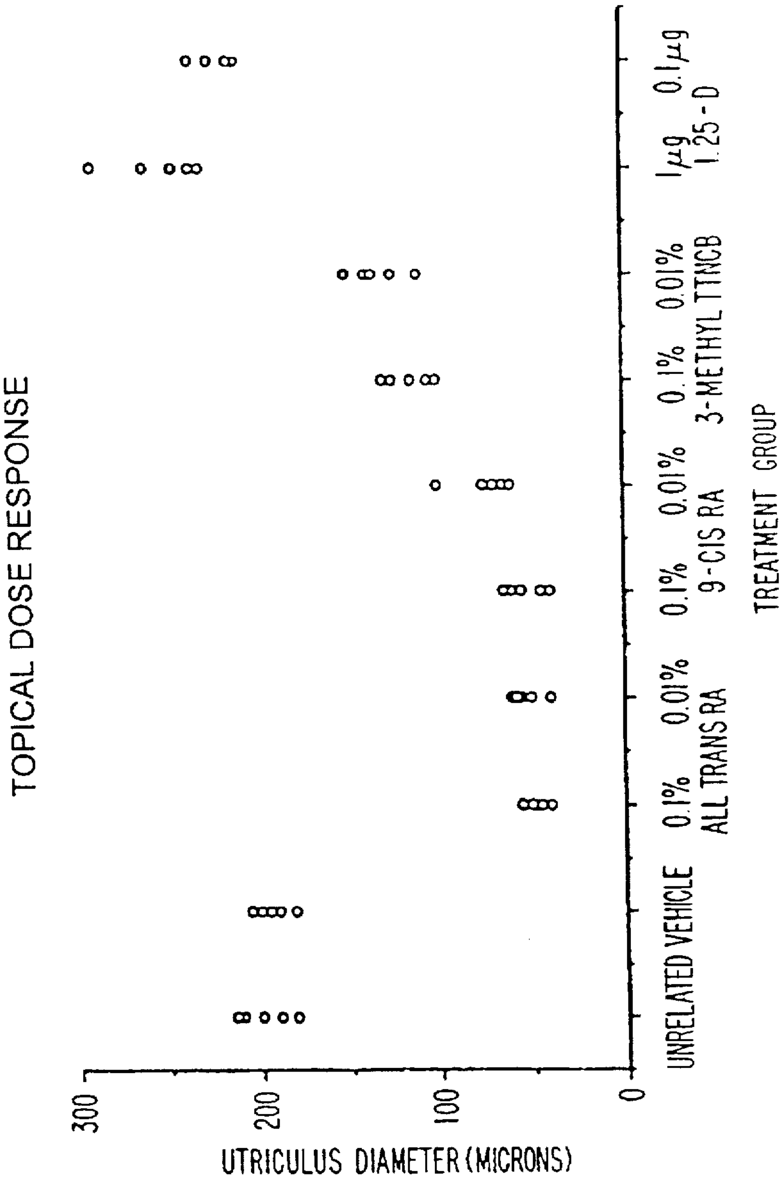
FIG. 9 presents the Topical Dose Response, based on the test on Rhino mice, for 9-cis-retinoic acid, all-trans-retinoic acid, 3-methyl-TTNCB, and 1,25-dihydroxy Vitamin D.

The compounds of this invention also exhibit good comedolytic activity in the test on Rhino mice described by Kligman et al. (*J. of Inves. Derm.*, 73: 354–58 (1979)) and Mezick et al. (*J. of Inves. Derm.*, 83: 110–13 (1984)). The test on Rhino mice has been a model for screening comedolytic agents. The activity of the 3-methyl-TTNCB retinoid compound, as well as 9-cis and all-transretinoic acid is shown in FIG. 9. A 0.1% solution of 3-methyl-TTNCB is capable of inhibiting the utriculi diameter by approximately 50%. It has also been observed that 3-methyl-TTNCB is less irritating to the skin of Rhino mice than 9-cis- or all-trans-retinoic acid.

The co-transfection assay allows examination of the ability of a compound to modulate gene expression in a retinoid receptor dependent fashion. To examine the ability of the compounds of this invention to directly interact with the receptors, we have examined the ligand binding properties of all six retinoid receptors. The receptors were expressed employing a baculovirus expression system in which we have demonstrated that RxRα binds 9-cis-retinoic acid with high effinity (Heyman et al., *Cell*, 68: 397 (1992)). The binding parameters of receptors expressed in baculovirus systems and mammaliam systems are essentially identical.

The synthetic retinoids of the current invention have also been tested using radioligand displacement assays. By testing the abilities of various synthetic retinoids to compete with the radiolabeled retinoic acid for binding to various receptor isoforms, the ability of the compounds to directly interact with the receptor can be examined, and the relative dissociation constant for the receptor itself can be determined. This is an important supplementary analysis to the co-transfection assay since it can detect different properties/determinants of retinoid activity than are measured in the co-transfection assay. These determinants/differences in the two assay systems may include (1) activating or inactivating metabolic alterations of the test compounds, (2) binding to serum proteins which could alter the free concentration or other properties of the test compound, (3) differences in cell permeation among test compounds, (4) intrinsic differences in the affinity of the test compounds for the receptor proteins, i.e., in $K_d$, can be directly measured, and (5) conformational changes produced in the receptor after binding of the test compound, reflected in the effects on reporter gene expression; (i.e., a functional measurement of receptor activation).

The 3-methyl-TTNCB compound is capable of displacing $^3$H-9-cis-retinoic acid bound to the RXRs, but is not capable of displacing radiolabeled ligand that is bound to the RARs. This indicates that the 3-methyl-TTNCB compound preferentially binds RXRs in comparison to RARs, a property which would be expected of a ligand selective for the RXRs. The $K_d$ values were determined by application of the Cleng-Prusoff equation. These values were based on a determination of the $IC_{50}$ value as determined graphically from a log-logit plot of the data.

Binding data were obtained for various compounds using the method discussed in Wecksler & Norman, *Anal. Biochem.*, 92: 314–23 (1979). Results are shown below in Table 4.

TABLE 4

| | Binding ($Kd_{50}$ nM) |
|---|---|
| 3-Methyl-TTNCB | |
| RXRα | 350 |
| RXRβ | 230 |
| RXRγ | 365 |
| RARα | >10,000 |
| RARβ | >10,000 |
| RARγ | >10,000 |
| 3-Methyl-TTNEB | |
| RXRα | 41 |
| RXRβ | 20 |
| RXRγ | 22 |
| RARα | 5,500 |
| RARβ | 5,400 |
| RARγ | 3,200 |
| TPNEP (58) | |
| RXRα | 22 |
| RXRβ | 21 |
| RXRγ | 39 |
| RARα | 7,800 |
| RARβ | 4,900 |
| RARγ | 6,000 |
| TPNCP (62) | |
| RXRα | 3 |
| RXRβ | 3 |
| RXRγ | 3 |
| RARα | >10,000 |
| RARβ | >10,000 |
| RARγ | >10,000 |

The compounds in Table 4 were shown to readily and preferentially activate RXRs, and to be more potent as activators of RXRs than of RARs using the co-transfection assay, as discussed above. The binding results in Table 4 show these compounds to also preferentially bind RXRs versus RARs. Taken together the ligand binding properties of these compounds and their ability to selectively modulate members of the RXR subfamily demonstrate the identification of a class of compounds with the unique biological properties. The binding properties and especially the transcriptional activation assays are a good predictor of the pharmacological activity of a compound (Berger et al. (1992)).

It has been recognized that the co-transfection assay provides a functional assessment of the ligand being tested as either an agonist or antagonist of the specific genetic process sought to be affected, and is a predictor of in vivo pharmacology (Berger et al. (1992)). Ligands which do not significantly react with other intracellular receptors, as determined by the co-transfection assay, can be expected to result in fewer pharmacological side effects. Because the co-transfection assay is run in living cells, the evaluation of a ligand provides an early indicator of the potential toxicity of the candidate at concentrations where a therapeutic benefit would be expected.

Processes capable of being modulated by retinoid receptors, in accordance with the present invention, include in vitro cellular differentiation, the regulation of morphogenetic processes including limb morphogenesis, regulation of cellular retinol binding protein (CRBP), and the like. As readily recognized by those of skill in the art, the availability of ligands for the retinoid X receptor makes it possible, for the first time, to elucidate the processes controlled by members of the retinoid X receptor subfamily. In addition, it allows development of assays for the identification of antagonists for these receptors.

The processes capable of being modulated by retinoid receptors, in accordance with the present invention, further include the in vivo modulation of lipid metabolism; in vivo modulation of skin related processes (e.g., acne, psoriasis, aging, wrinkling, and the like); in vivo modulation of programmed cell death (apoptosis); in vivo modulation of malignant cell development, such as occurs, for example, in acute promyelocytic leukemia, mammary cancer, prostate cancer, lung cancer, cancers of the aerodigestive pathway, skin cancer, bladder cancer, and sarcomas; in vivo modulation of premalignant lesions, such as occurs with oral leukoplakia and the like; in vivo modulation of auto-immune diseases such as rheumatoic arthritis; in vivo modulation of fatty acid metabolism; and the like. Such applications can be expected to allow the modulation of various biological processes with reduced occurrence of undesirable side effects such as teratogenic effects, skin irritation, mucosal dryness, lipid disturbances, and the like. In vivo applications can be employed with a wide range of subjects, such as, for example, humans, rodents, sheep, pigs, cows, and the like.

For example, regarding the invivomodulation of lipid metabolism referred to above, apolipoprotein A-1 ("apoAI") is a major protein component of plasma high density lipoprotein (HDL) cholesterol. The circulating level of HDL in humans has been shown to be inversely correlated to the risk of atherosclerotic cardiovascular disease (ASCVD), the leading cause of morbidity and mortality in the United States, with a 3–4% increase in ASCVD for every 1% decrease in HDL cholesterol. Gordon et al., *New Engl. J. Med.*, 321: 1311 (1989). While there are currently no good therapeutic regimes that increase HDL cholesterol, it can be expected that regulating synthesis of apoAI can be utilized to affect plasma concentrations of HDL cholesterol and to decrease the risk of ASCVD. Reuben et al., *Nature*, 353: 265 (1991).

It has been established that regulation of transcription of apoAI is controlled by members of the intracellular receptor superfamily, and further that the apoAI gene transcription start site "A" is a highly selective retinoic acid-responsive element that responds to retinoid X receptors. Rottman et al., *Mol. Cell. Biol.*, 11: 3814–20 (1991). Because RXRs can form heterodimers with transrepressers such as ARP-1 and COUP-TF and transactivators such as HNF-4, and an RXR response element resides in the apoAI promoter, retinoids or ligands which selectively activate members of the RXR family of retinoic acid receptors may regulate apoAI transcription. We have demonstrated in in vivo studies that the ligands of this invention which have selective activity for RXRs can be used to modulate apoAI/HDL cholesterol and to significantly raise plasma HDL levels, as demonstrated in the following example.

EXAMPLE 60

Male Sprague-Dawley rats (160–200 gram) were obtained from Harlan. Animals were fed standard laboratory diets (Harlan/Teklad) and kept in an environmentally controlled animal house with a light period lasting from 6 a.m. to 6 p.m. Animals were treated with drugs prepared as suspensions in olive oil.

To verify that RXR activation can increase plasma apoAI/HDL cholesterol, an initial study was carried out that included dosing rats for 4 days with an RAR-selective compound, all-trans retinoic acid, the non-selective RAR/RXR agonist, 9-cis-retinoic acid, and either of two RXR-selective agents, 3-methyl-TTNCB or 3-methyl-TTNEB. Each drug was administered at a dose of 100 mg/kg, i.p. Positive control groups received olive oil as a vehicle. Twenty-four hours after the last treatment, rats were sacrificed by $CO_2$ inhalation, blood was collected from the inferior vena cava into a tube containing 0.1 ml of 0.15% EDTA and centrifuged at 1500×g for 20 min. at 4° C. Plasma was separated and stored at 4° C. for evaluation of plasma total cholesterol and high density lipoprotein cholesterol (HDL-cholesterol).

Plasma total cholesterol was measured enzymatically utilizing Boeringer Mannheim Diagnostics High Performance Cholesterol Methods with an ABBOTT VP Bichromatic Analyzer. HOL cholesterol was measured after preparation of the HDL-containing fraction by heparin-manganese precipitation of plasma. HDL-cholesterol in this fraction was estimated as mentioned earlier. All HDL separations were checked for contamination by other lipoproteins with agarose gel electrophoresis.

Figure 10:
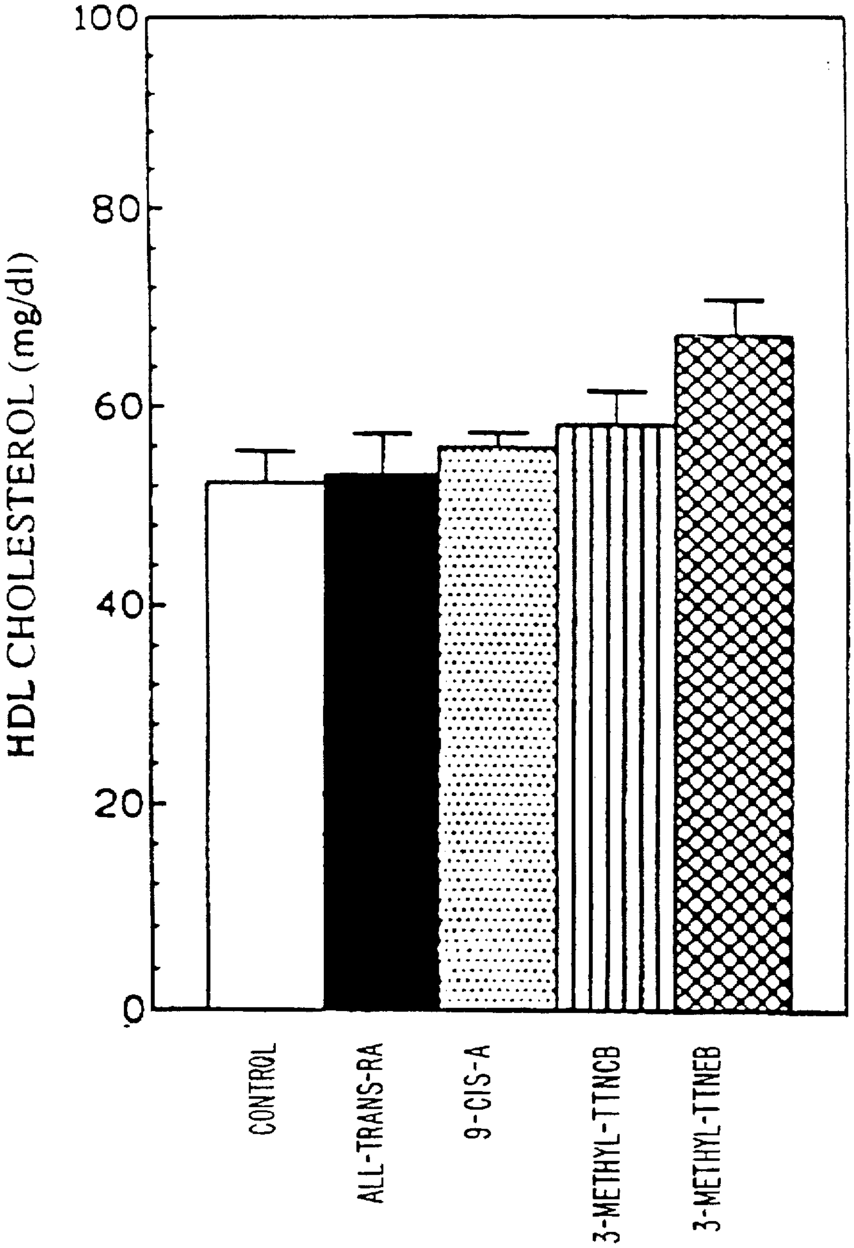
FIG. 10 presents the effect on rat HDL cholesterol of all-trans-retinoic acid, 9-cis-retinoic acid, 3-methyl-TTNCB, and 3-methyl-TTNEB.

The results of this study are shown in FIG. 10. As shown, rats receiving the RXR-selective compounds exhibited substantial and statistically significant increases in HDL levels, particularly when receiving 3-methyl-TTNEB.

Because the RXR-selective ligand 3-methyl-TTNEB was the most efficacious, additional 4 day experiments were conducted with this agent at doses of 0.3, 1, 3, 6, 10, 30, 100, or 300 mg/kg i.p. in 1.0 ml olive oil or 1, 3, 10, 30, 100, 300 mg/kg p.o. in 1.0 ml olive oil for 4 days. An additional 30 day p.o. study was conducted with 10, 30, or 100 mg/kg 3-methyl-TTNEB to determine whether tolerance would develop to its pharmacological actions. For the rats receiving 3-methyl-TTNEB in various doses for four days, it was also observed that 3-methyl-TTNEB increased plasma concentrations of HDL-cholesterol in a dose-dependent manner with significant increases being made at the lowest dose, 0.3 mg/kg i.p. At its optimally efficacious dose, 3-methyl-TTNEB increased plasma HLD-cholesterol concentrations from 58 mg/dl to 95 mg/dl—an increase of greater than 60%. Measurement of total cholesterol showed an increase due to the increase of the HDL-cholesterol fraction. Measurement of triglycerides showed either no change or a slight decrease. The 30-day study with 3-methyl-TTNEB did not indicate development of tolerance to its pharmacological action.

This study demonstrated that t-methyl-TTNEB increased plasma concentrations of HDL-cholesterol in a dose-dependent manner following either i.p. or p.o. administration.

The effect on circulating apoAI of orally administered 3-methyl-TTNEB was also studied. Male Sprague-Dawley rats were treated daily with 3 mg/kg body weight of 3-methyl-TTNEB for four days. Serum samples were taken and analyzed by Western Blot using antisera specific to rat apoAI. The treatment with 3-methyl-TTNEB resulted in a significant increase in circulating apoAI level.

These studies demonstrate that treatment with an RXR specific compound such as 3-methyl-TTNEB increases plasma concentrations of apoAI/HDL cholesterol. Since such animal studies are an accepted predictor of human response, it would therefore be expected that such compounds could be used to therapeutically increase HDL-cholesterol in patients who either have, or are at risk for, atherosclerosis.

Additional in vitro studies were also performed utilizing the co-transfection assay previously described within this application to demonstrate the effect of RXR-selective ligands on regulation of transcription of apoAI, as described in the following example.

EXAMPLE 61

This work focused on studying the transcriptional properties of the retinoid receptors RAR and RXR on a reporter molecule (e.g., luciferase) under control of a basal promoter containing the RXR response element from the apoAI gene ("A" site). Plasmid constructs coding for the various receptors were transfected into a human hepatocyte cell line (HepG-2) along with the reporter plasmid. Reporter plasmids contained multimers of the apoAI "A" site (−214 to −192 relative to transcription start site) shown to bind RXR. Widom et al., *Mol. Cell. Biol.* 12: 3380–89 (1992); Ladias & Karathanasis, *Science* 251: 561–65 (1991). After transfection, treatment, harvest, and assay, the data obtained was normalized to transfected beta-galactosidase activity so as to control for transfection efficiency. The results demonstrated activation in the system with the RXR-specific ligands 3-methyl-TTNCB and 3-methyl-TTNEB, in a concentration-dependent fashion demonstrating that the RXR specific ligands could regulate the transcriptional properties via the "A" site from the apoAI gene. These compounds had no effect when RAR was used in the transfection, demonstrating receptor specificity. The transcriptional regulation by RXR was dependent on the presence of the hormone response element.

These in in vivo and in vitro studies demonstrate that the RxR-selective compounds of this invention can be used to elevate ApoAI/HDL cholestrerol and in the therapeutic treatment of related cardiovascular disorders.

Regarding the modulation of programmed cell death (apoptosis), the retinoid compounds of this invention have been demonstrated to induce apoptosis in particular cell types including leukemic cells and squamous epithelial carcinomas. Normally in cells there is a fine balance between cellular processes of proliferation, differentiation, and cell death, and compounds which affect this balance may be used to treat certain cancers. Specifically, the ability of 3-methyl-TTNEB to induce differentiation, inhibit proliferation, and induce apoptosis in an acute promyelucytic leukemia cell line, HL60, was studied. Cellular proliferation was measured by a thymidine incorporation assay (Shrivastav et al., *Cancer Res.*, 40: 4438 (1980)), and 3-methyl-TTNEB was found to have no effect on cellular proliferation. This contrasts all-trans-retinoic acid, which inhibits thymidine incorporation. Cellular differation was measured by the ability of the cells to reduce nitroblue tetrazolium (NBT) (Breitman et al., *Proc. Natl. Acad. Sci.*, 77: 2936 (1980)), and 3-methyl-TTNEB was found not to induce undue differentiation. The $EC_{50}$ for 3-methyl-TTNEB mediated differentiation was >1000 μM, compared to 2.0 μM for all-trans-retinoic acid. However, 3-methyl-TTNEB was found to induce transglutaminase activity in the HL6O cells (Murtaugh et al., *J. Biol. Chem.* 258: 11074 (1983)) in a concentration-dependent manner, which correlates with the induction of apoptosis or programmed cell death. It was further found that 3-methyl-TTNEB was able to induce apoptosis as measured by DNA fragmentation and morphological changes. Other retinoid compounds of this invention showed similar results, and similar results were also shown in other cell lines such as squamous epithelial cell lines and ME180 cells, a human cervical carcinoma.

These results show that RXR specific compounds such as 3-methyl-TTNEB induce apoptosis with a minimal direct effect on inhibition of proliferation and differentiation induction. Compounds which are capable of inducing apoptosis have been shown to be effective in cancer chemotherapy (e.g., anti-hormonal therapy for breast and prostate cancer).

In contrast, in another cell type retinoids have been shown to inhibit activation driven T-cell apoptosis and 9-cis-retinoic acid was approximately ten fold more potent than all-trans-retinoic acids (Ashwell et al., *Proceedings National Academy of Science,* Vol. 90, p. 6170–6174 (1993)). These data imply that RXRs are involved in this event. Thus retinoids could be used to block and/or immunomodulate T-cell apoptosis associated with certain disease states (e.g., AIDS).

It has been surprisingly found that the administration of a ligand which has specific activity for RXRs but essentially no activity for RARs, in combination with a ligand that has specific activity for RARS but not RXRs, provides a cellular response at extremely low dosages, dosages at which the ligands individually provide no significant response. Specifically, the concentration-related effect of an RXR-specific ligand and a RAR-specific ligand on proliferation of a myeloma cell line (RPMI 8226) was studied in in vitro studies using a thymidine incorporation assay. This assay examines the incorporation of radiolabeled thymidine into DNA, and by determining the ability of a compound to inhibit thymidine incorporation into DNA, provides a measure of cell proliferation. (L. M. Bradley, *Selected Methods in Cellular Immunology,* Ch. 10.1, pp. 235–38, Mishell & Shiigi (eds.), Freeman & Co., New York, 1980). Compounds which inhibit cell proliferation have well-known utility in the treatment of certain cancers.

Figure 11:
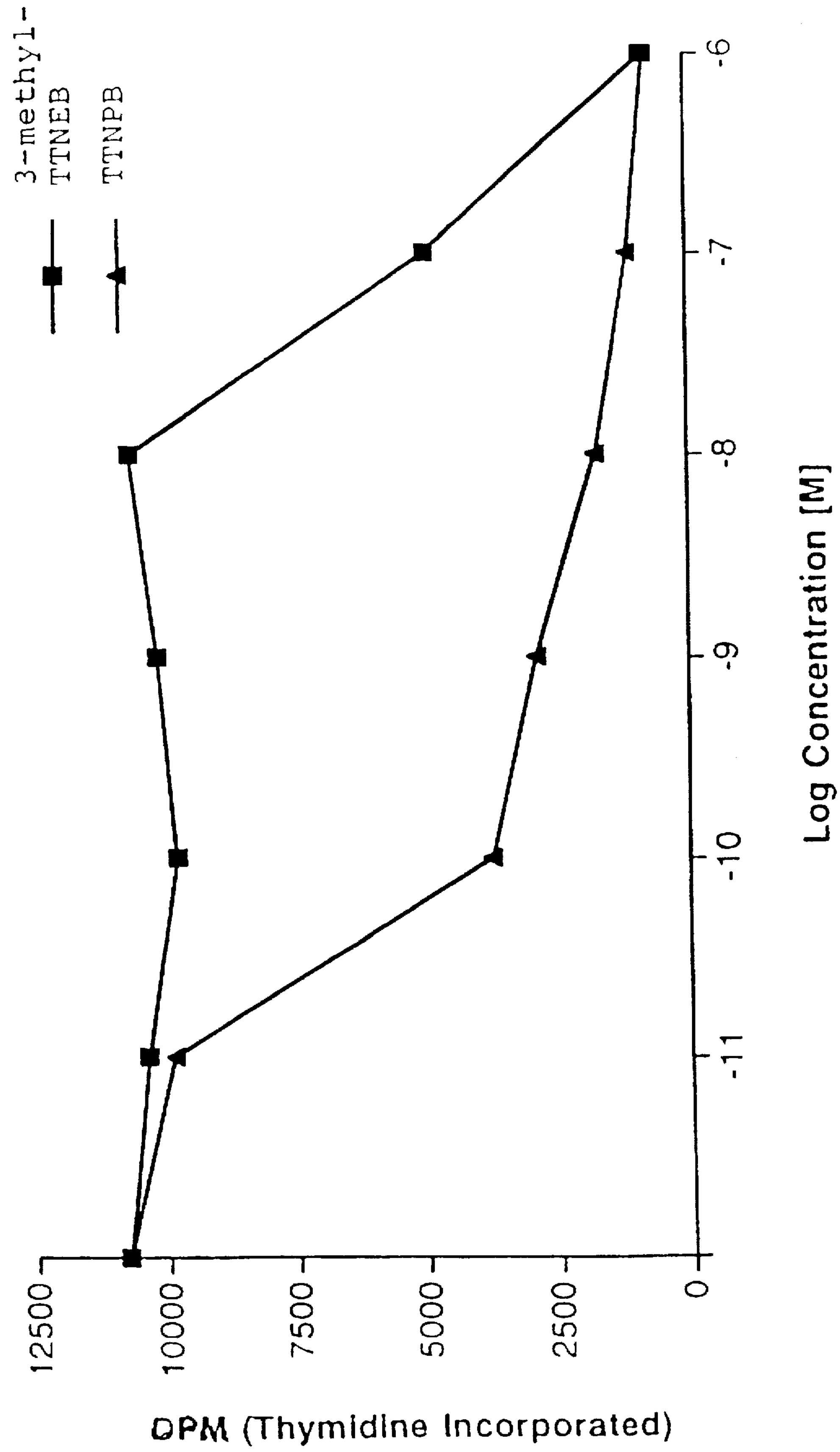
FIG. 11 presents the concentration-related effect of 3-methyl-TTNEB and TTNPB individually on incorporation of radiolabeled thymidine into DNA.

As shown previously (Table 2), 3-methyl-TTNEB activates members of the RXR subfamily and has no significant activity for members of the RAR subfamily. Examination of the effects of 3-methyl-TTNEB on the proliferation of myeloma cells show a concentration dependent inhibition of thymidine incorporation. The $IC_{50}$ (the concentration of 3-methyl-TTNEB required to produce 50% inhibition of the maximal response) is $10^{-7}$M, as shown in FIG. 11. Concentrations less than $10^{-8}$M provide essentially no effect on cell proliferation, as also shown in FIG. 11.

It is well known that the compound TTNPB activates members of the RAR subfamily and has no significant activity for members of the RXR subfamily. The compound TTNPB is shown below, and its activity is shown in Table 5.

TABLE 5

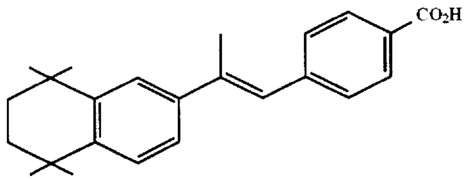

TTNPB

| TTNBP | Potency (nM) | Efficacy |
|---|---|---|
| RXRα | >10,000 | <5% |
| RXRβ | >10,000 | <5% |
| RXRγ | >10,000 | <5% |
| RARα | 52 | 30 |
| RARβ | 4 | 40 |
| RARγ | 0.4 | 50 |

The effect of TTNPB on cell proliferation is shown in FIG. 11. The $IC_{50}$ value of TTNPB is about $5\times10^{-11}$M, and a concentration of less than $10^{-11}$M produces essentially no effect on cell proliferation.

However, it has been found that when 3-methyl-TTNEB and TTNPB are present together, each at a concentration where the compound alone produces substantially no anti-proliferative effect, the combination of the two compounds effectively blocks cell proliferation. The combination of the two compounds appears to produce a greater than additive, or synergistic, effect.

Figure 12:
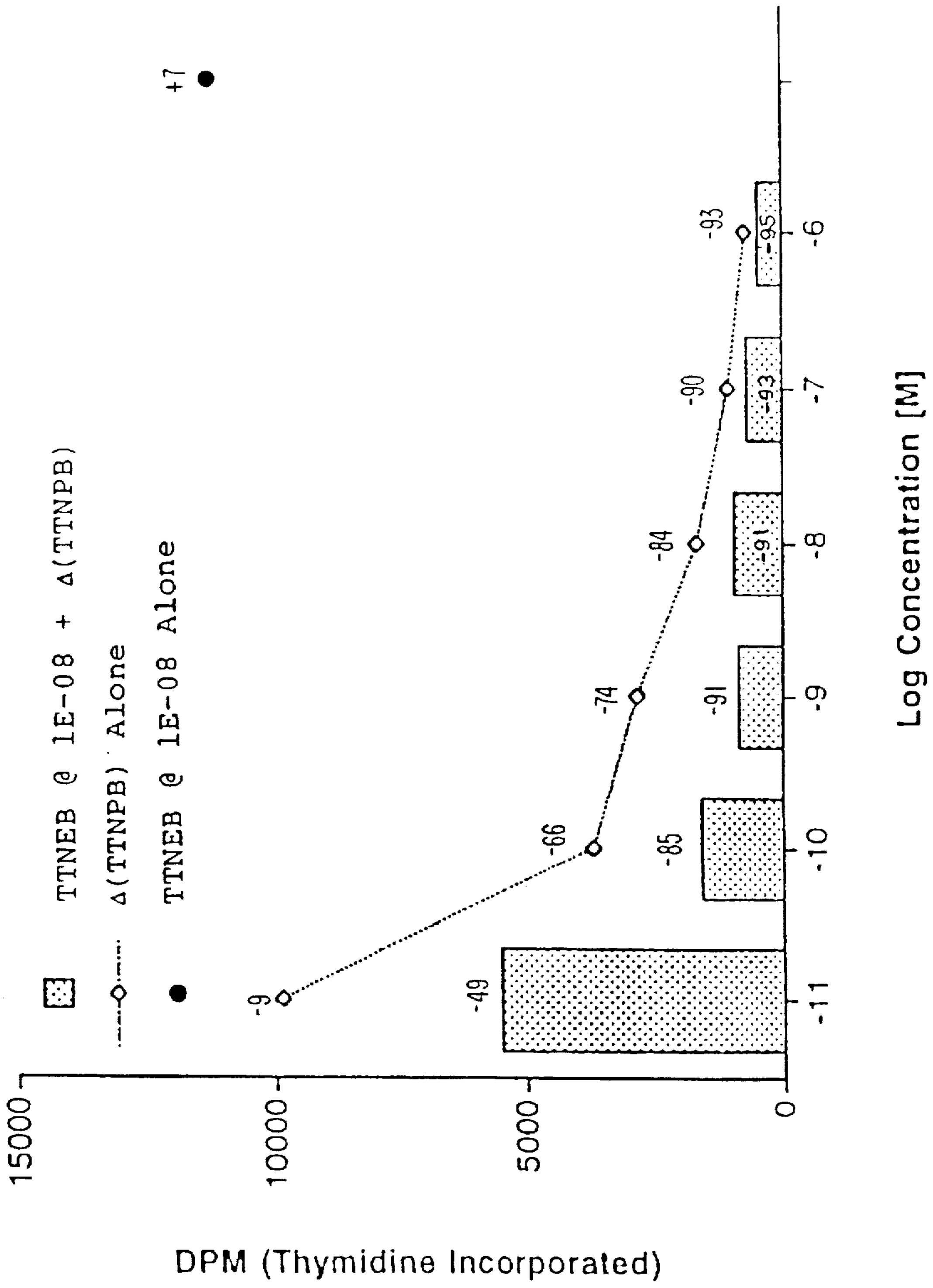
FIG. 12 presents the concentration-related effect of a combination of 3-methyl-TTNEB and TTNPB on incorporation of radiolabeled thymidine into DNA.

For example, as shown in FIG. 12, the presence of TTNPB at a concentration of $10^{-11}$M produces a 9% inhibition on thymidine incorporation. However, combining it with 3-methyl-TTNEB at a concentration of $10^{-8}$M (which results in no effect on cell proliferation) produces a greatly enhanced inhibitory effect of 49%. Likewise, it has also been found that the inhibitory effect of 3-methyl-TTNEB is greatly increased by the presence of TTNPB at a concentration which alone produces no effect.

Since it is well-known that toxic side effects of compounds such as TTNPB are concentration-dependent, the synergistic effect resulting from combining such RAR-specific compounds with RXR-specific compounds can be expected to permit lower dosages that are efficacious and to therefore reduce toxic side effects. For example, in cancer chemotherapy, use of two such compounds, in combination, at relatively low doses can be expected to produce the desired beneficial effect, while minimizing undesired side effects which result at higher doses of the compounds.

In vitro studies utilizing the co-transfection assay have also shown this same synergistic effect. For example, utilizing the co-transfection assay described previously and employing RAR-α and RXR-α and a reporter consisting of the ApoAI response element "A" site in the context of TKLUC (Ladias & Karathanasis, *Science* 251: 561–65 (1991), transfections were performed in HEPG2 cells. In this study, 100 ng of the designated receptor were used and RSVCAT was used as a carrier to keep the amount of RSV promoter constant. All compounds were added at a final concentration of $10^{-7}$M. The RXR specific compound 3-methyl-TTNEB (Table 2, above) and the RAR specific compound, TTNPB (Table 5, above) were utilized. As shown below in Table 6 the relative normalized response observed utilizing the co-transfection assay also demonstrated a synergistic effect when a combination of the two compounds was utilized, compared to the response achieved utilizing the compounds individually.

TABLE 6

| Compound | Reporter Activity (Fold Induction) |
|---|---|
| 3-methyl-TTNEB | 5 |
| TTNPB | 32 |
| 3-methyl-TTNEB + TTNPB | 75 |

As will be discernable to those skilled in the art from the foregoing discussions, the biological response of an RAR selective compound at a given concentration can be synergistically enhanced by combining the compound with an RXR selective compound. Similarly, the biological response of an RXR selective compound can be enhanced by combining the compound with an RAR selective compound. Thus, it becomes possible to achieve a desirable biological response, using a combination of RAR and RXR selective compounds, at lower concentrations than would be the case using the compounds alone. Among the advantages provided by such combinations of RAR and RXR selective compounds are desirable therapeutic effects with fewer side effects. In addition, novel effects that are not obtainable with either agent alone may be achieved by combinations of RAR and RXR selective compounds.

It has been further demonstrated that RXR-specific compounds also synergistically enhance the response of other hormonal systems. Specifically, peroxisome proliferator-activated receptor (PPAR) is a member of the intracellular receptor super family that plays a role in the modulation of lipid homeostasis. PPAR has been shown to be activated by amphipathic carboxylates, such as clofibric acid, and gemfibrizol. These agents, called peroxisome proliferators, have been used in man as hypolipidemic agents. The addition of 9-cis-retinoic acid (a retinoid ligand which activates both RAR and RXR receptors) and clofibric acid to HepG2 cells transfected with RXRA and PPAR expression plasmids, results in the activation of receptor gene which was greater than the sum of the activation with each ligand separately. (Kliewer et al., *Nature* 358: 771 (1992)). Similarly, when the above two receptors were co-transfected into HepG2 cells, the addition of both an RXR-specific ligand (3-methyl-TTNEB) and clofibric acid was found to produce a greater than additive response as determined by activation of a target reporter gene, as shown below in Table 7.

TABLE 7

| Compound | Normalized Response (%) |
|---|---|
| clofibric Acid | 100 |
| 3-methyl-TTNEB | 90 |
| clofibric acid + 3-methyl-TTNEB | 425 |

A similar synergistic effect was observed with RXR and RXR-specific ligands and the Vitamin D receptor (VDR) and its cognate ligands. When RXRβ and VD receptors were co-transfected into CV-1 cells containing a hormone response element, the addition of RXR selective 3-methyl-TTNCB and 1,25-dihydroxy-vitamin D (1,25-D) produced a greater than additive response than was observed for each of the individual ligands, as shown below in Table 8.

TABLE 8

| Compound | Normalized Response (%) |
|---|---|
| 1,25-D | 100 |
| 3-Methyl-TTNCB | 13 |
| 1,25-D + 3-methyl-TTNCB | 190 |

As shown, the above results indicate that each pair of receptors (RXRα/PPAR and RXRβ/VDR, respectively), in the presence of ligands known to specifically activate their respective receptors, are capable of producing a synergistic response. The results indicate that the response of a single agent can be enhanced by the combination of the two agents, or that comparable biological or therapeutic responses can be achieved by use of lower doses of such agents in combination.

The observation that RXR-specific ligands are able to act synergistically with RAR ligands, PPAR ligands, and Vitamin D ligands indicates that RXR-specific ligands have usefulness not only as single therapeutic agents but also in combination therapy to obtain enhanced biological or therapeutic response by the addition of the RXR-specific ligand. Such combination therapy also may provide an added benefit of decreasing the side effects associated with the primary agent by employing lower doses of that agent. For example, use of Vitamin D or a related Vitamin D receptor ligand in conjunction with an RXR selective compound for the treatment of a variety of disorders including skin diseases (acne, psoriasis), hyperproliferative disorders (benign and malignant cancers) and disorders of calcium homeostasis may decrease the adverse side effects associated with Vitamin D therapy alone.

As a further example, the RXR-specific compounds of this invention have been demonstrated in vitro to act synergistically with compounds which affect cellular proliferation, such as Interferon. Specifically, the growth properties of two human tumor cell lines (ME180, a squamous cell carcinoma, and RPMI18226, a multiple myeloma) were monitored in the presence of the compound methyl-TTNEB alone and in combination with Interferonα2b, utilizing standard cell culture procedures. The effects on growth of these cells were monitored by evaluation of cell number, and also by evaluation of growth in semi-solid medium for the RPMI18226 cell line. Both 3-methyl-TTNEB and Interferonα2b were found to inhibit cell growth in a concentration-dependent manner, and each alone to produce a significant depression in cell proliferation. In addition, when the cells were treated with both compounds, in an additive or a greater than additive effect on the depression in cell proliferation was observed. Treatment with other chemotherapeutic agents including anti-proliferative agents and/or cell-cycle modulators (e.g., methotrexate, fluorourocil (5-FU, ARA-C, etc.)) in combination with RXR-specific compounds would be expected to produce similar results. The enhanced anti-proliferative effect can be expected to permit lower therapeutic doses in treatment of proliferative disorders, such as squamous cell and other carcinomas. In addition, combination therapy could allow the use of lower doses of these compounds to achieve a comparable beneficial effect along with fewer side effects/toxic effects, thereby enhancing the therapeutic index of the therapy. The therapeutic index is defined as the ratio of efficacy to toxicity of a compound.

Since RXR is known to form heterodimers with various members of the intracellular receptor super family, it can be expected that the synergistic response observed with use of RXR-selective ligands may be achieved with other receptors with which heterodimers are formed. These include PPARs, RARs, Vitamin D, thyroid hormone receptors, HNF4, the COUP family of receptors, as referenced above, and other as yet unidentified members of the intracellular super family of receptors.

As will be further discernible to those skilled in the art, the compounds disclosed above can be readily utilized in pharmacological applications where selective retinoid receptor activity is desired, and where it is desired to minimize cross reactivities with other related intracellular receptors. In vivo applications of the invention include administration of the disclosed compounds to mammalian subjects, and in particular to humans.

The compounds of the present invention are small molecules which are relatively fat soluble or lipophilic and enter the cell by passive diffusion across the plasma membrane. Consequently, these ligands are well suited for administration orally and by injection, as well as topically. Upon administration, these ligands can selectively activate retinoid X receptors, and thereby selectively modulate processes mediated by these receptors.

The pharmaceutical compositions of this invention are prepared in conventional dosage unit forms by incorporating an active compound of the invention, or a mixture of such compounds, with a nontoxic pharmaceutical carrier according to accepted procedures in a nontoxic amount sufficient to produce the desired pharmacodynamic activity in a mammalian and in particular a human subject. Preferably, the composition contains the active ingredient in an active, but nontoxic, amount selected from about 5 mg to about 500 mg of active ingredient per dosage unit. This quantity depends on the specific biological activity desired and the condition of the patient.

The pharmaceutical carrier or vehicle employed may be, for example, a solid or liquid. A variety of pharmaceutical forms can be employed. Thus, when using a solid carrier, the preparation can be plain milled, micronized in oil, tableted, placed in a hard gelatin or enteric-coated capsule in micronized powder or pellet form, or in the form of a troche, lozenge, or suppository. When using a liquid carrier, the preparation can be in the form of a liquid, such as an ampule, or as an aqueous or nonaqueous liquid suspension. For topical administration, the active ingredient may be formulated using bland, moisturizing bases, such as ointments or creams. Examples of suitable ointment bases are petrolatum, petrolatum plus volatile silicones, lanolin, and water in oil emulsions such as Eucerin (Beiersdorf). Examples of suitable cream bases are Nivea Cream (Beiersdorf), cold cream (USP), Purpose Cream (Johnson & Johnson) hydrophilic ointment (USP), and Lubriderm (Warner-Lambert).

The following examples provide illustrative pharmacological composition formulations:

EXAMPLE 62

Hard gelatin capsules are prepared using the following ingredients:

| (mg/capsule) | Quantity |
|---|---|
| 3-methyl-TTNCB | 140 |
| Starch, dried | 100 |
| Magnesium stearate | 10 |
| Total | 250 mg |

The above ingredients are mixed and filled into hard gelatin capsules in 250 mg quantities.

EXAMPLE 63

A tablet is prepared using the ingredients below:

| | Quantity (mg/tablet) |
|---|---|
| 3-methyl-TTNCB | 140 |
| Cellulose, microcrystalline | 200 |
| Silicon dioxide, fumed | 10 |
| Stearic acid | 10 |
| Total | 360 mg |

The components are blended and compressed to form tablets each weighing 360 mg.

EXAMPLE 64

Tablets, each containing 60 mg of active ingredient, are made as follows:

| | Quantity (mg/tablet) |
|---|---|
| 3-methyl-TTNCB | 60 |
| Starch | 45 |
| Cellulose, microcrystalline | 35 |
| Polyvinylpyrrolidone (PVP) (as 10% solution in water) | 4 |
| Sodium carboxymethyl starch (SCMS) | 4.5 |
| Magnesium stearate | 0.5 |
| Talc | 1.0 |
| Total | 150 mg |

The active ingredient, starch, and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. and passed through a No. 18 mesh U.S. sieve. The SCMS, magnesium stearate, and talc, previously passed through a No. 60 mesh U.S. sieve, are then added to the granules which, after mixing, are compressed on a tablet machine to yield tablets each weighing 150 mg.

EXAMPLE 65

Suppositories, each containing 225 mg of active ingredient, may be made as follows:

| | |
|---|---|
| 3-methyl-TTNCB | 225 mg |
| Saturated fatty acid glyceridse | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of normal 2 g capacity and allowed to cool.

EXAMPLE 66

An intravenous formulation may be prepared as follows:

| | |
|---|---|
| 3-methyl-TTNCB | 100 mg |
| Isotonic saline | 1,000 ml |
| Glycerol | 100 ml |

The compound is dissolved in the glycerol and then the solution is slowly diluted with isotonic saline. The solution of the above ingredients is then administered intravenously at a rate of 1 ml per minute to a patient.

The compounds of this invention also have utility when labeled as ligands for use in assays to determine the presence RXRs. They are particularly useful due to their ability to selectively bond to members of the RXR subfamily and can therefore be used to determine the presence of RXR isoforms in the presence of other related receptors.

Due to the selective specificity of the compounds of this invention for retinoid X receptors, these compounds can also be used to purify samples of retinoid X receptors in vitro. Such purification can be carried out by mixing samples containing retinoid X receptors with one of more of the bicyclic derivative compounds disclosed so that the compound (ligand) binds to the receptor, and then separating out the bound ligand/receptor combination by separation techniques which are known to those of skill in the art. These techniques include column separation, filtration, centrifugation, tagging and physical separation, and antibody complexing, among others.

While the preferred embodiments have been described and illustrated, various substitutions and modifications may be made thereto without departing from the scope of the invention. Accordingly, it is to be understood that the present invention has been described by way of illustration and not limitation.

We claim:

1. A pharmaceutical composition comprising in a pharmaceutically acceptable vehicle suitable for enteral, parenteral, or topical administration, one or more compound, or a pharmaceutically acceptable ester, amide or salt thereof, said compound selected from the group consisting of:

3-methyl-7-ethyl-9-(2,6,6-trimethyl-1-cyclohexen-1-yl)-2E,4E,6Z,8E-nonatetranoic acid, 3-methyl-7-propyl-9-(2,6,6-trimethyl-1-cyclohexen-1-yl)-2E,4E,6Z,8E-nonatetranoic acid, 3-methyl-7-isopropyl-9-(2,6,6-trimethyl-1-cyclohexen-1-yl)-2E,4E,6Z,8E-nonatetranoic acid, 3,6,7-trimethyl-9-(2,6,6-trimethyl-1-cyclohexen-1-yl)-2E,4E,6Z,8E-nonatetranoic acid, 3-methyl-7-t-butyl-9-(2,6,6-trimethyl-1-cyclohexen-1-yl)-2E,4E,6Z,8E-nonatetranoic acid, 3-methyl-5-{2-[2-(2,6,6-trimethylcyclohexen-1-yl)ethenyl]phenyl}-2E,4E-pentadienoic acid, 3-methyl-5-{2-[2-(2,6,6-trimethylcyclohexen-1-yl)ethenyl]cyclohexyl}-2E,4E-pentadienoic acid, (2E,4E)-3-methyl-6-{1-[2,6,6-trimethyl-1-cyclohexenyl)ethenyl]cyclopropyl}-2,4-hexadienoic acid, (2E,4E,6Z)-7-(5,5,8,8-tetramethyl-5,6,7,8-tetrahydro-2-naphthyl)-3,8-dimethyl-nona-2,4,6-trienoic acid, and (2E,4E,6Z)-7-(3,5,5,8,8-pentamethyl-5,6,7,8-tetrahydro-2-naphthyl)-3-methyl-octa-2,4,6-trienoic acid.

2. A therapeutic process comprising administering to a subject a compound which in a co-transfection assay is more potent an activator of a Retinoid X Receptor than a Retinoic Acid Receptor, wherein said compound is useful to modulate in vivo lipid metabolism, in vivo lipid homeostasis, in vivo skin-related processes, in vivo autoimmune diseases, in vivo fatty acid metabolism, in vivo malignant cell development, in vivo premalignant lesions, in vivo programmed cell death, or in vivo endocrinological processes.

3. A therapeutic process according to claim 2, wherein said compound is at least three times more potent an activator of a Retinoid X Receptor than a Retinoic Acid Receptor.

4. A therapeutic process according to claim 2, wherein said compound is at least five times more potent an activator of a Retinoid X Receptor than a Retinoic Acid Receptor.

5. A therapeutic process comprising administering to a subject a compound which in a co-transfection assay is more potent an activator of a Retinoid X Receptor than a Retinoic Acid Receptor, wherein said compound is useful to treat dermatological conditions, keratinization disorders, proliferative disorders, differentiation disorders, comedolytic activity, cancer, inflammatory diseases, hyperlipidemia, cardiovascular disorders, apolipoprotein AI metabolism, AP-1 metabolism, or plasma HDL levels.

6. A therapeutic process comprising administering to a subject a compound which in a co-transfection assay is more potent an activator of a Retinoid X Receptor than a Retinoic Acid Receptor, wherein said compound is useful to treat acne, psoriasis, aging, wrinkling, acute promyelocytic leukemia, mammary cancer, prostate cancer, lung cancer, cancers of the aerodigestive pathway, skin cancer, bladder cancer, sarcomas, or leukoplakias.

7. A pharmaceutical composition comprising a compound which is more potent an activator of a Retinoid X Receptor than a Retinoic Acid Receptor in a co-transfection assay in combination with a pharmaceutically acceptable vehicle.

8. A pharmaceutical composition according to claim 7, wherein said compound is at least three times more potent an activator of a Retinoid X Receptor than a Retinoic Acid Receptor.

9. A pharmaceutical composition according to claim 7, wherein said compound is at least five times more potent an activator of a Retinoid X Receptor than a Retinoic Acid Receptor.

10. A pharmaceutical composition comprising a compound which modulates a process mediated by a Retinoid X Receptor in combination with a pharmaceutically acceptable vehicle, wherein said compound selectively activates one or more Retinoid X Receptors in preference to Retinoic Acid Receptors.

11. A pharmaceutical composition according to claim 10, wherein said compound is at least three times more potent an activator of a Retinoid X Receptor than a Retinoic Acid Receptor.

12. A pharmaceutical composition according to claim 10, wherein said compound is at least five times more potent an activator of a Retinoid X Receptor than a Retinoic Acid Receptor.

13. A method for modulating a process mediated by one or more Retinoid X Receptors, said method comprising causing said process to be conducted in the presence of at least one compound which is more potent an activator of one or more of the Retinoid X Receptors than one or more of the Retinoic Acid Receptors in a co-transfection assay, wherein said process is the in vivo modulation of lipid metabolism, lipid homeostasis, hyperlipidemia, skin-related processes, autoimmune diseases, fatty acid metabolism, malignant cell development, premalignant lesions, programmed cell death, endocrinological processes, or AP-1 metabolism.

14. A method according to claim 13, wherein said compound is at least three times more potent an activator of a Retinoid X Receptor than a Retinoic Acid Receptor.

15. A method according to claim 13, wherein said compound is at least five times more potent an activator of a Retinoid X Receptor than a Retinoic Acid Receptor.

16. A method for treating a mammalian subject requiring Retinoid X Receptor therapy comprising administering to such a subject a pharmaceutically effective amount of a compound which is more potent an activator of a Retinoid X Receptor than a Retinoic Acid Receptor in a co-transfection assay, wherein said process is the in vivo modulation of lipid metabolism, lipid homeostasis, hyperlipidemia, skin-related processes, autoimmune diseases, fatty acid metabolism, malignant cell development, premalignant lesions, programmed cell death, endocrinological processes, or AP-1 metabolism.

17. A method according to claim 16, wherein said compound is at least three times more potent an activator of a Retinoid X Receptor than a Retinoic Acid Receptor.

18. A method according to claim 16, wherein said compound is at least five times more potent an activator of a Retinoid X Receptor than a Retinoic Acid Receptor.

19. A composition effective to inhibit abnormal cellular proliferation comprising a first compound which is more potent an activator of a Retinoid X Receptor than a Retinoic Acid Receptor in a co-transfection assay in combination with a second compound which affects cellular proliferation or is a cell-cycle modulator.

20. A composition according to claim 19, wherein said first compound is at least three times more potent an activator of a Retinoid X Receptor than a Retinoic Acid Receptor.

21. A composition according to claim 19, wherein said first compound is at least five times more potent an activator of a Retinoid X Receptor than a Retinoic Acid Receptor.

22. A composition according to claim 19, wherein the inhibition of cellular proliferation achieved by said composition at a given concentration is greater than the additive effect achieved by using each of said first and second compounds alone at said given concentration.

23. A composition according to claim 19, wherein said second compound is selected from the group consisting of interferon, methotrexate, fluorouracil, and ARA-C.

* * * * *

UNITED STATES PATENT AND TRADEMARK OFFICE

CERTIFICATE OF CORRECTION

PATENT NO. : 5,780,676

DATED : July 14, 1998

INVENTOR(S) : BOEHM et al.

It is certified that error appears in the above-identified patent and that said Letters Patent are hereby corrected as shown below:

Column 67, lines 1-2, change "a Retinoic Acid Receptor" to -- all of Retinoic Acid Receptor isoforms α, β, and γ --.

Column 67, lines 17-18, change "a Retinoic Acid Receptor" to -- all of Retinoic Acid Receptor isoforms α, β, and γ --.

Column 67, lines 26-27, change "a Retinoic Acid Receptor" to -- all of Retinoic Acid Receptor isoforms α, β, and γ --.

Column 67, line 34, change "a Retinoic Acid Receptor" to -- all of Retinoic Acid Receptor isoforms α, β, and γ --.

Column 67, lines 48-49, change "Retinoic Acid Receptors" to -- all of Retinoic Acid Receptor isoforms α, β, and γ --.

Column 68, lines 5-6, change "one or more of the Retinoic Acid Receptors" to -- all of the Retinoic Acid Receptor isoforms α, β, and γ --.

Column 68, line 22, change "a Retinoic Acid Receptor" to -- all of Retinoic Acid Receptor isoforms α, β, and γ --.

Column 68, lines 37-38, change "a Retinoic Acid Receptor" to -- all of Retinoic Acid Receptor isoforms α, β, and γ --.

UNITED STATES PATENT AND TRADEMARK OFFICE

CERTIFICATE OF CORRECTION

PATENT NO. : 5,780,676

DATED : July 14, 1998

INVENTOR(S) : BOEHM et al.

It is certified that error appears in the above-identified patent and that said Letters Patent are hereby corrected as shown below:

Column 68, beginning at line 56, add the following:

24. The therapeutic process of claim 2 wherein said compound is useful to modulate in vivo skin-related processes.

25. The therapeutic process of claim 2 wherein said compound is useful to modulate in vivo malignant cell development.

26. The therapeutic process of claim 2 wherein said compound is useful to modulate in vivo premalignant lesions.

27. The therapeutic process of claim 2 wherein said compound is useful to modulate in vivo programmed cell death.

28. The therapeutic process of claim 5 wherein said compound is useful to treat dermatological conditions.

29. The therapeutic process of claim 5 wherein said compound is useful to treat proliferative disorders.

30. The therapeutic process of claim 5 wherein said compound is useful to treat cancer.

31. The therapeutic process of claim 6 wherein said compound is useful to treat psoriasis.

32. The therapeutic process of claim 6 wherein said compound is useful to treat aging.

33. The therapeutic process of claim 6 wherein said compound is useful to treat mammary cancer.

UNITED STATES PATENT AND TRADEMARK OFFICE

CERTIFICATE OF CORRECTION

PATENT NO. : 5,780,676

DATED : July 14, 1998

INVENTOR(S) : BOEHM et al.

It is certified that error appears in the above-identified patent and that said Letters Patent are hereby corrected as shown below:

34. The therapeutic process of claim 6 wherein said compound is useful to treat prostate cancer.

35. The therapeutic process of claim 6 wherein said compound is useful to treat lung cancer.

36. The therapeutic process of claim 6 wherein said compound is useful to treat cancers of the aerodigestive pathway.

37. The therapeutic process of claim 6 wherein said compound is useful to treat skin cancer.

38. The therapeutic process of claim 6 wherein said compound is useful to treat bladder cancer.

Signed and Sealed this

Twentieth Day of April, 1999

Attest:

Q. TODD DICKINSON

*Attesting Officer*

*Acting Commissioner of Patents and Trademarks*

US005780676C1

(12) REEXAMINATION CERTIFICATE (4733rd)

United States Patent

Boehm et al.

(10) Number: US 5,780,676 C1

(45) Certificate Issued: Feb. 11, 2003

(54) COMPOUNDS HAVING SELECTIVE ACTIVITY FOR RETINOID X RECEPTORS, AND MEANS FOR MODULATION OF PROCESSES MEDIATED BY RETINOID X RECEPTORS

(75) Inventors: Marcus F. Boehm, San Diego, CA (US); Richard A. Heyman, Encinitas, CA (US); Lin Zhi, San Diego, CA (US); Chan Kou Hwang, San Diego, CA (US); Steve White, San Diego, CA (US); Alex Nadzan, San Diego, CA (US)

(73) Assignee: Ligand Pharmaceuticals Incorporated, San Diego, CA (US)

Reexamination Request:
No. 90/005,296, Mar. 16, 1999

Reexamination Certificate for:

| | |
|---|---|
| Patent No.: | **5,780,676** |
| Issued: | **Jul. 14, 1998** |
| Appl. No.: | **08/485,386** |
| Filed: | **Jun. 7, 1995** |

Certificate of Correction issued Apr. 20, 1999.

Related U.S. Application Data

(63) Continuation of application No. 08/141,246, filed on Oct. 22, 1993, which is a continuation-in-part of application No. 08/052,050, filed on Apr. 21, 1993, now abandoned, which is a continuation-in-part of application No. 08/027,747, filed on Mar. 5, 1993, now abandoned, which is a continuation-in-part of application No. 08/003,223, filed on Jan. 11, 1993, now abandoned, which is a continuation-in-part of application No. 07/944,783, filed on Sep. 11, 1992, now abandoned, which is a continuation-in-part of application No. 07/872,707, filed on Apr. 22, 1992, now abandoned.

(51) Int. Cl.[7] ................................ C07C 63/36

(52) U.S. Cl. ....................... 562/490; 562/501; 554/220; 554/221

(58) Field of Search ................................ 562/490, 501; 554/220, 221

(56) References Cited

U.S. PATENT DOCUMENTS 4,166,107 A 8/1979 Miller et al.
4,981,784 A 1/1991 Evans et al.
5,428,071 A 6/1995 Bollag et al.

OTHER PUBLICATIONS

Prasert et al., Journal of Economic Entomology, vol. 68, No. 5, pp. 639–640 (1975).

Quistad et al., J. Agric. Food Chem., vol. 23, No. 4, pp. 743–749 (1975).

Wright, Environmental Health Perspectives, vol. 14, pp. 127–132 (1976).

Staal, Annual Review of Entymology, vol. 20, pp. 417–460 (1975).

Harmon et al., Proc. Nat'l Acad. Sci. USA, vol. 92, pp. 6157–6160 (1995).

Mei et al, ACS Symposium Series 442, *Immunochemical Methods for Environmental Analysis,* Chapter 12 (1990).

Mize et al., Journal of Lipid Research, vol. 7, pp. 692–697 (1966).

Kitareewan et al., Molecular Biology of the Cell, vol. 7, pp. 1153–1166 (1996).

Lotan, Biochimica et Biophysica Acta, 605 (1980 Elsevier/North Holland Biomedical Press).

Heyman et al., Cell, vol. 68, pp. 397–406 (1992).

Mangelsdorf, et al., Nature, vol. 345, p. 224–229 (1990).

Graupner, et al., Biochemical and Biophysical Research Communications, vol. 179, No. 3, pp. 1554–1561 (1991).

La Vista–Picard, et al., Molecular and Cellular Biology, vol. 16, No. 8, pp. 4137–4146 (1996).

*Primary Examiner*—Paul J. Killos

(57) ABSTRACT

Compounds, compositions, and methods for modulating processes mediated by Retinoid X Receptors using retinoid-like compounds which have activity selective for members of the subclass of Retinoid X Receptors (RXRs), in preference to members of the subclass of Retinoic Acid Receptors (RARs). Examples of such compounds are bicyclic benzyl, pyridinyl, thiophene, furanyl, pyrrole, and poiyenoic acid derivatives including carbocyclic polyenoic acids. The disclosed methods employ compounds for modulating processes selectively mediated by Retinoid X Receptors.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1, 5–6, 19–23, and 28–38 is confirmed.

Claims 2, 7, 10, 13 and 16 are determined to be patentable as amended.

Claims 3–4, 8–9, 11–12, 14–15, 17–18, and 24–27, dependent on an amended claim, are determined to be patentable.

New claims 39–99 are added and determined to be patentable.

2. A therapeutic process comprising administering to a *mammalian* subject a compound which in a co-transfection assay is more potent an activator of a Retinoid X Receptor than [a] *all of* Retinoic Acid Receptor *isoforms* α, β, *and* γ, wherein said compound is useful to modulate *said subject's* in vivo lipid metabolism, in vivo lipid homeostasis, in vivo skin-related processes, in vivo autoimmune diseases, in vivo fatty acid metabolism, in vivo malignant cell development, in vivo premalignant lesions, in vivo programmed cell death, or in vivo endocrinological processes.

7. A pharmaceutical composition comprising a compound which is more potent an activator of a Retinoid X Receptor than [a] *all of* Retinoic Acid Receptor *isoforms* α, β, *and* γ in a co-transfection assay *and has an EC50 potency concentration requirement of 240 nM or less on one or more of the RXR isoforms* α, β, *and* γ, in combination with a pharmaceutically acceptable vehicle.

10. A pharmaceutical composition comprising a compound which modulates a process mediated by a Retinoid X Receptor in combination with a pharmaceutically acceptable vehicle, wherein said compound selectively activates one or more Retinoid X Receptors in preference to *all of* Retinoic Acid Receptor[s] *isoforms* α, β, *and* γ, *and has an EC50 potency concentration requirement of 240 nm or less on one or more of the RXR isoforms* α, β, *and* γ.

13. A method for modulating *in a mammalian subject* a process mediated by one or more Retinoid X Receptors, said method comprising causing said process to be conducted in the presence of at least one compound which is more potent an activator of one or more of the Retinoid X Receptors than [one or more] *all* of the Retinoid Acid Receptor[s] *isoforms* α, β, *and* γ in a co-transfection assay, wherein said process is the in vivo modulation of *said subject's* lipid metabolism, lipid homeostasis, hyperlipidemia, skin-related processes, autoimmune diseases, fatty acid metabolism, malignant cell development, premalignant lesions, programmed cell death, endocrinological processes, or AP-1 metabolism.

16. A method for treating a mammalian subject requiring Retinoid X Receptor therapy comprising administering to such a subject a pharmaceutically effective amount of a compound which is more potent an activator of a Retinoid X Receptor than [a] *all of* Retinoic Acid Receptor *isoforms* α, β, *and* γ in a co-transfection assay, wherein said [process] *treatment* is the in vivo modulation of *said subject's* lipid metabolism, lipid homeostasis, hyperlipidemia, skin-related processes, autoimmune diseases, fatty acid metabolism, malignant cell development, premalignant lesions, programmed cell death, endocrinological processes, or AP-1 metabolism.

*39. The therapeutic process of claim 2 wherein said compound has an EC50 potency concentration requirement of 240 nM or less on one or more of the RXR isoforms α, β, and γ.*

*40. The therapeutic process of claim 2 wherein said compound has an EC50 potency concentration requirement of 40 nM or less on one or more of the RXR isoforms α, β, and γ.*

*41. The therapeutic process of claim 2 wherein said compound has an EC50 potency concentration requirement of 10 nM or less on one or more of the RXR isoforms α, β, and γ.*

*42. The therapeutic process of claim 5 wherein said compound has an EC50 potency concentration requirement of 240 nM or less on one or more of the RXR isoforms α, β, and γ.*

*43. The therapeutic process of claim 5 wherein said compound has an EC50 potency concentration requirement of 40 nM or less on one or more of the RXR isoforms α, β, and γ.*

*44. The therapeutic process of claim 5 wherein said compound has an EC50 potency concentration requirement of 10 nM or less on one or more of the RXR isoforms α, β, and γ.*

*45. The therapeutic process of claim 6 wherein said compound has an EC50 potency concentration requirement of 240 nM or less on one or more of the RXR isoforms α, β, and γ.*

*46. The therapeutic process of claim 6 wherein said compound has an EC50 potency concentration requirement of 40 nM or less on one or more of the RXR isoforms α, β, and γ.*

*47. The therapeutic process of claim 6 wherein said compound has an EC50 potency concentration requirement of 10 nM or less on one or more of the RXR isoforms α, β, and γ.*

*48. The pharmaceutical composition of claim 7 wherein said compound has an EC50 potency concentration of 40 nM or less on one or more of the RXR isoforms α, β, and γ.*

*49. The pharmaceutical composition of claim 7 wherein said compound has an EC50 potency concentration of 10 nM or less on one or more of the RXR isoforms α, β, and γ.*

*50. The pharmaceutical composition of claim 10 wherein said compound has an EC50 potency concentration of 40 nM or less on one or more of the RXR isoforms α, β, and γ.*

*51. The pharmaceutical composition of claim 10 wherein said compound has an EC50 potency concentration of 10 nM or less on one or more of the RXR isoforms α, β, and γ.*

*52. The method of claim 13 wherein said compound has an EC50 potency concentration requirement of 240 nM or less on one or more of the RXR isoforms α, β, and γ.*

*53. The method of claim 13 wherein said compound has an EC50 potency concentration requirement of 40 nM or less on one or more of the RXR isoforms α, β, and γ.*

*54. The method of claim 13 wherein said compound has an EC50 potency concentration requirement of 10 nM or less on one or more of the RXR isoforms α, β, and γ.*

*55. The method of claim 16 wherein said compound has an EC50 potency concentration requirement of 240 nM or less on one or more of the RXR isoforms α, β, and γ.*

*56. The method of claim 16 wherein said compound has an EC50 potency concentration requirement of 40 nM or less on one or more of the RXR isoforms α, β, and γ.*

*57. The method of claim 16 wherein said compound has an EC50 potency concentration requirement of 10 nM or less on one or more of the RXR isoforms α, β, and γ.*

*58. The composition of claim 19 wherein said compound has an EC50 potency concentration requirement of 240 nM or less on one or more of the RXR isoforms α, β, and γ.*

*59. The composition of claim 19 wherein said compound has an EC50 potency concentration requirement of 40 nM or less on one or more of the RXR isoforms α, β, and γ.*

*60. The composition of claim 19 wherein said compound has an EC50 potency concentration requirement of 10 nM or less on one or more of the RXR isoforms α, β, and γ.*

*61. The therapeutic process of claim 2 wherein said compound has a $Kd_{50}$ binding affinity for one or more of the RXR isoforms α, β, and γ of 365 nM or less.*

*62. The therapeutic process of claim 2 wherein said compound has a $Kd_{50}$ binding affinity for one or more of the RXR isoforms α, β, and γ of 41 nM or less.*

*63. The therapeutic process of claim 2 wherein said compound has a $Kd_{50}$ binding affinity for one or more of the RXR isoforms α, β, and γ of 3 nM or less.*

*64. The therapeutic process of claim 5 wherein said compound has a $Kd_{50}$ binding affinity for one or more of the RXR isoforms α, β, and γ of 365 nM or less.*

*65. The therapeutic process of claim 5 wherein said compound has a $Kd_{50}$ binding affinity for one or more of the RXR isoforms α, β, and γ of 41 nM or less.*

*66. The therapeutic process of claim 5 wherein said compound has a $Kd_{50}$ binding affinity for one or more of the RXR isoforms α, β, and γ of 3 nM or less.*

*67. The therapeutic process of claim 6 wherein said compound has a $Kd_{50}$ binding affinity for one or more of the RXR isoforms α, β, and γ of 365 nM or less.*

*68. The therapeutic process of claim 6 wherein said compound has a $Kd_{50}$ binding affinity for one or more of the RXR isoforms α, β, and γ of 41 nM or less.*

*69. The therapeutic process of claim 6 wherein said compound has a $Kd_{50}$ binding affinity for one or more of the RXR isoforms α, β, and γ of 3 nM or less.*

*70. A pharmaceutical composition comprising a compound which is more potent an activator of a Retinoid X Receptor than all of Retinoic Acid Receptor isoforms α, β, and γ in a co-transfection assay and has a $Kd_{50}$ binding affinity for one or more of the RXR isoforms α, β, and γ of 365 nM or less in combination with a pharmaceutically acceptable vehicle.*

*71. The pharmaceutical composition of claim 70 wherein said compound has a $Kd_{50}$ binding affinity for one or more of the RXR isoforms α, β, and γ of 41 nM or less.*

*72. The pharmaceutical composition of claim 70 wherein said compound has a $Kd_{50}$ binding affinity for one or more of the RXR isoforms α, β, and γ of 3 nM or less.*

*73. A pharmaceutical composition comprising a compound which modulates a process mediated by a Retinoid X Receptor in combination with a pharmaceutically acceptable vehicle, wherein said compound selectively activates one or more Retinoid X Receptors in preference to all of Retinoic Acid Receptor isoforms α, β, and γ and has a $Kd_{50}$ binding affinity for one or more of the RXR isoforms α, β, and γ of 365 nM or less.*

*74. The pharmaceutical composition of claim 73 wherein said compound has a $Kd_{50}$ binding affinity for one or more of the RXR isoforms α, β, and γ of 41 nM or less.*

*75. The pharmaceutical composition of claim 73 wherein said compound has a $Kd_{50}$ binding affinity for one or more of the RXR isoforms α, β, and γ of 3 nM or less.*

*76. The method of claim 13 wherein said compound has a $Kd_{50}$ binding affinity for one or more of the RXR isoforms α, β, and γ of 365 nM or less.*

*77. The method of claim 13 wherein said compound has a $Kd_{50}$ binding affinity for one or more of the RXR isoforms α, β, and γ of 41 nM or less.*

*78. The method of claim 13 wherein said compound has a $Kd_{50}$ binding affinity for one or more of the RXR isoforms α, β, and γ of 3 nM or less.*

*79. The method of claim 16 wherein said compound has a $Kd_{50}$ binding affinity for one or more of the RXR isoforms α, β, and γ of 365 nM or less.*

*80. The method of claim 16 wherein said compound has a $Kd_{50}$ binding affinity for one or more of the RXR isoforms α, β, and γ of 41 nM or less.*

*81. The method of claim 16 wherein said compound has a $Kd_{50}$ binding affinity for one or more of the RXR isoforms α, β, and γ of 3 nM or less.*

*82. The composition of claim 19 wherein said compound has a $Kd_{50}$ binding affinity for one or more of the RXR isoforms α, β, and γ of 365 nM or less.*

*83. The composition of claim 19 wherein said compound has a $Kd_{50}$ binding affinity for one or more of the RXR isoforms α, β, and γ of 41 nM or less.*

*84. The composition of claim 19 wherein said compound has a $Kd_{50}$ binding affinity for one or more of the RXR isoforms α, β, and γ of 3 nM or less.*

*85. The therapeutic process of claim 2 wherein said subject is a human subject.*

*86. The therapeutic process of claim 5 wherein said subject is a human subject.*

*87. The therapeutic process of claim 6 wherein said subject is a human subject.*

*88. A pharmaceutical composition for use in a human subject comprising a compound which is more potent an activator of a Retinoid X Receptor than all of Retinoic Acid Receptor isoforms α, β, and γ in a cotransfection assay in combination with a pharmaceutically acceptable vehicle.*

*89. A pharmaceutical composition for use in a human subject comprising a compound which modulates a process mediated by a Retinoid X Receptor in combination with a pharmaceutically acceptable vehicle, wherein said compound selectively activates one or more Retinoid X Receptors in preference to all of Retinoic Acid Receptor isoforms α, β, and γ.*

*90. The method of claim 16 wherein said subject is a human subject.*

*91. The therapeutic process of claim 2 and wherein said compound is a carbocyclic, bicyclic or aromatic compound.*

*92. The therapeutic process of claim 5 and wherein said compound is a carbocyclic, bicyclic or aromatic compound.*

*93. The therapeutic process of claim 6 and wherein said compound is a carbocyclic, bicyclic or aromatic compound.*

*94. A pharmaceutical composition comprising a carbocyclic, bicyclic or aromatic compound which is more potent an activator of a Retinoid X Receptor than all of Retinoic Acid Receptor isoforms α, β, and γ in a co-transfection assay in combination with a pharmaceutically acceptable vehicle.*

*95. A pharmaceutical composition comprising a carbocyclic, bicyclic or aromatic compound which modulates a process mediated by a Retinoid X Receptor in combination with a pharmaceutically acceptable vehicle, wherein said compound selectively activates one or more Retinoid X Receptors in preference to all of Retinoic Acid Receptor isoforms α, β, and γ.*

*96. The method of claim 13 and wherein said compound is a carbocyclic, bicyclic or aromatic compound.*

*97. The method of claim 16 and wherein said compound is a carbocyclic, bicyclic or aromatic compound.*

*98. The composition of claim 19 and wherein said first compound is carbocyclic, bicyclic or aromatic compound.*

*99. The composition of claim 98 wherein the inhibition of cellular proliferation achieved by said composition at a given concentration is greater than the additive effect achieved by using each of said first and second compounds alone at said given concentration.*

* * * * *